(12) United States Patent
Esteban Martín et al.

(10) Patent No.: US 10,639,348 B2
(45) Date of Patent: May 5, 2020

(54) PEPTIDES WITH ANTI-CANCER ACTIVITY

(71) Applicant: IDP DISCOVERY PHARMA, S.L., Barcelona (ES)

(72) Inventors: Santiago Esteban Martín, Barcelona (ES); Laura Nevola, Barcelona (ES)

(73) Assignee: IDP DISCOVERY PHARMA, S.L., Barcelona (ES)

( * ) Notice: Subject to any disclaimer, the term of this patent is extended or adjusted under 35 U.S.C. 154(b) by 0 days.

(21) Appl. No.: 16/084,927

(22) PCT Filed: Mar. 15, 2017

(86) PCT No.: PCT/EP2017/056074
§ 371 (c)(1),
(2) Date: Sep. 13, 2018

(87) PCT Pub. No.: WO2017/157990
PCT Pub. Date: Sep. 21, 2017

(65) Prior Publication Data
US 2019/0083570 A1    Mar. 21, 2019

(30) Foreign Application Priority Data

Mar. 15, 2016   (EP) .................................... 16382114

(51) Int. Cl.
| | |
|---|---|
| A61K 38/00 | (2006.01) |
| A61K 38/17 | (2006.01) |
| C07K 14/47 | (2006.01) |
| A61P 35/00 | (2006.01) |
| C07K 4/00 | (2006.01) |
| C07K 7/02 | (2006.01) |
| C07K 7/08 | (2006.01) |
| C07K 7/54 | (2006.01) |
| C07K 9/00 | (2006.01) |

(52) U.S. Cl.
CPC .............. *A61K 38/17* (2013.01); *A61P 35/00* (2018.01); *C07K 4/00* (2013.01); *C07K 7/02* (2013.01); *C07K 7/08* (2013.01); *C07K 7/54* (2013.01); *C07K 9/003* (2013.01); *C07K 14/47* (2013.01)

(58) Field of Classification Search
None
See application file for complete search history.

(56) References Cited

U.S. PATENT DOCUMENTS 5,595,756 A * 1/1997 Bally .................. A61K 9/1272
264/4.1

FOREIGN PATENT DOCUMENTS

WO      2010/034031 A1    3/2010

OTHER PUBLICATIONS

Zugazagoitia et al, Current Challenges in Cancer Treatment, Clinical Therapies, vol. 38, (2016), pp. 1551-1566 (Year: 2016).*
Sporn et at, "Chemoprevention of Cancer," Carcinogenesis, vol. 21 (2000), 525-530 (Year: 2000).*
Cromm et al., "Hydrocarbon Stapled Peptides as Modulators of Biological Function," ACS Chem. Biol. 10:1362-1375, 2015.
Database Geneseq [Online] Jan. 14, 2016 (Jan. 14, 2016), "C-myc protein derived alpha-helical peptide P7.", XP002762225, retrieved from EBI accession No. GSB:BCI55903 Database accession No. BCI55903 sequence. (1 page).
Giorello et al., "Inhibition of Cancer Cell Growth and c-Myc Transcriptional Activity by a c-Myc Helix 1-Type Peptide Fused to an Internalization Sequence," Cancer Research 58:3654-3659, 1998.
Schafmeister et al., "An All-Hydrocarbon Cross-Linking System for Enhancing the Helicity and Metabolic Stability of Peptides," J. Am. Chem. Soc. 122:5891-5892, 2000.
Walensky et al., "Hydrocarbon-Stapled Peptides: Principles, Practice, and Progress," J. Med. Chem. 57:6275-6288, 2014.
EBI Accession No. GSP:AXX36814, XP-002794354, "Peptidomimetic macrocycle synthesizing Myc helix 2 peptide #1," May 27, 2010. (1 page).
EBI Accession No. GSP:AXX36821, XP-002794353, "Peptidomimetic macrocycle synthesizing Myc helix 2 peptide #8," May 27, 2010. (1 page).

(Continued)

Primary Examiner — Thomas S Heard
(74) Attorney, Agent, or Firm — Seed Intellectual Property Law Group LLP

(57) ABSTRACT

The peptides of the invention are of formula (I) or (IV). The peptides of the invention are useful in the treatment of cancer.

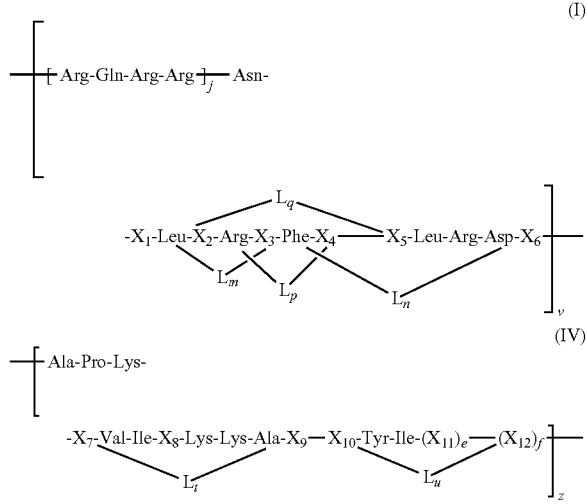

25 Claims, 1 Drawing Sheet
Specification includes a Sequence Listing.

(56) References Cited

OTHER PUBLICATIONS

EBI Accession No. GSP:AXX36822, XP-002794352, "Peptidomimetic macrocycle synthesizing Myc helix 2 peptide #9," May 27, 2010. (1 page).
EBI Accession No. GSP:AXX36885, XP-002794355, "Peptidomimetic macrocycle synthesizing Myc peptide #22," May 27, 2010. (1 page).
EBI Accession No. GSP:BCI55903, XP-002794356, "C-myc protein derived alpha-helical peptide P7," Jan. 14, 2016. (1 page).

* cited by examiner

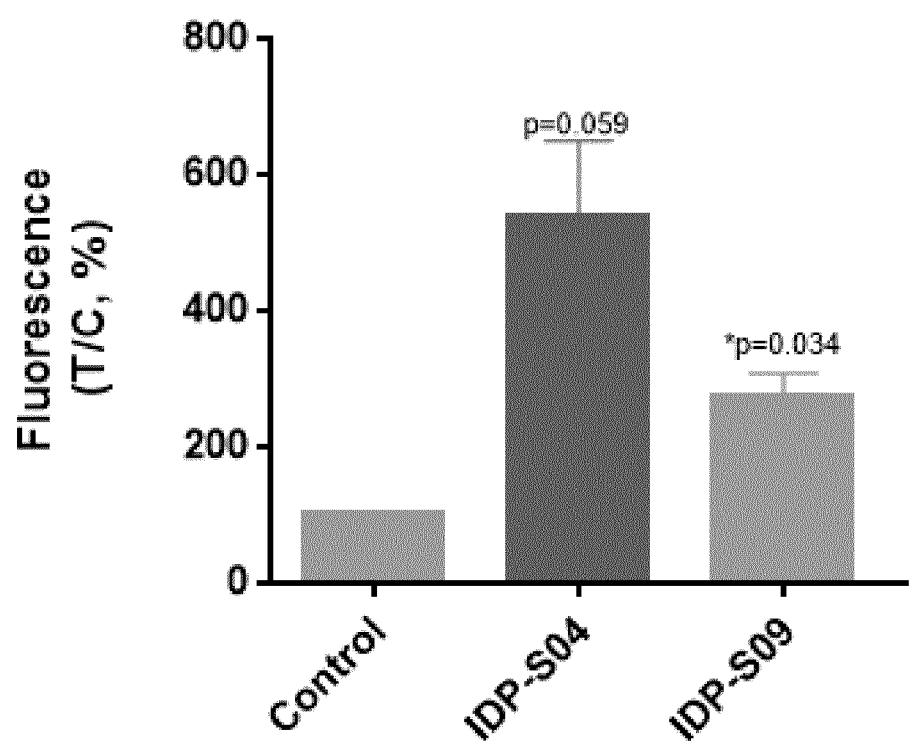

PEPTIDES WITH ANTI-CANCER ACTIVITY

This application claims the benefit of European Patent Application EP16382114.3 filed on Mar. 15, 2016.

This invention relates generally to the field of antineoplastic compounds and, more particularly, to the design and synthesis of peptides with improved anticancer activity.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480386_401USPC_SEQUENCE_LISTING.txt. The text file is 16 KB, was created on Sep. 12, 2018, and is being submitted electronically via EFS-Web.

BACKGROUND ART

The therapeutic use of proteins and peptides that act intracellularly holds much promise for the treatment of cancer and other diseases.

Cancer is the result in the occurrence of multiple factors. Mutations may occur in proto-oncogenes that cause cellular proliferation to increase. Mutations also may occur in tumor suppressors whose normal function is to regulate cellular proliferation. Mutations in DNA repair enzymes impair the ability of the cell to repair damage before proliferating.

Tumor suppressor genes are normal genes whose absence (loss or inactivation) can lead to cancer. Tumor suppressor genes encode proteins that slow cell growth and division. Wild-type alleles of tumor suppressor genes express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal cellular proliferation may take place, particularly if there is already existing damage to the cellular regulatory mechanism. A number of well-studied human tumors and tumor cell lines have been shown to have missing or nonfunctional tumor suppressor genes.

Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. These therapies each are accompanied with varying side effects and they have varying degrees of efficacy. These side effects, together with the multidrug resistance already disclosed for traditional chemotherapy, have prompted urgent needs for novel anticancer drugs or therapeutic approaches.

Anticancer peptides have become promising molecules for novel anticancer agents because of their unique mechanism and several extraordinary properties. However, properties such as the specificity and sensitivity shown by the peptides already disclosed in the prior art, need further improvement.

Thus, in spite of the efforts made, there is still the need of developing further polypeptides with appropriate anticancer profile.

SUMMARY OF THE INVENTION

The present inventors have developed short peptides showing anti-cancer activity.

As it is shown below, the peptides of the invention show improved specificity and sensitivity when compared with other peptides already disclosed in the prior art.

Thus, the present invention provides in a first a peptide or a pharmaceutical salt thereof comprising the sequence of formula (I)

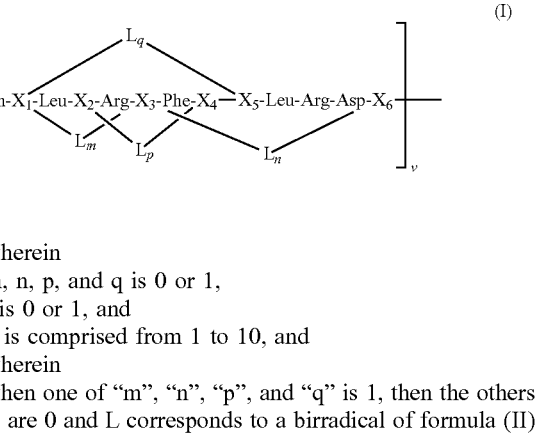

wherein
m, n, p, and q is 0 or 1,
j is 0 or 1, and
v is comprised from 1 to 10, and
wherein
when one of "m", "n", "p", and "q" is 1, then the others are 0 and L corresponds to a birradical of formula (II)

$$-P-[(R_1)_a-(R_2)-(R_3)_b]_c-Q-$$ (II)

"a" and "b" are the same or different and are 0 or 1;
"c" is comprised from 1 to 10;
$R_1$ and $R_3$ are birradicals independently selected from the group consisting of: $(C_1-C_{10})$alkyl, $(C_2-C_{10})$alkenyl, $(C_2-C_{10})$alkynyl, $(C_1-C_{10})$alkyl-O—$(C_1-C_{10})$alkyl, $(C_1-C_{10})$alkyl-C(=O)—$(C_1-C_{10})$alkyl, $(C_1-C_{10})$alkyl-O—C(O)—$(C_1-C_{10})$alkyl, $(C_1-C_{10})$alkyl-C(O)—$NR_8$—$(C_1-C_{10})$alkyl, $(C_1-C_{10})$alkyl-S—$(C_1-C_{10})$alkyl, $(C_1-C_{10})$alkyl-$SR_9$—$(C_1-C_{10})$alkyl, $(C_1-C_{10})$alkyl-S(=O)$_2$—$(C_1-C_{10})$alkyl, $(C_1-C_{10})$alkyl-S(=O)—$(C_1-C_{10})$alkyl, $(C_1-C_{10})$alkyl-O—S(=O)$_2$—O—$(C_1-C_{10})$alkyl, and $(C_1-C_{10})$alkyl-$NR_{10}$—$(C_1-C_{10})$alkyl;
$R_2$ is a birradical selected from the group consisting of: —O—, C(=O), C(=O)$R_4$, C(=O)$NR_5$, C(=O)O, S(=O), S(=O)$_2$, S($R_6$), N($R_7$), $(C_1-C_{10})$alkyl, $(C_2-C_{10})$alkenyl, $(C_2-C_{10})$alkynyl, $NR_{13}R_{14}$, —NH—NH—, —N=N—, —S—S—, and a known ring system comprising from 3 to 14 carbon atoms, the system comprising from 1 to 3 rings, where:
  each one of the rings is saturated, partially unsaturated, or aromatic;
  the rings are isolated, partially or totally fused, each one of the members forming the known ring system is selected from the group consisting of: —CH—, —CH$_2$—, —NH—, —N—, —SH—, —S—, and —O—; and
  the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—;

R$_4$, R$_5$, R$_6$, R$_7$, R$_8$, R$_9$, R$_{10}$, R$_{13}$, and R$_{14}$ are monoradicals selected from the group consisting of: hydrogen, (C$_1$-C$_{10}$)alkyl, (C$_2$-C$_{10}$)alkenyl, and (C$_2$-C$_{10}$)alkynyl;

P and Q are birradicals, the same or different, provided that when "a" and "b" are 0, or alternatively one of "a" and "b" is 0, then P and Q have a meaning different from R$_2$ radical, said P and Q birradicals being selected from the group consisting of: (C$_1$-C$_{10}$)alkyl, (C$_2$-C$_{10}$)alkenyl, and (C$_2$-C$_{10}$)alkynyl; or, alternatively, when "a" and "b" are 0, or alternatively one of "a" and "b" is 0, then P and Q are C(=O), and R$_2$ is selected from the group consisting of: —O—, S(R$_6$), N(R$_7$), (C$_1$-C$_{10}$)alkyl, (C$_2$-C$_{10}$)alkenyl, (C$_2$-C$_{10}$)alkynyl, —NR$_{13}$R$_{14}$, —NH—NH—, —N=N—, —S—S—, and a known ring system comprising from 3 to 14 carbon atoms, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—;

when both "a" and "b", are 1, then P and Q are selected from the group consisting of: —S—, (C$_1$-C$_{10}$)alkyl-S—, —NR'$_{10}$-, (C$_1$-C$_{10}$)alkyl-NR'$_{10}$, —O—, (C$_1$-C$_{10}$)-alkyl-O—, —C(=O), (C$_1$-C$_{10}$)alkyl-C(=O)—, —C(=O)O, (C$_1$-C$_{10}$)alkyl-C(=O)O—, C(=O)N—, (C$_1$-C$_{10}$)alkylC(=O)—, C(=O)S— and (C$_1$-C$_{10}$)alkyl-C(=O)S— being R'$_{10}$ a radical selected from the group consisting of: hydrogen, (C$_1$-C$_{10}$)alkyl, (C$_2$-C$_{10}$)alkenyl, and (C$_1$-C$_{10}$)alkynyl;

the L birradical being bound to the backbone of the peptide sequence of formula (I) via X$_1$ and X$_3$ birradicals, or alternatively via X$_1$ and X$_5$ birradicals, or alternatively via X$_2$ and X$_4$ birradicals, or alternatively via X$_3$ and X$_6$ birradicals, the X birradicals which are bound to L birradical having the same or different meaning and being of formula (III):

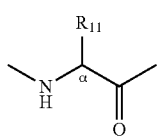

(III)

wherein
the L birradical binds to the X birradical of formula (III) via the alpha carbon atom;
R$_{11}$ is a monoradical selected from the group consisting of: (C$_1$-C$_{10}$)alkyl, (C$_2$-C$_{10}$)alkenyl, (C$_2$-C$_{10}$)alkynyl, (C$_1$-C$_{10}$)alkyl-O—(C$_1$-C$_{10}$)alkyl, (C$_1$-C$_{10}$)alkyl-C(=O)—(C$_1$-C$_{10}$)alkyl, (C$_1$-C$_{10}$)alkyl-O—C(O)—(C$_1$-C$_{10}$)alkyl, (C$_1$-C$_{10}$)alkyl-C(O)—NR$_8$—(C$_1$-C$_{10}$)alkyl, (C$_1$-C$_{10}$)alkyl-S—(C$_1$-C$_{10}$)alkyl, (C$_1$-C$_{10}$)alkyl-SR$_9$—(C$_1$-C$_{10}$)alkyl, (C$_1$-C$_{10}$)alkyl-S(=O)$_2$—(C$_1$-C$_{10}$)alkyl, (C$_1$-C$_{10}$)alkyl-S(=O)—(C$_1$-C$_{10}$)alkyl, (C$_1$-C$_{10}$)alkyl-O—S(=O)$_2$—O—(C$_1$-C$_{10}$)alkyl, (C$_1$-C$_{10}$)alkyl-NR$_{10}$—(C$_1$-C$_{10}$)alkyl, and a known ring system comprising from 3 to 14 carbon atoms, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—, and the other X birradicals of the backbone peptide sequence of formula (I), which are not bound to the "L" birradical, are the same or different and represent amino acids;

or, alternatively, when m, n, p, and q are 0, then X$_1$ to X$_6$ are the same or different and represent amino acids, provided that at least three of the radicals X$_1$ to X$_6$ are selected from the group consisting of:

X$_1$ represents an amino acid other than Glu,
X$_2$ represents an amino acid other than Lys,
X$_3$ represents an amino acid other than Ser,
X$_4$ represents an amino acid other than Phe,
X$_5$ represents an amino acid other than Ala, and
X$_6$ represents an amino acid other than Gln.

wherein:
the (C$_1$-C$_{10}$)alkyl, (C$_2$-C$_{10}$)alkenyl, and (C$_2$-C$_{10}$)alkynyl are non-substituted or substituted, "substituted (C$_1$-C$_{10}$)alkyl" means that the (C$_1$-C$_{10}$)alkyl is substituted by one or more radicals selected from the group consisting of:
halogen, —OR'$_{11}$, —NO$_2$, —NR'$_{11}$R$_{12}$, —SR'$_{11}$, —SO$_2$R'$_{11}$, —CO$_2$R'$_{11}$, and (C$_1$-C$_{10}$)alkyl-O—, being R'$_{11}$ and R$_{12}$ the same or different and selected from the group consisting of: —H, (C$_1$-C$_{10}$)alkyl, (C$_2$-C$_{10}$)alkenyl, and (C$_1$-C$_{10}$)alkynyl;

"substituted (C$_2$-C$_{10}$)alkenyl" means that the (C$_2$-C$_{10}$)alkenyl is substituted by one or more radicals selected from the group consisting of: halogen, —OR'$_{11}$, —NO$_2$, —NR'$_{11}$R$_{12}$, —SR'$_{11}$, —SO$_2$R'$_{11}$, —CO$_2$R'$_{11}$, and (C$_1$-C$_{10}$)alkyl-O—, being R'$_{11}$ and R$_{12}$ the same or different and selected from the group consisting of: —H, (C$_1$-C$_{10}$)alkyl, (C$_2$-C$_{10}$)alkenyl, and (C$_1$-C$_{10}$)alkynyl; and "substituted (C$_2$-C$_{10}$)alkynyl" means that the (C$_2$-C$_{10}$)alkynyl is substituted by one or more radicals selected from the group consisting of: halogen, —OR'$_{11}$, —NO$_2$, —NR'$_{11}$R$_{12}$, —SR'$_{11}$, —SO$_2$R'$_{11}$, —CO$_2$R'$_{11}$, and (C$_1$-C$_{10}$)alkyl-O—, being R'$_{11}$ and R$_{12}$ the same or different and selected from the group consisting of: —H, (C$_1$-C$_{10}$)alkyl, (C$_2$-C$_{10}$)alkenyl, and (C$_1$-C$_{10}$)alkynyl.

The present inventors have found that positions $X_1$ to $X_6$ and the "L" birradical (if present), are the responsible of conferring anticancer activity. But, in addition, the present inventors have found that $X_1$ to $X_6$ can confer high tumor-cell specificity and sensitivity.

As it is provided below, the peptides of the invention are highly specific, being capable of differentiating cancer from normal cells. In this regard, Table 5 below shows that the $EC_{50}$ values were substantially higher when the peptides of the invention were tested in JB healthy cells than when they were tested in tumor cells. These experimental data support the high specificity of the peptides of the invention against tumor cells, but also supports the fact that tumor cells are highly sensitive for the peptides of the invention. That is, it is achieved a strong inhibitory effect of the tumor cell growth when a very little amount of the peptide is given: the amount of peptide needed to achieve the same inhibitory effect is higher in healthy cells than in tumor cells.

In addition, the peptides of the invention have a substantially higher anti-cancer activity when compared with anticancer products already disclosed in the prior art (Table 5 below).

These data allow concluding that the peptides of formula (I) the invention are suitable as cancer therapeutics.

Wild-type sequence Asn Glu Leu Lys Arg Ser Phe Phe Ala Leu Arg Asp Gln (SEQ ID NO: 18 also referred as "L10") is inactive. The present inventors found that when a sequence (a) Gln-Arg-Arg or (b) Arg-Gln-Arg-Arg (SEQ ID NO: 20) was added in the N-terminal region of SEQ ID NO: 18, and a staple and a mutation were also made, the wild-type peptide became a remarkably active anticancer agent. As it is shown below, when only a staple was made in the wild-type sequence (SEQ ID NO: 4, also referred as "S13"), no activity was detected. The inventors also found that the remarkably anticancer effect was not only due to the incorporation of the sequence Gln-Arg-Arg or SEQ ID NO: 20 (and the mutation because as shown below: (a) when only sequence SEQ ID NO: 20 was added to the N-terminal of the wild-type sequence, the resulting peptide of sequence SEQ ID NO: 33 was inactive; (b) when SEQ ID NO: 20 was added to the N-terminal together with one or two mutations in the wild-type sequence, the resulting peptides of sequence SEQ ID NO: 19: (also referred as "L12") and SEQ ID NO: 32 (also referred as "L13"), respectively, were also inactive. Therefore, the data provided herein supports the fact that the incorporation of the sequence in the N-terminal region, a staple and one or more mutations in the wild-type sequence SEQ ID NO:18 confers a synergistic anticancer activity to the resulting peptide (SEQ ID NO: 2) and turns an inactive peptide into a potent anticancer peptide.

Therefore, it is also part of the first aspect of the invention a peptide of formula (I) or pharmaceutically salt thereof or an active metabolite thereof wherein "j" is 1, one of m, n, p, and q is 1 and the others is 0 (i.e., the peptide comprises one staple) and wherein one or more of the Xs radicals not bound to "L" birradical are selected from the group consisting of: $X_1$ represents an amino acid other than Glu, $X_2$ represents an amino acid other than Lys, $X_3$ represents an amino acid other than Ser, $X_4$ represents an amino acid other than Phe, $X_5$ represents an amino acid other than Ala, and $X_6$ represents an amino acid other than Gln, and it is of formula (Ibis4):

In a second aspect the present invention provides a peptide or a pharmaceutical salt thereof comprising the sequence of formula (IV):

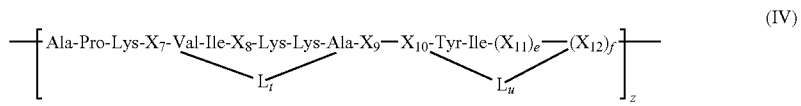

wherein
"t" and "u" are 0 or 1,
"e" and "f" are comprised from 0 to 10, and
z is comprised from 1 to 10, and
wherein
when one of "t" and "u" is 1, then
the other is 0,
L corresponds to a birradical of formula (II)

        (II)

"a" and "b" are the same or different and are 0 or 1;
"c" is comprised from 1 to 10;
$R_1$ and $R_3$ are birradicals independently selected from the group consisting of: $(C_1-C_{10})$alkyl, $(C_2-C_{10})$alkenyl, $(C_2-C_{10})$alkynyl, $(C_1-C_{10})$alkyl-O—$(C_1-C_{10})$alkyl, $(C_1-C_{10})$alkyl-C(=O)—$(C_1-C_{10})$alkyl, $(C_1-C_{10})$alkyl-O—C(O)—$(C_1-C_{10})$alkyl, $(C_1-C_{10})$alkyl-C(O)—$NR_8$—$(C_1-C_{10})$alkyl, $(C_1-C_{10})$alkyl-S—$(C_1-C_{10})$alkyl, $(C_1-C_{10})$alkyl-$SR_9$—$(C_1-C_{10})$alkyl, $(C_1-C_{10})$alkyl-S(=O)$_2$—$(C_1-C_{10})$alkyl, $(C_1-C_{10})$alkyl-S(=O)—$(C_1-C_{10})$alkyl, $(C_1-C_{10})$alkyl-O—S(=O)$_2$—O—$(C_1-C_{10})$alkyl, $(C_1-C_{10})$alkyl-$NR_{10}$—$(C_1-C_{10})$alkyl;
$R_2$ is a birradical selected from the group consisting of: O, C(=O), C(=O)$R_4$, C(=O)$NR_5$, C(=O)O, S(=O), S(=O)$_2$, S($R_6$), N($R_7$), $(C_1-C_{10})$alkyl, $(C_2-C_{10})$alkenyl, $(C_2-C_{10})$alkynyl, $NR_{13}R_{14}$, —NH—NH—, —N=N—, —S—S—, and a known ring system comprising from 3 to 14 carbon atoms, the system comprising from 1 to 3 rings, where:
  each one of the rings is saturated, partially unsaturated, or aromatic;
  the rings are isolated, partially or totally fused, each one of the members forming the known ring system is selected from the group consisting of: —CH—, —CH$_2$—, —NH—, —N—, —SH—, —S—, and —O—; and
  the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—;
$R_4$, $R_5$, $R_6$, $R_7$, $R_8$, $R_9$, $R_{13}$, $R_{10}$, and $R_{14}$ are monoradicals selected from the group consisting of: hydrogen, $(C_1-C_{10})$alkyl, $(C_2-C_{10})$alkenyl, and $(C_2-C_{10})$alkynyl;
when "a" and "b" are 0, or alternatively one of "a" and "b" is 0, then P and Q have a meaning different from $R_2$ radical, said P and Q birradicals being selected from the group consisting of: $(C_1-C_{10})$alkyl, $(C_2-C_{10})$alkenyl, and $(C_2-C_{10})$alkynyl; or, alternatively, when "a" and "b" are 0, or alternatively one of "a" and "b" is 0, then P and Q are C(=O) and $R_2$ is selected from the group consisting of: —O—, S($R_6$), N($R_7$), $(C_1-C_{10})$alkyl, $(C_2-C_{10})$alkenyl, $(C_2-C_{10})$alkynyl, $NR_{13}R_{14}$, —NH—NH—, —N=N—, —S—S—, and a known ring system comprising from 3 to 14 carbon atoms, the system comprising from 1 to 3 rings, where:
each one of the rings is saturated, partially unsaturated, or aromatic;
the rings are isolated, partially or totally fused, each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, $(C_1$-$C_{10})$alkyl, $(C_1-C_{10})$haloalkyl, and $(C_1-C_{10})$alkyl-O—; or, alternatively, when both "a" and "b", are 1, then P and Q are selected from the group consisting of: —S—, $(C_1-C_{10})$alkyl-S—, —NR'$_{10}$—, $(C_1-C_{10})$alkyl-NR'$_{10}$, —O—, $(C_1-C_{10})$-alkyl-O—, —C(=O), $(C_1-C_{10})$alkyl-C(=O)—, —C(=O)O, $(C_1-C_{10})$alkylC(=O)O—, C(=O)N—, $(C_1-C_{10})$alkylC(=O)—, C(=O)S— and $(C_1-C_{10})$alkyl-C(=O)S— being R'$_{10}$ a radical selected from the group consisting of: hydrogen, $(C_1-C_{10})$alkyl, $(C_2-C_{10})$alkenyl, and $(C_1-C_{10})$alkynyl;
the L birradical being bound to the backbone of the peptide sequence of formula (IV) via $X_7$ and $X_9$ birradicals, or alternatively via $X_{10}$ and $X_{12}$ birradicals,
the X birradicals which are bound to L birradical having the same or different meaning and being of formula (III):

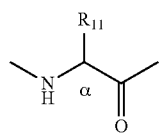

(III)

wherein
the L birradical binds to the X birradical of formula (III) via the alpha carbon atom;
$R_{11}$ is a monoradical selected from the group consisting of: $(C_1-C_{10})$alkyl, $(C_2-C_{10})$alkenyl, $(C_2-C_{10})$alkynyl, $(C_1-C_{10})$alkyl-O—$(C_1-C_{10})$alkyl, $(C_1-C_{10})$alkyl-C(=O)—$(C_1-C_{10})$alkyl, $(C_1-C_{10})$alkyl-O—C(O)— $(C_1-C_{10})$alkyl, $(C_1-C_{10})$alkyl-C(O)—NR$_8$—$(C_1-C_{10})$alkyl, $(C_1-C_{10})$alkyl-S—$(C_1-C_{10})$alkyl, $(C_1-C_{10})$alkyl-SR$_9$—$(C_1-C_{10})$alkyl, $(C_1-C_{10})$alkyl-S(=O)$_2$—$(C_1-C_{10})$alkyl, $(C_1-C_{10})$alkyl-S(=O)—$(C_1-C_{10})$alkyl, $(C_1-C_{10})$alkyl-O—S(=O)$_2$—O—$(C_1-C_{10})$alkyl, $(C_1-C_{10})$alkyl-NR$_{10}$—$(C_1-C_{10})$alkyl, and a known ring system comprising from 3 to 14 carbon atoms, the system comprising from 1 to 3 rings, where:
each one of the rings is saturated, partially unsaturated, or aromatic; the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—;
and the other X birradicals of the backbone peptide sequence of formula (I), which are not bound to the "L" birradical, are the same or different and represent amino acids;
or, alternatively,
when "t" and "u" are 0, then $X_7$ to $X_{12}$ are the same or different and represent amino acids, provided that at least three of them are selected from the group consisting of:
$X_7$ represents an amino acid other than Val,
$X_8$ represents an amino acid other than Leu,
$X_9$ represents an amino acid other than Thr, and
$X_{10}$ represents an amino acid other than Ala;
wherein:
the $(C_1-C_{10})$alkyl, $(C_2-C_{10})$alkenyl, and $(C_2-C_{10})$alkynyl are non-substituted or substituted,
"substituted $(C_1-C_{10})$alkyl" means that the $(C_1-C_{10})$alkyl is substituted by one or more radicals selected from the group consisting of:
halogen, —OR'$_{11}$, —NO$_2$, —NR'$_{11}R_{12}$, —SR'$_{11}$, —SO$_2$R'$_{11}$, —CO$_2$R'$_{11}$, and $(C_1-C_{10})$alkyl-O—, being R'$_{11}$ and R$_{12}$ the same or different and selected from the group consisting of: —H, $(C_1-C_{10})$alkyl, $(C_2-C_{10})$alkenyl, and $(C_1-C_{10})$alkynyl;
"substituted $(C_2-C_{10})$alkenyl" means that the $(C_2-C_{10})$alkenyl is substituted by one or more radicals selected from the group consisting of:
halogen, —OR'$_{11}$, —NO$_2$, —NR'$_{11}R_{12}$, —SR'$_{11}$, —SO$_2$R'$_{11}$, —CO$_2$R'$_{11}$, and $(C_1-C_{10})$alkyl-O—, being R'$_{11}$ and R$_{12}$ the same or different and selected from the group consisting of: —H, $(C_1-C_{10})$alkyl, $(C_2-C_{10})$alkenyl, and $(C_1-C_{10})$alkynyl; and
"substituted $(C_2-C_{10})$alkynyl" means that the $(C_2-C_{10})$alkynyl is substituted by one or more radicals selected from the group consisting of:
halogen, —OR'$_{11}$, —NO$_2$, —NR'$_{11}R_{12}$, —SR'$_{11}$, —SO$_2$R'$_{11}$, —CO$_2$R'$_{11}$, and $(C_1-C_{10})$alkyl-O—, being R'$_{11}$ and R$_{12}$ the same or different and selected from the group consisting of: —H, $(C_1-C_{10})$alkyl, $(C_2-C_{10})$alkenyl, and $(C_1-C_{10})$alkynyl.

The present inventors have found that positions $X_7$ to $X_{10}$ and the "L" birradical (if present), are the responsible of conferring anticancer activity. But, in addition, the present inventors have found that $X_7$ to $X_{10}$ and L can confer high tumor-cell specificity and sensitivity.

As it is provided below, the peptides of the invention are highly specific, being capable of differentiating cancer from normal cells. In this regard, Table 6 below shows that the EC$_{50}$ values were substantially higher when the peptides of the invention were tested in JB healthy cells than when they were tested in tumor cells. These experimental data support the high specificity of the peptides of the invention against tumor cells, but also supports the fact that tumor cells are highly sensitive for the peptides of the invention. That is, it is achieved a strong inhibitory effect of the tumor cell growth when a very little amount of the peptide is given: the amount of peptide needed to achieve the same inhibitory effect is higher in healthy cells than in tumor cells.

In addition, the peptides of the invention have a substantially higher anti-cancer activity when compared with anti-cancer products already disclosed in the prior art (Table 6 below).

In addition, the data provided in Table 11, allows concluding that the peptides of the invention show an appropriate half-life time in plasma.

These data allow concluding that the peptides of formula (IV) of the invention are suitable as cancer therapeutics.

It is also part of the second aspect of the invention a peptide or pharmaceutically salt thereof of formula (IVbis3), wherein "t" is 1, "u" is 0, $X_8$ represents Leu, and $X_{10}$ represents Ala:

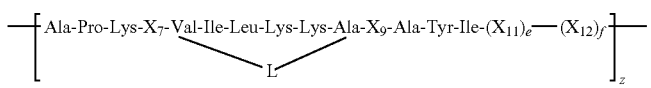

(IVbis3)

As it is illustrated below, the wild type sequence (SEQ ID NO: 21=Pro-Lys-Val-Val-Ile-Leu-Lys-Lys-Ala-Thr-Ala-Tyr-Ile, also referred as "L14a") is inactive. The present inventors have surprisingly found, however, that the peptide can be made active as anticancer agent, when a Ala residue is added at the N-terminal end, a staple "L" at the particular position shown in formula (IVbis3), and two extra amino acid residues at the C-terminal end are added. It is the first time that it is provided experimental data showing that sequence SEQ ID NO: 21 can be made active by adding a staple between the third and the tenth amino acids.

A further aspect of the invention is a peptide of formula (VIII) or a pharmaceutical salt thereof:

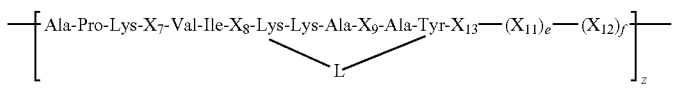

(VIII)

wherein:

"e" and "f" are 1, and z is comprised from 1 to 10, and

L corresponds to a birradical of formula (II)

"a" and "b" are the same or different and are 0 or 1;

"c" is comprised from 1 to 10;

$R_1$ and $R_3$ are birradicals independently selected from the group consisting of: $(C_1\text{-}C_{10})$alkyl, $(C_2\text{-}C_{10})$alkenyl, $(C_2\text{-}C_{10})$alkynyl, $(C_1\text{-}C_{10})$alkyl-O—$(C_1\text{-}C_{10})$alkyl, $(C_1\text{-}C_{10})$alkyl-C(=O)—$(C_1\text{-}C_{10})$alkyl, $(C_1\text{-}C_{10})$alkyl-O—C(O)—$(C_1\text{-}C_{10})$alkyl, $(C_1\text{-}C_{10})$alkyl-C(O)—$NR_8$—$(C_1\text{-}C_{10})$alkyl, $(C_1\text{-}C_{10})$alkyl-S—$(C_1\text{-}C_{10})$alkyl, $(C_1\text{-}C_{10})$alkyl-$SR_9$—$(C_1\text{-}C_{10})$alkyl, $(C_1\text{-}C_{10})$alkyl-S$(=O)_2$—$(C_1\text{-}C_{10})$alkyl, $(C_1\text{-}C_{10})$alkyl-S(=O)—$(C_1\text{-}C_{10})$alkyl, $(C_1\text{-}C_{10})$alkyl-O—S$(=O)_2$—O—$(C_1\text{-}C_{10})$alkyl, $(C_1\text{-}C_{10})$alkyl-$NR_{10}$—$(C_1\text{-}C_{10})$alkyl;

$R_2$ is a birradical selected from the group consisting of: O, C(=O), C(=O)$R_4$, C(=O)$NR_5$, C(=O)O, S(=O), S$(=O)_2$, S($R_6$), N($R_7$), $(C_1\text{-}C_{10})$alkyl, $(C_2\text{-}C_{10})$alkenyl, $(C_2\text{-}C_{10})$alkynyl, $NR_{13}R_{14}$, —NH—NH—, —N=N—, —S—S—, and a known ring system comprising from 3 to 14 carbon atoms, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of: halogen, —OH, —NO$_2$, $(C_1\text{-}C_{10})$alkyl, $(C_1\text{-}C_{10})$haloalkyl, and $(C_1\text{-}C_{10})$alkyl-O—;

$R_4$, $R_5$, $R_6$, $R_7$, $R_8$, $R_9$, $R_{13}$, $R_{10}$, and $R_{14}$ are monoradicals selected from the group consisting of: hydrogen, $(C_1\text{-}C_{10})$alkyl, $(C_2\text{-}C_{10})$alkenyl, and $(C_2\text{-}C_{10})$alkynyl;

when "a" and "b" are 0, or alternatively one of "a" and "b" is 0, then P and Q have a meaning different from $R_2$ radical, said P and Q birradicals being selected from the group consisting of: $(C_1\text{-}C_{10})$alkyl, $(C_2\text{-}C_{10})$alkenyl, and $(C_2\text{-}C_{10})$alkynyl; or, alternatively, when "a" and "b" are 0, or alternatively one of "a" and "b" is 0, then P and Q are C(=O) and $R_2$ is selected from the group consisting of: —O—, S($R_6$), N($R_7$), $(C_1\text{-}C_{10})$alkyl, $(C_2\text{-}C_{10})$alkenyl, $(C_2\text{-}C_{10})$alkynyl, $NR_{13}R_{14}$, —NH—NH—, —N=N—, —S—S—, and a known ring system comprising from 3 to 14 carbon atoms, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1\text{-}C_{10})$alkyl, $(C_1\text{-}C_{10})$haloalkyl, and $(C_1\text{-}C_{10})$alkyl-O—; or, alternatively, when both "a" and "b", are 1, then P and Q are selected from the group consisting of: —S—, $(C_1\text{-}C_{10})$alkyl-S—, —NR'$_{10}$—, $(C_1\text{-}C_{10})$alkyl-NR'$_{10'}$, —O—, $(C_1\text{-}C_{10})$-alkyl-O—, —C(=O), $(C_1\text{-}C_{10})$alkyl-C(=O)—, —(C(=O)O, $(C_1\text{-}C_{10})$alkylC(=O)O—, C(=O)N—, $(C_1\text{-}C_{10})$alkylC(=O)—, C(=O)S— and $(C_1\text{-}C_{10})$alkyl-C(=O)S— being R'$_{10}$ a radical selected from the group consisting of: hydrogen, $(C_1\text{-}C_{10})$alkyl, $(C_2\text{-}C_{10})$alkenyl, and $(C_1\text{-}C_{10})$alkynyl;

the L birradical being bound to the backbone of the peptide sequence of formula (IV) via $X_8$ and $X_{13}$ birradicals, $X_8$ and $X_{13}$ have the same or different meaning and are of formula (III):

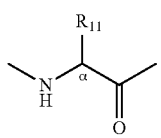

wherein
- the L birradical binds to the X birradical of formula (III) via the alpha carbon atom;
- $R_{11}$ is a monoradical selected from the group consisting of: $(C_1\text{-}C_{10})$alkyl, $(C_2\text{-}C_{10})$alkenyl, $(C_2\text{-}C_{10})$alkynyl, $(C_1\text{-}C_{10})$alkyl-O—$(C_1\text{-}C_{10})$alkyl, $(C_1\text{-}C_{10})$alkyl-C(=O)—$(C_1\text{-}C_{10})$alkyl, $(C_1\text{-}C_{10})$alkyl-O—C(O)—$(C_1\text{-}C_{10})$alkyl, $(C_1\text{-}C_{10})$alkyl-C(O)—$NR_8$—$(C_1\text{-}C_{10})$alkyl, $(C_1\text{-}C_{10})$alkyl-S—$(C_1\text{-}C_{10})$alkyl, $(C_1\text{-}C_{10})$alkyl-$SR_9$—$(C_1\text{-}C_{10})$alkyl, $(C_1\text{-}C_{10})$alkyl-S(=O)$_2$—$(C_1\text{-}C_{10})$alkyl, $(C_1\text{-}C_{10})$alkyl-S(=O)—$(C_1\text{-}C_{10})$alkyl, $(C_1\text{-}C_{10})$alkyl-O—S(=O)$_2$—O—$(C_1\text{-}C_{10})$alkyl, $(C_1\text{-}C_{10})$alkyl-$NR_{10}$—$(C_1\text{-}C_{10})$alkyl, and a known ring system comprising from 3 to 14 carbon atoms, the system comprising from 1 to 3 rings, where:
- each one of the rings is saturated, partially unsaturated, or aromatic;
  - the rings are isolated, partially or totally fused, each one of the members forming the known ring system is selected from the group consisting of: —CH—, —CH$_2$—, —NH—, —N—, —SH—, —S—, and —O—; and
  - the ring system is optionally substituted by one or more radicals independently selected from the group consisting of halogen, —OH, —NO$_2$, $(C_1\text{-}C_{10})$alkyl, $(C_1\text{-}C_{10})$haloalkyl, and $(C_1\text{-}C_{10})$alkyl-O—;
- $X_7$ represents an amino acid other than Val;
- $X_9$ represents an amino acid other than Thr; and
- $X_{11}$ and $X_{12}$ represent any amino acid.

In a further aspect, the present invention provides a metabolite resulting from the hydrolysis of any of the peptides of the invention (either of the first or second aspect as well as of the peptide of formula (VIII)).

The metabolite of the invention lacks from 1 to 3 amino acid in the C-terminal region of the peptides of the invention and 1 amino acid of the N-terminal region.

In a further aspect, the present invention provides a protein fusion comprising the peptide of the invention.

In a third aspect, the present invention provides a veterinary or pharmaceutical composition comprising a therapeutically effective amount of the peptide or a pharmaceutical salt thereof as defined in the first or second aspect of the invention, or the peptide or pharmaceutical salt thereof of formula (VIII), or a metabolite of any of the peptides of the invention or the fusion protein of the invention, together with acceptable veterinary or pharmaceutical excipients and/or carriers.

In a fourth aspect, the present invention provides the peptide or a pharmaceutical salt thereof as defined in the first or second aspect of the invention, as well as the peptide or pharmaceutical salt thereof of formula (VIII), or the metabolite of any of the peptides of the invention or the fusion protein of the invention for use as a medicament. This aspect can be alternatively formulated as the use of a peptide or a pharmaceutical salt thereof as defined in the first or second aspect of the invention, or as defined in formula (VIII), or of a metabolite of a peptide of the invention, or of a fusion protein of the invention, in the manufacture of a medicament for the treatment of a disease. This aspect can also be alternatively formulated as a method for the treatment of a disease, the method comprising administering an effective therapeutic amount of a peptide or a pharmaceutical salt thereof, as defined in any of the first or second aspects of the invention, or as defined in formula (VIII), or of a metabolite of a peptide of the invention, or of a fusion protein of the invention, to a subject in need thereof.

In a fifth aspect, the present invention provides the peptide or a pharmaceutical salt thereof as defined in the first or second aspect of the invention, the peptide or pharmaceutical salt thereof of formula (VIII), or the metabolite of the invention, or the fusion protein of the invention for use in the treatment of cancer. This aspect can alternatively be formulated as the use of a peptide or a pharmaceutical salt thereof as defined in the first or second aspect of the invention or of a peptide or pharmaceutical salt thereof of formula (VIII), or of the metabolite of the invention, or of the fusion protein of the invention in the manufacture of a medicament for the treatment of cancer. This aspect can also be alternatively formulated as a method for the treatment of cancer, the method comprising administering an effective therapeutic amount of a peptide or a pharmaceutical salt thereof as defined in any of the first or second aspects of the invention or of a peptide or pharmaceutical salt thereof of formula (VIII), or of a metabolite of the invention, or of a fusion protein of the invention, to a subject in need thereof.

BRIEF DESCRIPTION OF DRAWINGS

FIG. 1 represents a bar-graph wherein fluorescence data are provided after a caspase 3-7 activation assay in MM.1S cells after treatment with two peptides of the invention (the so-called "S04" and "S09"). The amount of fluorescence is compared with the one detected in the untreated cells (control). The p value reported indicates the result of the t-test calculated for the significant difference between the values.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For the purposes of the present invention, any ranges given include both the lower and the upper end-points of the range.

The present invention provides polypeptides comprising sequences of formula (I) or (IV) as it has been stated above.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, and ammonium. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate and aryl sulfonate.

The term $(C_1-C_{10})$alkyl refers to a saturated straight or branched alkyl chain having from 1 to 10 carbon atoms. Illustrative non-limitative examples are: methyl, ethyl, propyl, isopropyl, butyl, isobutyl, sec-butyl, tert-butyl, n-pentyl, neo-pentyl and n-hexyl.

The term $(C_1-C_{20})$alkyl refers to a saturated straight or branched alkyl chain having from 1 to 20 carbon atoms.

The term $(C_2-C_{10})$alkenyl refers to a saturated straight, or branched alkyl chain containing from 2 to 10 carbon atoms and also containing one or more double bonds. Illustrative non-limitative examples are ethenyl, propenyl, butenyl, 1-methyl-2-buten-1-yl, and the like.

The term $(C_2-C_{10})$alkynyl refers to a saturated straight, or branched alkyl chain containing from 2 to 20 carbon atoms and also containing one or more triple bonds. Examples include, among others, ethynyl, 1-propynyl, 2-butynyl, 1,3-butadinyl, 4-pentynyl, and 1-hexynyl.

The term $(C_1-C_{10})$haloalkyl refers to a group resulting from the replacement of one or more hydrogen atoms from a $(C_1-C_{10})$alkyl group with one or more, preferably from 1 to 6, halogen atoms, which can be the same or different. Examples include, among others, trifluoromethyl, fluoromethyl, 1-chloroethyl, 2-chloroethyl, 1-fluoroethyl, 2-fluoroethyl, 2-bromoethyl, 2-iodoethyl, 2,2,2-trifluoroethyl, pentafluoroethyl, 3-fluoropropyl, 3-chloropropyl, 2,2,3,3-tetrafluoropropyl, 2,2,3,3,3-pentafluoropropyl, heptafluoropropyl, 4-fluorobutyl, and nonafluorobutyl.

The term "halogen" refers to the group in the periodic table consisting of five chemically related elements: fluorine (F), chlorine (Cl), bromine (Br), iodine (I), and astatine (At).

The term "amino acid" refers to a molecule containing both an amino group and a carboxyl group. Unless otherwise explicitly stated, the amino acid can have L- or D-configuration. Amino acids can be classified by the side chain group. There are basically four different classes of amino acids determined by different side chains: (1) non-polar, (2) polar and neutral (uncharged polar), (3) acidic and polar (hereinafter also referred as "acid" or "acidic" amino acids), (4) basic and polar (hereinafter also referred as "basic" amino acids).

Non-polar amino acids have side chains which are hydrocarbon alkyl groups (alkane branches) or aromatic (benzene rings) or heteroaromatic (e.g. indole ring). Illustrative non-limitative examples of common non-polar amino acids are Ala, Val, Leu, Ile, Pro, Trp, Gly, Phe, and Met. Polar-neutral amino acids have polar but not charged groups at neutral pH in the side chain (such as hydroxyl, amide or thiol groups). Illustrative non-limitative examples of polar neutral amino acids are Ser, Thr, Cys, Tyr, Asn, and Gln.

In certain embodiments, an amino acid is an alpha amino acid. Suitable amino acids include, without limitation, natural alpha-amino acids such as L-isomers of the 20 common naturally occurring alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; natural beta-amino acids (e.g., beta-alanine); and unnatural amino acids.

TABLE 1

| Exemplary unnatural alpha-amino acids | Suitable amino acid side chains | |
|---|---|---|
| | R | R' |
| D-Alanine | —H | —CH$_3$ |
| D-Arginine | —H | —CH$_2$CH$_2$CH$_2$—NHC(=NH)NH$_2$ |
| D-Asparagine | —H | —CH$_2$C(=O)NH$_2$ |
| D-Aspartic acid | —H | —CH$_2$CO$_2$H |
| D-Cysteine | —H | —CH$_2$SH |
| D-Glutamic acid | —H | —CH$_2$CH$_2$CO$_2$H |
| D-Glutamine | —H | —CH$_2$CH$_2$C(=O)NH$_2$ |
| D-Histidine | —H | —CH$_2$-2-(1H-imidazole) |
| D-Isoleucine | —H | -sec-butyl |
| D-Leucine | —H | -iso-butyl |
| D-Lysine | —H | —CH$_2$CH$_2$CH$_2$CH$_2$NH$_2$ |
| D-Methionine | —H | —CH$_2$CH$_2$SCH$_3$ |
| D-Phenylalanine | —H | —CH$_2$Ph |
| D-Proline | —H | -2-(pyrrolidine) |
| D-Serine | —H | —CH$_2$OH |
| D-Threonine | —H | —CH$_2$CH(OH)(CH$_3$) |
| D-Tryptophan | —H | —CH$_2$-3-(1H-indole) |
| D-Tyrosine | —H | —CH$_2$-(p-hydroxyphenyl) |
| D-Valine | —H | -isopropyl |
| Di-vinyl | —CH=CH$_2$ | —CH=CH$_2$ |
| Exemplary unnatural alpha-amino acids | | R and R' are equal to: |
| α-methyl-Alanine (Aib) | —CH$_3$ | —CH$_3$ |
| α-methyl-Arginine | —CH$_3$ | —CH$_2$CH$_2$CH$_2$—NHC(=NH)NH$_2$ |
| α-methyl-Asparagine | —CH$_3$ | —CH$_2$C(=O)NH$_2$ |
| α-methyl-Aspartic acid | —CH$_3$ | —CH$_2$CO$_2$H |
| α-methyl-Cysteine | —CH$_3$ | —CH$_2$SH |
| α-methyl-Glutamic acid | —CH$_3$ | —CH$_2$CH$_2$CO$_2$H |
| α-methyl-Glutamine | —CH$_3$ | —CH$_2$CH$_2$C(=O)NH$_2$ |
| α-methyl-Histidine | —CH$_3$ | —CH$_2$-2-(1H-imidazole) |
| α-methyl-Isoleucine | —CH$_3$ | -sec-butyl |
| α-methyl-Leucine | —CH$_3$ | -iso-butyl |
| α-methyl-Lysine | —CH$_3$ | —CH$_2$CH$_2$CH$_2$CH$_2$NH$_2$ |

TABLE 2

| | unnatural amino acids |
|---|---|
| Aad | 2-Aminoadipic acid |
| bAad | 3-Aminoadipic acid |
| bAla | beta-Alanine, beta-Aminopropionic acid |
| Abu | 2-Aminobutyric acid |
| 4Abu | 4-Aminobutyric acid, piperidinic acid |

TABLE 2-continued unnatural amino acids

| | |
|---|---|
| Acp | 6-Aminocaproic acid |
| Ahe | 2-Aminoheptanoic acid |
| Aib | 2-Aminoisobutyric acid |
| bAib | 3-Aminoisobutyric acid |
| Apm | 2-Aminopimelic acid |
| Dbu | 2,4 Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | allo-Hydroxylysine |
| 3Hyp | 3-Hydroxyproline |
| 4Hyp | 4-Hydroxyproline |
| Ide | Isodesmosine |
| aIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Amino acids used in the construction of peptides of the present invention may be prepared by organic synthesis, or obtained by other routes, such as, for example, degradation of or isolation from a natural source.

There are many known unnatural amino acids any of which may be included in the peptides of the present invention (some of them are listed in Table 2 above). Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; —CH$_3$), disubstituted phenylalanines, substituted tyrosines (e.g., further substituted with —C(=O)C$_6$H$_5$; —CF$_3$; —CN; -halo; —NO$_2$; —CH$_3$), and statine. Additionally, the amino acids suitable for use in the present invention may be derivatized to include amino acid residues that are hydroxylated, phosphorylated, sulfonated, acylated, lipidated, and glycosylated, to name a few.

The term "known" ring system as used herein refers to a ring system which is chemically feasible and is known in the art and so intends to exclude those ring systems that are not chemically possible.

According to the present invention when the ring system is formed by "isolated" rings means that the ring system is formed by two, three or four rings and said rings are bound via a bond from the atom of one ring to the atom of the other ring. The term "isolated" also embraces the embodiment in which the ring system has only one ring. Illustrative non-limitative examples of known ring systems consisting of one ring are those derived from: cyclopropyl, cyclobutyl, cyclopentyl, cyclhexyl, cycloheptyl, cyclopropenyl, cyclobutenyl, cyclopentenyl, phenyl, and cycloheptenyl.

According to the present invention when the ring system has rings "totally fused", means that the ring system is formed by two, three or four rings in which two or more atoms are common to two adjoining rings. Illustrative non-limitative examples are 1,2,3,4-tetrahydronaphthyl, 1-naphthyl, 2-naphthyl, anthryl, or phenanthryl.

According to the present invention when the ring system is "partially fused" it means that the ring system is formed by three or four rings, being at least two of said rings totally fused (i.e. two or more atoms being common to the two adjoining rings) and the remaining ring(s) being bound via a bond from the atom of one ring to the atom of one of the fused rings.

In one embodiment of the first aspect of the invention, the peptide or pharmaceutical salt thereof is one wherein v is 1.

In another embodiment of the first aspect of the invention, the peptide or pharmaceutical salt is one wherein when v is 1, then: (a) the C-terminal group of the peptide corresponds to a —C(O)R$_{15}$, wherein R$_{15}$ is a radical selected from the group consisting of: —OR$_{16}$, —NR$_{17}$R$_{18}$, —O(C$_1$-C$_{20}$)alkylC(O)OR$_{19}$, —O(C$_1$-C$_{20}$)alkylC(O)R$_{20}$, —O(C$_1$-C$_{20}$)alkylOR$_{21}$, —(C$_1$-C$_{20}$)C(O)NR$_{22}$R$_{23}$, or a polymer, such as a polyol, such as polyethylene glycol (PEG) being R$_{15}$, R$_{16}$, R$_{17}$, R$_{18}$, R$_{19}$, R$_{20}$, R$_{21}$, R$_{22}$ and R$_{23}$ radicals selected from the group consisting of: hydrogen, (C$_1$-C$_{10}$)alkyl, (C$_2$-C$_{10}$)alkenyl, (C$_2$-C$_{10}$)alkenyl, and a known ring system comprising from 3 to 14 carbon atoms, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—;

and (b) the N-terminal group is selected from —NR$_{24}$R$_{25}$, —NHC(O)R$_{26}$, and a N-fluorophore moiety, wherein R$_{24}$ and R$_{25}$ are independently selected from the group consisting of: hydrogen, (C$_1$-C$_{10}$)alkyl, (C$_2$-C$_{10}$)alkenyl, (C$_2$-C$_{10}$)alkynyl and a known ring system comprising from 3 to 14 carbon atoms, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—;

and R$_{26}$ is a radical selected from —OR$_{27}$, —(C$_1$-C$_{20}$)alkylC(O)OR$_{28}$, —(C$_1$-C$_{20}$)alkylC(O)R$_{29}$, —(C$_1$-C$_{20}$)alkylOR$_{30}$, and —O(C$_1$-C$_{20}$)CONR$_{31}$R$_{32}$, wherein R$_{27}$ to R$_{32}$ are radicals independently selected from hydrogen, (C$_1$-C$_{10}$)alkyl, (C$_2$-C$_{10}$)alkenyl, and (C$_2$-C$_1$)alkenyl and a known ring system comprising from 3 to 14 carbon atoms, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$) haloalkyl, and (C$_1$-C$_{10}$)alkyl-O—.

In one embodiment, the C-terminal group is —COOH and the N-terminal group is —NH$_2$. In another embodiment, the C-terminal group is —CO—NH$_2$ and the N-terminal group is —NHC(O)R$_{26}$, being R$_{26}$ as defined above. In another embodiment, the C-terminal group is —CO—NH$_2$ and the N-terminal group is —NHC(O)R$_{26}$, being R$_{26}$ a radical —(C$_1$-C$_{20}$)alkylC(O)OR$_{28}$. In another embodiment, the C-terminal group is —CO—NH$_2$ and the N-terminal group is —NHC(O)R$_{26}$, being R$_{26}$ a radical —(CH$_2$)$_2$C(O)OH (i.e., succinyl). In one embodiment, v is 1, the C-terminal group is —COOH and the N-terminal group is a —NH$_2$. In another embodiment, v is 1, the C-terminal group is —CO—NH$_2$ and the N-terminal group is —NHC(O)R$_{26}$, being R$_{26}$ as defined above. In another embodiment, v is 1, the C-terminal group is —CO—NH$_2$ and the N-terminal group is —NHC(O)R$_{26}$, being R$_{26}$ a radical —(C$_1$-C$_{20}$)alkylC(O) OR$_{28}$. In another embodiment, v is 1, the C-terminal group is —CO—NH$_2$ and the N-terminal group is —NHC(O)R$_{26}$, being R$_{26}$ a radical —(CH$_2$)$_2$C(O)OH (i.e., succinyl).

Also are part of the present invention, therefore, the peptides provided in any of the embodiments hereinafter, either having free amino and/or carboxy end groups or can have them derivatized as explained in detail above.

In another embodiment of the first aspect of the invention, the peptide or pharmaceutical salt is one wherein j is 1 and is of formula (Ibis1):

All the embodiments provided above or below for the peptide or pharmaceutical salt thereof of formula (I) also applies for those of formula (Ibis1), (Ibis2) and (Ibis3).

In another embodiment of the first aspect of the invention, the peptide or pharmaceutical salt thereof of formula (I) is one wherein one of "m", "n", "p", and "q" is 1 and the others are 0, being L and radicals X$_1$ to X$_6$ as defined above or below.

As it has been mentioned above, the present inventors have surprisingly found that (1) adding a sequence selected from (a) Gln-Arg-Arg or (b) SEQ ID NO: 20 in the N-terminal, (2) changing an amino acid by another, and (3) including a L birradical (staple), the wild type sequence SEQ ID NO: 18, which is inactive, becomes a remarkable anticancer peptide.

In view of the above, in a preferred embodiment of the first aspect of the invention, the peptide or pharmaceutical salt thereof of formula (I) is one wherein one of "m", "n", and "q" is 1. In another embodiment of the first aspect of the invention, the peptide or pharmaceutical salt thereof of formula (I) is one wherein one of "m", "n", "p", and "q" is 1, and the X birradicals of the backbone peptide sequence of formula (I), which are not bound to the "L" birradical, are amino acids, provided that at least one of them is selected from the group consisting of:

X$_1$ represents an amino acid other than Glu,
X$_2$ represents an amino acid other than Lys,
X$_3$ represents an amino acid other than Ser,
X$_4$ represents an amino acid other than Phe,
X$_5$ represents an amino acid other than Ala, and
X$_6$ represents an amino acid other than Gln.

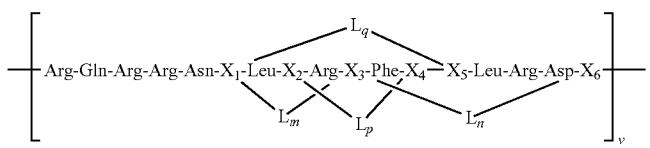

(Ibis1)

In another embodiment of the first aspect of the invention, v and j are 1, thus the peptide of the first aspect of the invention being one of formula (Ibis2):

In this way, in the peptide of formula (I), (Ibis1), (Ibis2), or (Ibis3) or a pharmaceutical salt thereof, when "m" is 1, the X's birradicals not bound to the backbone of the peptide

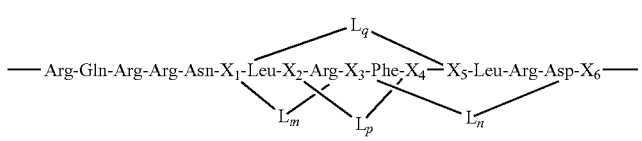

(Ibis2)

In another embodiment of the first aspect of the invention, v and j are 1, thus the peptide of the first aspect of the invention being one of formula (Ibis3):

are X$_2$, X$_4$, X$_5$ and X$_6$, at least one of them being selected from the group: X$_2$ represents an amino acid other than Lys, X$_4$ represents an amino acid other than Phe, X$_5$ represents an amino acid other than Ala, and X$_6$ represents an amino acid other than Gln. Alternatively, in the peptide of formula (I), (Ibis1), (Ibis2), or (Ibis3) or a pharmaceutical salt thereof, when "n" is 1, the X's birradicals not bound to the backbone of the peptide are X$_1$, X$_2$, X$_4$ and X$_5$, at least one of them being selected from the group: X$_1$ represents an amino acid other than Glu, X$_2$ represents an amino acid other than Lys, X$_4$ represents an amino acid other than Phe, and X$_5$ represents an amino acid other than Ala. Alternatively, in the

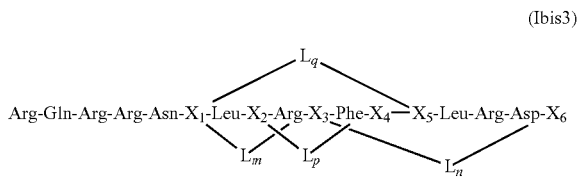

(Ibis3)

peptide of formula (I), (Ibis1), (Ibis2), or (Ibis3) or a pharmaceutical salt thereof, when "p" is 1, the X's birradicals not bound to the backbone of the peptide are $X_1$, $X_3$, $X_5$ and $X_6$, at least one of them being selected from the group: $X_1$ represents an amino acid other than Glu, $X_3$ represents an amino acid other than Ser, $X_5$ represents an amino acid other than Ala, and $X_6$ represents an amino acid other than Gln. And alternatively in the peptide of formula (I), (Ibis1), (Ibis2), or (Ibis3) or a pharmaceutical salt thereof, when "q" is 1, the X's birradicals not bound to the backbone of the peptide are $X_2$, $X_3$, $X_4$ and $X_6$, at least one of them being selected from the group: $X_2$ represents an amino acid other than Lys, $X_3$ represents an amino acid other than Ser, $X_4$ represents an amino acid other than Phe, and $X_6$ represents an amino acid other than Gln.

In another embodiment of the first aspect of the invention, the peptide or pharmaceutical salt thereof of formula (I) is one wherein one of "m", "n", and "q" is 1. In another embodiment of the first aspect of the invention, the peptide or pharmaceutical salt thereof of formula (I) is one wherein one of "m", "n", and "q" is 1, and the X birradicals of the backbone peptide sequence of formula (I), which are not bound to the "L" birradical are D-amino acids, provided that at least one of them is selected from the group consisting of:
$X_1$ represents a D-amino acid other than D-Glu,
$X_2$ represents a D-amino acid other than D-Lys,
$X_3$ represents a D-amino acid other than D-Ser,
$X_4$ represents a D-amino acid other than D-Phe,
$X_5$ represents a D-amino acid other than D-Ala, and
$X_6$ represents a D-amino acid other than D-Gln.

In another embodiment of the first aspect of the invention, L corresponds to a birradical of formula (II) wherein one of "a" and "b" are 0. In another embodiment of the first aspect of the invention, L corresponds to a birradical of formula (II) wherein "a" and "b" are 0. In another embodiment of the first aspect of the invention, L corresponds to a birradical of formula (II) wherein "c" is comprised from 1 to 6. In another embodiment of the first aspect of the invention, L corresponds to a birradical of formula (II) wherein "c" is 1. In another embodiment of the first aspect of the invention, L corresponds to a compound of formula (II) wherein:
"a" and "b" are 0; and
"c" is 1.

In another embodiment of the first aspect of the invention, L corresponds to a birradical of formula (II) wherein P and Q are the same or different and represent a $(C_1-C_{10})$alkyl. In another embodiment of the first aspect of the invention, L corresponds to a birradical of formula (II) wherein:
"a" and "b" are 0;
"c" is 1; and
P and Q are the same or different and represent a $(C_1-C_{10})$alkyl.

In another embodiment of the first aspect of the invention $R_2$ is selected from the group consisting of: $(C_1-C_{10})$alkyl, $(C_2-C_{10})$alkenyl, $(C_2-C_{10})$alkenyl, and a known ring system comprising from 3 to 14 carbon atoms, the system comprising from 1 to 3 rings, where:
each one of the rings is saturated, partially unsaturated, or aromatic;
the rings are isolated, partially or totally fused, each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the first aspect of the invention, $R_2$ is $(C_2-C_{10})$alkenyl. In another embodiment of the first aspect of the invention, $R_2$ is ethylene.

In another embodiment of the first aspect of the invention, the peptide of formula (I), (Ibis1), (Ibis2), (Ibis3) or a pharmaceutical salt thereof, is one wherein L corresponds to a birradical of formula (II) wherein "a" and "b" are 0; "c" is 1; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where:
each one of the rings is saturated, partially unsaturated, or aromatic;
the rings are isolated, partially or totally fused, each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the first aspect of the invention, the peptide of formula (I), (Ibis1), (Ibis2), (Ibis3) or a pharmaceutical salt thereof, is one wherein L corresponds to a birradical of formula (II) wherein "a" and "b" are 0, "c" is 1; and $R_2$ is $(C_2-C_{10})$alkenyl. In another embodiment of the first aspect of the invention, the peptide of formula (I), (Ibis1), (Ibis2) or (Ibis3) or a pharmaceutical salt thereof, is one wherein L corresponds to a birradical of formula (II) wherein "a" and "b" are 0, "c" is 1, and $R_2$ is ethylene.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where:
each one of the rings is saturated, partially unsaturated, or aromatic;
the rings are isolated, partially or totally fused, each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the first aspect of the invention, the peptide of formula (I), (Ibis1), (Ibis2) or (Ibis3) or a pharmaceutical salt thereof, is one wherein L corresponds to a birradical of formula (II) wherein P and Q are the same or different and represent a $(C_1-C_1)$alkyl; and $R_2$ is $(C_2-C_{10})$alkenyl. In another embodiment of the first aspect of the invention, the peptide of formula (I), (Ibis1), (Ibis2) or (Ibis3) or a pharmaceutical salt thereof, is one wherein L corresponds to a birradical of formula (II) wherein P and Q are the same or different and represent a $(C_1-C_{10})$alkyl, and $R_2$ is ethylene.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein:
"a" and "b" are 0;
"c" is 1;
P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl and a known ring system comprising from 3 to 14 carbon atoms, the system comprising from 1 to 3 rings, where:
each one of the rings is saturated, partially unsaturated, or aromatic; the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein:
"a" and "b" are 0;
"c" is 1;
P and Q are the same or different and represent a $(C_1-C_{10})$alkyl; and
$R_2$ is $(C_2-C_{10})$alkenyl.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein:
"a" and "b" are 0;
"c" is 1;
P and Q are the same or different and represent a $(C_1-C_{10})$alkyl; and
$R_2$ is ethylene.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein "a" and "b" are 0; "c" is 1; $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where:
each one of the rings is saturated, partially unsaturated, or aromatic;
the rings are isolated, partially or totally fused, each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—; and the X birradicals of the backbone peptide sequence of formula (I), which are not bound to the "L" birradical, are amino acids, provided that at least one of them is selected from the group consisting of:
$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein "a" and "b" are 0, "c" is 1; $R_2$ is $(C_2-C_{10})$alkenyl; and the X birradicals of the backbone peptide sequence of formula (I), which are not bound to the "L" birradical, are amino acids, provided that at least one of them is selected from the group consisting of:

$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein "a" and "b" are 0, "c" is 1, $R_2$ is ethylene; and the X birradicals of the backbone peptide sequence of formula (I), which are not bound to the "L" birradical, are amino acids, provided that at least one of them is selected from the group consisting of:
$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein P and Q are the same or different and represent a $(C_1-C_{10})$alkyl; $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where:
each one of the rings is saturated, partially unsaturated, or aromatic;
the rings are isolated, partially or totally fused, each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—; and the X birradicals of the backbone peptide sequence of formula (I), which are not bound to the "L" birradical, are amino acids, provided that at least one of them is selected from the group consisting of:
$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein P and Q are the same or different and represent a $(C_1-C_{10})$alkyl; $R_2$ is $(C_2-C_{10})$alkenyl; and the X birradicals of the backbone peptide sequence of formula (I), which are not bound to the "L" birradical, are amino acids, provided that at least one of them is selected from the group consisting of:
$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein P and Q are the same or different and represent a ($C_1$-$C_{10}$)alkyl, $R_2$ is ethylene; and the X birradicals of the backbone peptide sequence of formula (I), which are not bound to the "L" birradical, are amino acids, provided that at least one of them is selected from the group consisting of:

$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein:

"a" and "b" are 0;
"c" is 1;
P and Q are the same or different and represent a ($C_1$-$C_{10}$)alkyl;
$R_2$ is selected from the group consisting of: ($C_1$-$C_{10}$)alkyl, ($C_2$-$C_{10}$)alkenyl, ($C_2$-$C_{10}$)alkynyl and a known ring system comprising from 3 to 14 carbon atoms, the system comprising from 1 to 3 rings, where:
each one of the rings is saturated, partially unsaturated, or aromatic;
the rings are isolated, partially or totally fused, each one of the members forming the known ring system is selected from the group consisting of: —CH—, —$CH_2$—, —NH—, —N—, —SH—, —S—, and —O—; and
the ring system is optionally substituted by one or more radicals independently selected from the group consisting of halogen, —OH, —$NO_2$, ($C_1$-$C_{10}$)alkyl, ($C_1$-$C_{10}$)haloalkyl, and ($C_1$-$C_{10}$)alkyl-O—; and
the X birradicals of the backbone peptide sequence of formula (I), which are not bound to the "L" birradical, are amino acids, provided that at least one of them is selected from the group consisting of:

$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein:

"a" and "b" are 0;
"c" is 1;
P and Q are the same or different and represent a ($C_1$-$C_{10}$)alkyl;
$R_2$ is ($C_2$-$C_{10}$)alkenyl; and
X birradicals of the backbone peptide sequence of formula (I), which are not bound to the "L" birradical, are amino acids, provided that at least one of them is selected from the group consisting of:

$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein:

"a" and "b" are 0;
"c" is 1;
P and Q are the same or different and represent a ($C_1$-$C_{10}$)alkyl;
$R_2$ is ethylene; and
the X birradicals of the backbone peptide sequence of formula (I), which are not bound to the "L" birradical, are amino acids, provided that at least one of them is selected from the group consisting of:

$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein "a" and "b" are 0; "c" is 1; $R_2$ is selected from the group consisting of: ($C_1$-$C_{10}$)alkyl, ($C_2$-$C_{10}$)alkenyl, ($C_2$-$C_{10}$)alkynyl, and a known ring system comprising from 3 to 14 carbon atoms, the system comprising from 1 to 3 rings, where:
each one of the rings is saturated, partially unsaturated, or aromatic;
the rings are isolated, partially or totally fused, each one of the members forming the known ring system is selected from the group consisting of: —CH—, —$CH_2$—, —NH—, —N—, —SH—, —S—, and —O—; and
the ring system is optionally substituted by one or more radicals independently selected from the group consisting of halogen, —OH, —$NO_2$, ($C_1$-$C_{10}$)alkyl, ($C_1$-$C_{10}$)haloalkyl, and ($C_1$-$C_{10}$)alkyl-O—; the X birradicals which are bound to the "L" birradical being a compounds of formula (III)"L" birradical being a compounds of formula (III), wherein $R_{11}$ is ($C_1$-$C_{10}$)alkyl; and the X birradicals of the backbone peptide sequence of formula (I), which are not bound to the "L" birradical, are amino acids, provided that at least one of them is selected from the group consisting of:

$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein "a" and "b" are 0, "c" is 1; $R_2$ is ($C_2$-$C_{10}$)alkenyl; the X birradicals, which are bound to the "L" birradical, are compounds of formula (III), wherein $R_{11}$ is ($C_1$-$C_{10}$)alkyl; and the X birradicals of the backbone peptide sequence of formula (I), which are not bound to the "L" birradical, are amino acids, provided that at least one of them is selected from the group consisting of:

$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein "a" and "b" are 0, "c" is 1, $R_2$ is ethylene; the X birradicals, which are bound to the "L" birradical, are compounds of formula (III), wherein $R_{11}$ is $(C_1$-$C_{10})$alkyl; and the X birradicals of the backbone peptide sequence of formula (I), which are not bound to the "L" birradical, are amino acids, provided that at least one of them is selected from the group consisting of:
  $X_1$ represents an amino acid other than Glu,
  $X_2$ represents an amino acid other than Lys,
  $X_3$ represents an amino acid other than Ser,
  $X_4$ represents an amino acid other than Phe,
  $X_5$ represents an amino acid other than Ala, and
  $X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein P and Q are the same or different and represent a $(C_1$-$C_{10})$alkyl; $R_2$ is selected from the group consisting of: $(C_1$-$C_{10})$alkyl, $(C_2$-$C_{10})$alkenyl, $(C_2$-$C_{10})$alkynyl, and a known ring system comprising from 3 to 14 carbon atoms, the system comprising from 1 to 3 rings, where:
  each one of the rings is saturated, partially unsaturated, or aromatic;
  the rings are isolated, partially or totally fused, each one of the members forming the known ring system is selected from the group consisting of: —CH—, —CH$_2$—, —NH—, —N—, —SH—, —S—, and —O—; and
  the ring system is optionally substituted by one or more radicals independently selected from the group consisting of halogen, —OH, —NO$_2$, $(C_1$-$C_{10})$alkyl, $(C_1$-$C_{10})$haloalkyl, and $(C_1$-$C_{10})$alkyl-O—; the X birradicals, which are bound to the "L" birradical, are compounds of formula (III), wherein $R_{11}$ is $(C_1$-$C_{10})$alkyl; and the X birradicals of the backbone peptide sequence of formula (I), which are not bound to the "L" birradical, are amino acids, provided that at least one of them is selected from the group consisting of:
  $X_1$ represents an amino acid other than Glu,
  $X_2$ represents an amino acid other than Lys,
  $X_3$ represents an amino acid other than Ser,
  $X_4$ represents an amino acid other than Phe,
  $X_5$ represents an amino acid other than Ala, and
  $X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein P and Q are the same or different and represent a $(C_1$-$C_{10})$alkyl; $R_2$ is $(C_2$-$C_{10})$alkenyl; the X birradicals, which are bound to the "L" birradical, are compounds of formula (III), wherein $R_{11}$ is $(C_1$-$C_{10})$alkyl; and the X birradicals of the backbone peptide sequence of formula (I), which are not bound to the "L" birradical, are amino acids, provided that at least one of them is selected from the group consisting of:
  $X_1$ represents an amino acid other than Glu,
  $X_2$ represents an amino acid other than Lys,
  $X_3$ represents an amino acid other than Ser,
  $X_4$ represents an amino acid other than Phe,
  $X_5$ represents an amino acid other than Ala, and
  $X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein P and Q are the same or different and represent a $(C_1$-$C_{10})$alkyl, $R_2$ is ethylene; the X birradicals, which are bound to the "L" birradical, are compounds of formula (III), wherein $R_{11}$ is $(C_1$-$C_{10})$alkyl; and the X birradicals of the backbone peptide sequence of formula (I), which are not bound to the "L" birradical, are amino acids, provided that at least one of them is selected from the group consisting of:
  $X_1$ represents an amino acid other than Glu,
  $X_2$ represents an amino acid other than Lys,
  $X_3$ represents an amino acid other than Ser,
  $X_4$ represents an amino acid other than Phe,
  $X_5$ represents an amino acid other than Ala, and
  $X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein:
  "a" and "b" are 0;
  "c" is 1;
  P and Q are the same or different and represent a $(C_1$-$C_{10})$alkyl;
  $R_2$ is selected from the group consisting of: $(C_1$-$C_{10})$alkyl, $(C_2$-$C_{10})$alkenyl, $(C_2$-$C_{10})$alkynyl and a known ring system comprising from 3 to 14 carbon atoms, the system comprising from 1 to 3 rings, where:
    each one of the rings is saturated, partially unsaturated, or aromatic;
    the rings are isolated, partially or totally fused,
    each one of the members forming the known ring system is selected from the group consisting of: —CH—, —CH$_2$—, —NH—, —N—, —SH—, —S—, and —O—; and
    the ring system is optionally substituted by one or more radicals independently selected from the group consisting of halogen, —OH, —NO$_2$, $(C_1$-$C_{10})$alkyl, $(C_1$-$C_{10})$haloalkyl, and $(C_1$-$C_{10})$alkyl-O—;
  the X birradicals, which are bound to the "L" birradical, are compounds of formula (III), wherein $R_{11}$ is $(C_1$-$C_{10})$alkyl; and
  the X birradicals of the backbone peptide sequence of formula (I), which are not bound to the "L" birradical, are amino acids, provided that at least one of them is selected from the group consisting of:
    $X_1$ represents an amino acid other than Glu,
    $X_2$ represents an amino acid other than Lys,
    $X_3$ represents an amino acid other than Ser,
    $X_4$ represents an amino acid other than Phe,
    $X_5$ represents an amino acid other than Ala, and
    $X_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein:
  "a" and "b" are 0;
  "c" is 1;
  P and Q are the same or different and represent a $(C_1$-$C_{10})$alkyl;
  $R_2$ is $(C_2$-$C_{10})$alkenyl;
  the X birradicals, which are bound to the "L" birradical, are compounds of formula (III), wherein $R_{11}$ is $(C_1$-$C_{10})$alkyl; and
  X birradicals of the backbone peptide sequence of formula (I), which are not bound to the "L" birradical, are amino acids, provided that at least one of them is selected from the group consisting of:
    $X_1$ represents an amino acid other than Glu,
    $X_2$ represents an amino acid other than Lys, X$_3$ represents an amino acid other than Ser,
X$_4$ represents an amino acid other than Phe,
X$_5$ represents an amino acid other than Ala, and
X$_6$ represents an amino acid other than Gln.

In another embodiment of the first aspect of the invention, the peptide of formula (I), (Ibis1), (Ibis2) or (Ibis3) or a pharmaceutical salt thereof, is one wherein L corresponds to a birradical of formula (II) wherein:
"a" and "b" are 0;
"c" is 1;
P and Q are the same or different and represent a (C$_1$-C$_{10}$)alkyl;
R$_2$ is ethylene;
the X birradicals, which are bound to the "L" birradical, are compounds of formula (III), wherein R$_{11}$ is (C$_1$-C$_{10}$)alkyl; and
the X birradicals of the backbone peptide sequence of formula (I), which are not bound to the "L" birradical, are amino acids, provided that at least one of them is selected from the group consisting of:
X$_1$ represents an amino acid other than Glu,
X$_2$ represents an amino acid other than Lys,
X$_3$ represents an amino acid other than Ser,
X$_4$ represents an amino acid other than Phe,
X$_5$ represents an amino acid other than Ala, and
X$_6$ represents an amino acid other than Gln.

In one embodiment of the peptide of the first aspect of the invention, the peptide of formula (I), (Ibis1), (Ibis2) or (Ibis3) or a pharmaceutical salt thereof is one wherein:
"n" is 1 and "m", "p", and "q" are 0;
X$_4$ represents an amino acid other than Phe, and
X$_1$, X$_2$, and X$_5$ represent any amino acid; or alternatively,
"q" is 1 and "m", "n", and "p" are 0;
X$_3$ represents an amino acid other than Ser; and
X$_2$, X$_4$, and X$_6$ represent any amino acid; or alternatively,
"q" is 1 and "n", "m", and "p" are 0;
X$_4$ represents an amino acid other than Phe; and
X$_2$, X$_3$, and X$_6$ represent any amino acid; or alternatively,
"q" is 1 and "n", "m", and "p" are 0;
X$_3$ represents an amino acid other than Ser;
X$_4$ represents an amino acid other than Phe; and
X$_2$ and X$_6$ represent any amino acid.

In one embodiment of the first aspect of the invention, the peptide of formula (I), (Ibis1), (Ibis2) or (Ibis3) or a pharmaceutical salt thereof, is one wherein: "m" is 1; "n", "p", and "q" is 0. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein: "a" and "b" are 0; and "c" is 1. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein P and Q are the same or different and represent a (C$_1$-C$_{10}$)alkyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; and P and Q are the same or different and represent a (C$_1$-C$_{10}$)alkyl. In another embodiment of the first aspect of the invention, "m" is 1; "n", "p", and "q" is 0; and R$_2$ is selected from the group consisting of: (C$_1$-C$_{10}$)alkyl, (C$_2$-C$_{10}$)alkenyl, (C$_2$-C$_{10}$)alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein: "a" and "b" are 0; and "c" is 1; and R$_2$ is selected from the group consisting of: (C$_1$-C$_{10}$)alkyl, (C$_2$-C$_{10}$)alkenyl, (C$_2$-C$_{10}$)alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein P and Q are the same or different and represent a (C$_1$-C$_{10}$)alkyl; and R$_2$ is selected from the group consisting of: (C$_1$-C$_{10}$)alkyl, (C$_2$-C$_{10}$)alkenyl, (C$_2$-C$_{10}$)alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a (C$_1$-C$_{10}$)alkyl; and R$_2$ is selected from the group consisting of: (C$_1$-C$_{10}$)alkyl, (C$_2$-C$_{10}$)alkenyl. In another embodiment of the first aspect of the invention, "m" is 1; "n", "p", and "q" is 0; and R$_2$ is (C$_2$-C$_{10}$)alkenyl. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein: "a" and "b" are 0; and "c" is 1; and R$_2$ is (C$_2$-C$_{10}$)alkenyl. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein P and Q are the same or different and represent a (C$_1$-C$_{10}$)alkyl; and R$_2$ is (C$_2$-C$_{10}$)alkenyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a (C$_1$-C$_{10}$)alkyl; and R$_2$ is (C$_2$-C$_{10}$)alkenyl. In another embodiment of the first aspect of the invention, "m" is 1; "n", "p", and "q" is 0; and R$_2$ is ethylene. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein: "a" and "b" are 0; and "c" is 1; and $R_2$ is ethylene. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein P and Q are the same or different and represent a $(C_1-C_{10})$alkyl; and $R_2$ is ethylene. In another embodiment of the first aspect of the invention, the peptide of formula (I), (Ibis1), (Ibis2) or (Ibis3) or a pharmaceutical salt thereof, is one wherein:

embodiments provided above or below for the peptide of formula (I), (Ibis1), (Ibis2) or (Ibis3) or a pharmaceutical salt thereof where "m" is 1, and "n", "p", and "q" are 0, $X_4$ represents an amino acid other than Phe. In any of the embodiments provided above or below for the peptide of formula (I), (Ibis1), (Ibis2) or (Ibis3) or a pharmaceutical salt thereof where "m" is 1, and "n", "p", and "q" are 0, $X_4$ is Ala. In another embodiment, the peptide of formula (I), (Ibis1), (Ibis2) or (Ibis3) or a pharmaceutical salt thereof, is one of formula (I1) (also referred hereinafter as SEQ ID NO: 1 or "S02"):

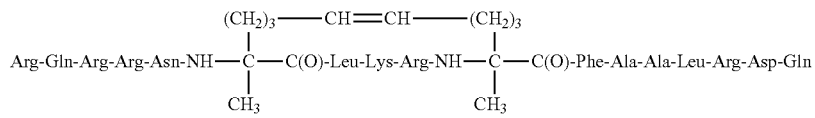

"a" and "b" are 0; "c" is 1; P and Q are the same or different and represent a $(C_1-C_{10})$alkyl; and $R_2$ is ethylene. In any of the embodiments provided above or below for the peptide of formula (I), (Ibis1), (Ibis2) or (Ibis3) or a pharmaceutical salt thereof, where "m" is 1, and "n", "p", and "q" are 0, $X_1$ and $X_3$ are the same.

In an embodiment, optionally in combination with any of the embodiments provided above or below for the peptide of formula (I), (Ibis1), (Ibis2) or (Ibis3) or a pharmaceutical salt thereof where "m" is 1, and "n", "p", and "q" are 0, $X_1$ and $X_3$ are the same and correspond to the compound of formula (III) wherein $R_{11}$ represents a $(C_1-C_{10})$alkyl, $(C_2-C_{10})$alkenyl, or $(C_2-C_{10})$alkynyl. In an embodiment, optionally in combination with any of the embodiments provided above or below for the peptide of formula (I), (Ibis1), (Ibis2) or (Ibis3) or a pharmaceutical salt thereof where "m" is 1, and "n", "p", and "q" are 0, $X_1$ and $X_3$ are the same and correspond to the compound of formula (III) wherein $R_{11}$ represents a $(C_1-C_{10})$alkyl or $(C_1-C_{10})$alkyl substituted with one or more halogen radicals. In an embodiment, optionally in combination with any of the embodiments provided above or below for the peptide of formula (I), (Ibis1), (Ibis2) or (Ibis3) or a pharmaceutical salt thereof where "m" is 1, and "n", "p", and "q" are 0, $X_1$ and $X_3$ are the same and correspond to the compound of formula (III) wherein $R_{11}$ represents a methyl radical:

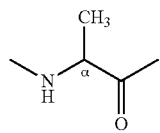

(IIIbis)

In an embodiment, optionally in combination with any of the embodiments provided above or below for the peptide of formula (I), (Ibis1), (Ibis2) or (Ibis3) or a pharmaceutical salt thereof where "m" is 1, and "n", "p", and "q" are 0, $X_2$, $X_4$, $X_5$, and $X_6$ are amino acids, provided that at least one of these amino acids is selected from the group consisting of: $X_2$ represents an amino acid other than Lys, $X_4$ represents an amino acid other than Phe, $X_5$ represents an amino acid other than Ala, and $X_6$ represents an amino acid other than Gln. In an embodiment, optionally in combination with any of the In one embodiment of the first aspect of the invention, the peptide of formula (I), (Ibis1), (Ibis2) or (Ibis3) or a pharmaceutical salt thereof, is one wherein: "n" is 1; "m", "p", and "q" are 0. In another embodiment of the first aspect of the invention, the peptide of formula (I), (Ibis1), (Ibis2) or (Ibis3) or a pharmaceutical salt thereof, is one wherein: "n" is 1; "m", "p", and "q" are 0; L corresponds to a birradical of formula (II) wherein: "a" and "b" are 0; and "c" is 1. In another embodiment of the first aspect of the invention, the peptide of formula (I), (Ibis1), (Ibis2) or (Ibis3) or a pharmaceutical salt thereof, is one wherein: "n" is 1; "m", "p", and "q" are 0; L corresponds to a birradical of formula (II) wherein P and Q are the same or different and represent a $(C_1-C_{10})$alkyl, $(C_2-C_{10})$alkenyl, or $(C_2-C_{10})$alkynyl radical, said radicals being substituted or non-substituted. In another embodiment of the first aspect of the invention, the peptide of formula (I), (Ibis1), (Ibis2) or (Ibis3) or a pharmaceutical salt thereof, is one wherein: "n" is 1; "m", "p", and "q" are 0; L corresponds to a birradical of formula (II) wherein P and Q are the same or different and represent a $(C_1-C_{10})$alkyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; and P and Q are the same or different and represent a $(C_1-C_{10})$alkyl. In another embodiment of the first aspect of the invention, "n" is 1; "m", "p", and "q" are 0; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein: "a" and "b" are 0; and "c" is 1; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—. In another embodiment of the first aspect of the invention, the peptide of formula (I), (Ibis1), (Ibis2) or (Ibis3) or a pharmaceutical salt thereof, is one wherein: "n" is 1; "m", "p", and "q" are 0; L corresponds to a birradical of formula (II) wherein P and Q are the same or different and represent a (C$_1$-C$_{10}$)alkyl; and R$_2$ is selected from the group consisting of: (C$_1$-C$_{10}$)alkyl, (C$_2$-C$_{10}$)alkenyl, (C$_2$-C$_{10}$)alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—. In another embodiment of the first aspect of the invention, the peptide of formula (I), (Ibis1), (Ibis2) or (Ibis3) or a pharmaceutical salt thereof, is one wherein: "n" is 1; "m", "p", and "q" are 0; L corresponds to a birradical of formula (II) wherein R$_2$ represents a (C$_1$-C$_{10}$) alkyl, (C$_2$-C$_{10}$)alkenyl, or (C$_2$-C$_{10}$)alkynyl radical, said radical being substituted or non-substituted. In another embodiment of the first aspect of the invention, the peptide of formula (I), (Ibis1), (Ibis2) or (Ibis3) or a pharmaceutical salt thereof, is one wherein: "n" is 1; "m", "p", and "q" are 0; L corresponds to a birradical of formula (II) wherein P and Q represent (C$_1$-C$_{10}$)alkyl and R$_2$ represents a (C$_1$-C$_{10}$)alkyl, (C$_2$-C$_{10}$)alkenyl, or (C$_2$-C$_{10}$)alkynyl radical. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a (C$_1$-C$_{10}$)alkyl; and R$_2$ is selected from the group consisting of: (C$_1$-C$_{10}$) alkyl, (C$_2$-C$_{10}$)alkenyl. In another embodiment of the first aspect of the invention, "n" is 1; "m", "p", and "q" are 0; and R$_2$ is (C$_2$-C$_{10}$)alkenyl. In another embodiment of the first aspect of the invention, the peptide of formula (I), (Ibis1), (Ibis2) or (Ibis3) or a pharmaceutical salt thereof, is one wherein: "n" is 1; "m", "p", and "q" are 0; L corresponds to a birradical of formula (II) wherein: "a" and "b" are 0; and "c" is 1; and R$_2$ is (C$_2$-C$_{10}$)alkenyl. In another embodiment of the first aspect of the invention, the peptide of formula (I), (Ibis1), (Ibis2) or (Ibis3) or a pharmaceutical salt thereof, is one wherein: "m" is 1; "n", "p", and "q" is 0; L corresponds to a birradical of formula (II) wherein P and Q are the same or different and represent a (C$_1$-C$_{10}$)alkyl; and R$_2$ is (C$_2$-C$_{10}$)alkenyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a (C$_1$-C$_{10}$)alkyl; and R$_2$ is (C$_2$-C$_{10}$)alkenyl. In another embodiment of the first aspect of the invention, "n" is 1; "m", "p", and "q" are 0; and R$_2$ is ethylene. In another embodiment of the first aspect of the invention, the peptide of formula (I), (Ibis1), (Ibis2) or (Ibis3) or a pharmaceutical salt thereof, is one wherein: "n" is 1; "m", "p", and "q" are 0; L corresponds to a birradical of formula (II) wherein: "a" and "b" are 0; and "c" is 1; and R$_2$ is ethylene. In another embodiment of the first aspect of the invention, the peptide of formula (I), (Ibis1), (Ibis2) or (Ibis3) or a pharmaceutical salt thereof, is one wherein: "n" is 1; "m", "p", and "q" are 0; L corresponds to a birradical of formula (II) wherein P and Q are the same or different and represent a (C$_1$-C$_{10}$)alkyl; and R$_2$ is ethylene. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a (C$_1$-C$_{10}$)alkyl; and R$_2$ is ethylene. In another embodiment of the first aspect of the invention, optionally in combination with any of the embodiments provided above or below, the peptide of formula (I), (Ibis1), (Ibis2) or (Ibis3) or a pharmaceutical salt thereof, is one wherein: "n" is 1; "m", "p", and "q" are 0; and L corresponds to formula (VII)

$$—(CH_2)_x—CH\!=\!CH—(CH_2)_y— \quad\quad\quad (VII)$$

wherein x and y are the same or different and are integer values selected from 1 to 10.

In one embodiment, optionally in combination with any of the embodiments provided above or below for the peptide of formula (I), (Ibis1), (Ibis2) or (Ibis3) or a pharmaceutical salt thereof where "n" is 1, and "m", "p", and "q" are 0, X$_3$ and X$_6$ are the same. In one embodiment, optionally in combination with any of the embodiments provided above or below for the peptide of formula (I), (Ibis1), (Ibis2) or (Ibis3) or a pharmaceutical salt thereof where "n" is 1, and "m", "p", and "q" are 0, X$_3$ and X$_6$ are the same and correspond to the compound of formula (III) wherein R$_{11}$ represents a (C$_1$-C$_{10}$)alkyl, (C$_2$-C$_{10}$)alkenyl, or (C$_2$-C$_{10}$)alkynyl. In one embodiment, optionally in combination with any of the embodiments provided above or below for the peptide of formula (I), (Ibis1), (Ibis2) or (Ibis3) or a pharmaceutical salt thereof where "n" is 1, and "m", "p", and "q" are 0, X$_3$ and X$_6$ are the same and correspond to the compound of formula (III) wherein R$_{11}$ represents a (C$_1$-C$_{10}$)alkyl or (C$_1$-C$_{10}$)alkyl substituted with one or more halogen radicals. In one embodiment, optionally in combination with any of the embodiments provided above or below for the peptide of formula (I), (Ibis1), (Ibis2) or (Ibis3) or a pharmaceutical salt thereof where "n" is 1, and "m", "p", and "q" are 0, X$_3$ and X$_6$ are the same and correspond to the compound of formula (III) wherein R$_{11}$ represents a methyl radical:

(IIIbis)

In one embodiment, optionally in combination with any of the embodiments provided above or below for the peptide of formula (I), (Ibis1), (Ibis2) or (Ibis3) or a pharmaceutical salt thereof where "n" is 1, and "m", "p", and "q" are 0, X$_1$, X$_2$, X$_4$, and X$_5$ are amino acids, provided that at least one of these amino acids is selected from the group consisting of: X$_1$ represents an amino acid other than Glu, X$_2$ represents an amino acid other than Lys, X$_4$ represents an amino acid other than Phe, and X$_5$ represents an amino acid other than Ala. In one embodiment, optionally in combination with any of the embodiments provided above or below for the peptide of formula (I), (Ibis1), (Ibis2) or (Ibis3) or a pharmaceutical salt thereof where "n" is 1, and "m", "p", and "q" are 0, X$_4$ represents an amino acid other than Phe. In one embodiment, optionally in combination with any of the embodiments provided above or below for the peptide of formula (I), (Ibis1), (Ibis2) or (Ibis3) or a pharmaceutical salt thereof where "n" is 1, and "m", "p", and "q" are 0, $X_4$ represents an D-amino acid other than D-Phe.

As it is shown below, when the native amino acid, Phe, at position 12 was replaced by another non-polar amino acid with a linear hydrocarbon side-chain such as Ala, a surprising anti-cancer "activation" of the wild-type sequence occurred. The same surprising effect can be expected with other non-polar amino acids having linear hydrocarbon side-chains. Thus, in another embodiment of the first aspect of the invention, optionally in combination with any of the embodiments provided above or below, $X_4$ represents an amino acid selected from Ala, Ile, Leu, Val, and Gly. In another embodiment of the first aspect of the invention, optionally in combination with any of the embodiments provided above or below, "n" is 1 and "m", "p", and "q" are 0; $X_4$ represents an amino acid selected from Ala, Ile, Leu, Val, and Gly; and $X_3$ and $X_6$ are the same. In one embodiment, optionally in combination with any of the embodiments provided above or below for the peptide of formula (I), (Ibis1), (Ibis2) or (Ibis3) or a pharmaceutical salt thereof where "n" is 1, and "m", "p", and "q" are 0, and $X_4$ is Ala. In one embodiment, optionally in combination with any of the embodiments provided above or below for the peptide of formula (I), (Ibis1), (Ibis2) or (Ibis3) or a pharmaceutical salt thereof where "n" is 1, and "m", "p", and "q" are 0; $X_1$ is an acidic amino acid; $X_2$ represents a basic amino acid; $X_4$ represents an amino acid selected from Ala, Ile, Leu, Val, and Gly; $X_5$ represents a non-polar amino acid; and $X_3$ and $X_6$ are the same.

In another embodiment, the peptide of formula (I) is one of formula (I2), (I3) or (I4) (hereinafter also referred as SEQ ID NO: 2 (or "S04"), 3 (or "S12") and 4 (or "S13"), respectively):

peptide of formula (I), (Ibis1), (Ibis2) or (Ibis3) or a pharmaceutical salt thereof, is one wherein: "p" is 1; "m", "n", and "q" are 0; L corresponds to a birradical of formula (II) wherein P and Q are the same or different and represent a $(C_1-C_{10})$alkyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; and P and Q are the same or different and represent a $(C_1-C_{10})$alkyl. In another embodiment of the first aspect of the invention, "p" is 1; "m", "n", and "q" are 0; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$ alkyl-O—. In another embodiment of the first aspect of the invention, the peptide of formula (I), (Ibis1), (Ibis2) or (Ibis3) or a pharmaceutical salt thereof, is one wherein: "p" is 1; "m", "n", and "q" are 0; L corresponds to a birradical of formula (II) wherein: "a" and "b" are 0; and "c" is 1; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently

SEQ ID NO: 2

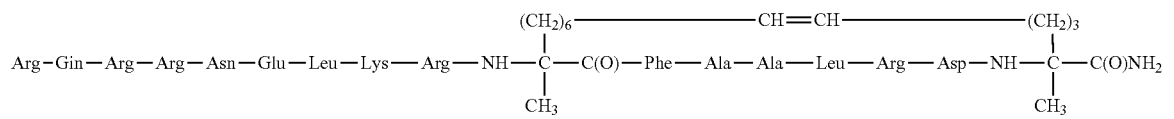

SEQ ID NO: 3

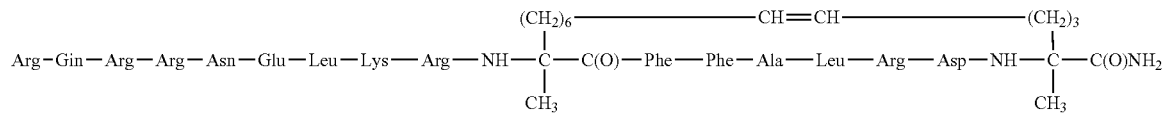

SEQ ID NO: 4

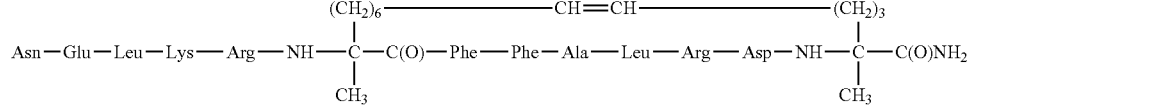

In one embodiment of the first aspect of the invention, the peptide of formula (I), (Ibis1), (Ibis2) or (Ibis3) or a pharmaceutical salt thereof, is one wherein: "p" is 1; "m", "n", and "q" are 0. In another embodiment of the first aspect of the invention, the peptide of formula (I), (Ibis1), (Ibis2) or (Ibis3) or a pharmaceutical salt thereof, is one wherein: "p" is 1; "m", "n", and "q" are 0; L corresponds to a birradical of formula (II) wherein: "a" and "b" are 0; and "c" is 1. In another embodiment of the first aspect of the invention, the selected from the group consisting of halogen, —OH, —NO$_2$, $(C_1-C_{10})$alkyl, $(C_1-C_{10})$haloalkyl, and $(C_1-C_{10})$ alkyl-O—. In another embodiment of the first aspect of the invention, the peptide of formula (I), (Ibis1), (Ibis2) or (Ibis3) or a pharmaceutical salt thereof, is one wherein: "p" is 1; "m", "n", and "q" are 0; L corresponds to a birradical of formula (II) wherein P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a (C$_1$-C$_{10}$)alkyl; and R$_2$ is selected from the group consisting of: (C$_1$-C$_{10}$)alkyl, (C$_2$-C$_{10}$)alkenyl. In another embodiment of the first aspect of the invention, "p" is 1; "m", "n", and "q" are 0; and R$_2$ is (C$_2$-C$_{10}$)alkenyl. In another embodiment of the first aspect of the invention, the peptide of formula (I), (Ibis1), (Ibis2) or (Ibis3) or a pharmaceutical salt thereof, is one wherein: "p" is 1; "m", "n", and "q" are 0; L corresponds to a birradical of formula (II) wherein: "a" and "b" are 0; and "c" is 1; and R$_2$ is (C$_2$-C$_{10}$)alkenyl. In another embodiment of the first aspect of the invention, the peptide of formula (I), (Ibis1), (Ibis2) or (Ibis3) or a pharmaceutical salt thereof, is one wherein: "p" is 1; "m", "n", and "q" are 0; L corresponds to a birradical of formula (II) wherein P and Q are the same or different and represent a (C$_1$-C$_{10}$)alkyl; and R$_2$ is (C$_2$-C$_{10}$)alkenyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a (C$_1$-C$_{10}$)alkyl; and R$_2$ is (C$_2$-C$_{10}$)alkenyl. In another embodiment of the first aspect of the invention, "p" is 1; "m", "n", and "q" are 0; and R$_2$ is ethylene. In another embodiment of the first aspect of the invention, the peptide of formula (I), (Ibis1), (Ibis2) or (Ibis3) or a pharmaceutical salt thereof, is one wherein: "p" is 1; "m", "n", and "q" are 0; L corresponds to a birradical of formula (II) wherein: "a" and "b" are 0; and "c" is 1; and R$_2$ is ethylene. In another embodiment of the first aspect of the invention, the peptide of formula (I), (Ibis1), (Ibis2) or (Ibis3) or a pharmaceutical salt thereof, is one wherein: "p" is 1; "m", "n", and "q" are 0; L corresponds to a birradical of formula (II) wherein P and Q are the same or different and represent a (C$_1$-C$_{10}$)alkyl; and R$_2$ is ethylene. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a (C$_1$-C$_{10}$)alkyl; and R$_2$ is ethylene. In one embodiment, optionally in combination with any of the embodiments provided above or below for the peptide of formula (I), (Ibis1), (Ibis2) or (Ibis3) or a pharmaceutical salt thereof where "p" is 1, and "m", "n", and "q" are 0, X$_2$ and X$_4$ are the same. In one embodiment, optionally in combination with any of the embodiments provided above or below for the peptide of formula (I), (Ibis1), (Ibis2) or (Ibis3) or a pharmaceutical salt thereof where "p" is 1, X$_2$ and X$_4$ are the same and correspond to the compound of formula (III) wherein R$_{11}$ represents a (C$_1$-C$_{10}$)alkyl, (C$_2$-C$_{10}$)alkenyl, or (C$_2$-C$_{10}$)alkynyl. In one embodiment, optionally in combination with any of the embodiments provided above or below for the peptide of formula (I), (Ibis1), (Ibis2) or (Ibis3) or a pharmaceutical salt thereof where "p" is 1, and "m", "n", and "q" are 0, X$_2$ and X$_4$ are the same and correspond to the compound of formula (III) wherein R$_{11}$ represents a (C$_1$-C$_{10}$)alkyl or (C$_1$-C$_{10}$)alkyl substituted with one or more halogen radicals. In one embodiment, optionally in combination with any of the embodiments provided above or below for the peptide of formula (I), (Ibis1), (Ibis2) or (Ibis3) or a pharmaceutical salt thereof where "p" is 1, and "m", "n", and "q" are 0, X$_2$ and X$_4$ are the same and correspond to the compound of formula (III) wherein R$_{11}$ represents a methyl radical:

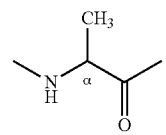

(IIIbis)

In one embodiment, optionally in combination with any of the embodiments provided above or below for the peptide of formula (I), (Ibis1), (Ibis2) or (Ibis3) or a pharmaceutical salt thereof, where "p" is 1, and "m", "n", and "q" are 0, X$_1$, X$_3$, X$_5$, and X$_6$ are amino acids, provided that at least one of these amino acids is selected from the group consisting of: X$_1$ represents an amino acid other than Glu, X$_3$ represents an amino acid other than Ala, X$_5$ represents an amino acid other than Ala, and X$_6$ represents an amino acid other than Gln. In one embodiment, optionally in combination with any of the embodiments provided above or below for the peptide of formula (I), (Ibis1), (Ibis2) or (Ibis3) or a pharmaceutical salt thereof, the peptide of formula (I) is one of formula (I5) (hereinafter also referred as SEQ ID NO: 5 or "S01"):

SEQ ID NO: 5

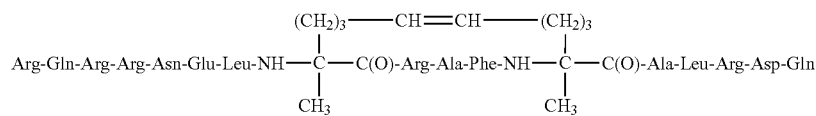

In one embodiment of the first aspect of the invention, the peptide of formula (I), (Ibis1), (Ibis2) or (Ibis3) or a pharmaceutical salt thereof, is one wherein: "q" is 1; "m", "n", and "p" are 0. In another embodiment of the first aspect of the invention, the peptide of formula (I), (Ibis1), (Ibis2) or (Ibis3) or a pharmaceutical salt thereof, is one wherein: "q" is 1; "m", "n", and "p" are 0; L corresponds to a birradical of formula (II) wherein: "a" and "b" are 0; and "c" is 1. In another embodiment of the first aspect of the invention, the peptide of formula (I), (Ibis1), (Ibis2) or (Ibis3) or a pharmaceutical salt thereof, is one wherein: "q" is 1; "m", "n", and "p" are 0; L corresponds to a birradical of formula (II) wherein P and Q are the same or different and represent a (C$_1$-C$_{10}$)alkyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a (C$_1$-C$_{10}$)alkyl, (C$_2$-C$_{10}$)alkenyl, or (C$_2$-C$_{10}$)alkynyl radical, said radicals being substituted or non-substituted. In another embodiment of the first aspect of the invention, the peptide of formula (I), (Ibis1), (Ibis2) or (Ibis3) or a pharmaceutical salt thereof, is one wherein: "a" and "b" are 0; "c" is 1; and P and Q are the same or different and represent a $(C_1-C_{10})$alkyl. In another embodiment of the first aspect of the invention, "q" is 1; "m", "n", and "p" are 0; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the first aspect of the invention, the peptide of formula (I), (Ibis1), (Ibis2) or (Ibis3) or a pharmaceutical salt thereof, is one wherein: "q" is 1; "m", "n", and "p" are 0; L corresponds to a birradical of formula (II) wherein: "a" and "b" are 0; and "c" is 1; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the first aspect of the invention, the peptide of formula (I), (Ibis1), (Ibis2) or (Ibis3) or a pharmaceutical salt thereof, is one wherein: "q" is 1; "m", "n", and "p" are 0; L corresponds to a birradical of formula (II) wherein P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a $(C_1-C_{10})$alkyl; and $R_2$ is selected from the group consisting of: $(C_1-C_{10})$alkyl, $(C_2-C_{10})$alkenyl. In another embodiment of the first aspect of the invention, "q" is 1; "m", "n", and "p" are 0; and $R_2$ is $(C_2-C_{10})$alkenyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; and $R_2$ represents a $(C_1-C_{10})$alkyl, $(C_2-C_{10})$alkenyl, or $(C_2-C_{10})$alkynyl radical, said radical being substituted or non-substituted. In another embodiment of the first aspect of the invention, the peptide of formula (I), (Ibis1), (Ibis2) or (Ibis3) or a pharmaceutical salt thereof, is one wherein: "q" is 1; "m", "n", and "p" are 0; L corresponds to a birradical of formula (II) wherein: "a" and "b" are 0; and "c" is 1; and $R_2$ is $(C_2-C_{10})$alkenyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q represent $(C_1-C_{10})$alkyl; and $R_2$ represents a $(C_1-C_{10})$alkyl, $(C_2-C_{10})$alkenyl, or $(C_2-C_{10})$alkynyl radical, said radical being substituted or non-substituted. In another embodiment of the first aspect of the invention, the peptide of formula (I), (Ibis1), (Ibis2) or (Ibis3) or a pharmaceutical salt thereof, is one wherein: "q" is 1; "m", "n", and "p" are 0; L corresponds to a birradical of formula (II) wherein P and Q are the same or different and represent a $(C_1-C_{10})$alkyl; and $R_2$ is $(C_2-C_{10})$alkenyl. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a $(C_1-C_{10})$alkyl; and $R_2$ is $(C_2-C_{10})$alkenyl. In another embodiment of the first aspect of the invention, "q" is 1; "m", "n", and "p" are 0; and $R_2$ is ethylene. In another embodiment of the first aspect of the invention, the peptide of formula (I), (Ibis1), (Ibis2) or (Ibis3) or a pharmaceutical salt thereof, is one wherein: "q" is 1; "m", "n", and "p" are 0; L corresponds to a birradical of formula (II) wherein: "a" and "b" are 0; and "c" is 1; and $R_2$ is ethylene. In another embodiment of the first aspect of the invention, the peptide of formula (I), (Ibis1), (Ibis2) or (Ibis3) or a pharmaceutical salt thereof, is one wherein: "q" is 1; "m", "n", and "p" are 0; L corresponds to a birradical of formula (II) wherein P and Q are the same or different and represent a $(C_1-C_{10})$alkyl; and $R_2$ is ethylene. In another embodiment of the first aspect of the invention, the peptide of formula (I), (Ibis1), (Ibis2) or (Ibis3) or a pharmaceutical salt thereof, is one wherein: "a" and "b" are 0; "c" is 1; P and Q are the same or different and represent a $(C_1-C_{10})$alkyl; and $R_2$ is ethylene. In another embodiment of the first aspect of the invention, optionally in combination with any of the embodiments provided above or below, the peptide of formula (I), (Ibis1), (Ibis2) or (Ibis3) or a pharmaceutical salt thereof, is one wherein: "q" is 1; "m", "n", and "p" are 0; and L corresponds to formula (VII)

$$—(CH_2)_x—CH=CH—(CH_2)_y— \quad (VII)$$

wherein x and y are the same or different and are integer values selected from 1 to 10.

In one embodiment, optionally in combination with any of the embodiments provided above or below for the peptide of formula (I), (Ibis1), (Ibis2) or (Ibis3) or a pharmaceutical salt thereof where "q" is 1, $X_1$ and $X_5$ are the same. In one embodiment, optionally in combination with any of the embodiments provided above or below for the peptide of formula (I), (Ibis1), (Ibis2) or (Ibis3) or a pharmaceutical salt thereof where "q" is 1, $X_1$ and $X_5$ are the same and correspond to the compound of formula (III) wherein $R_{11}$ represents a $(C_1-C_{10})$alkyl, $(C_2-C_{10})$alkenyl, or $(C_2-C_{10})$alkynyl. In one embodiment, optionally in combination with any of the embodiments provided above or below for the peptide of formula (I), (Ibis1), (Ibis2) or (Ibis3) or a pharmaceutical salt thereof where "q" is 1, $X_1$ and $X_5$ are the same and correspond to the compound of formula (III) wherein $R_{11}$ represents a $(C_1-C_{10})$alkyl or $(C_1-C_{10})$alkyl substituted with one or more halogen radicals. In one embodiment, optionally in combination with any of the embodiments provided above or below for the peptide of formula (I), (Ibis1), (Ibis2) or (Ibis3) or a pharmaceutical salt thereof where "q" is 1, $X_1$ and $X_5$ are the same and correspond to the compound of formula (III) wherein $R_{11}$ represents a methyl radical:

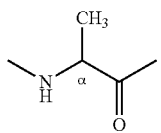

(IIIbis)

In one embodiment, optionally in combination with any of the embodiments provided above or below for the peptide of formula (I), (Ibis1), (Ibis2) or (Ibis3) or a pharmaceutical salt thereof where "q" is 1, $X_2$, $X_3$, $X_4$, and $X_6$ are amino acids, provided that at least one of these amino acids is selected from the group consisting of: $X_2$ represents an amino acid other than Lys, $X_3$ represents an amino acid other than Ser, $X_4$ represents an amino acid other than Phe, and $X_6$ represents an amino acid other than Gln. In one embodiment, optionally in combination with any of the embodiments provided above or below for the peptide of formula (I), (Ibis1), (Ibis2) or (Ibis3) or a pharmaceutical salt thereof where "q" is 1, and "m", "n", and "p" are 0, $X_2$, $X_3$, $X_4$, and $X_6$ are amino acids, provided that $X_3$ represents an amino acid other than Ser, $X_4$ represents an amino acid other than Phe, and $X_2$ and $X_6$ can be any amino acids as defined above. In one embodiment, optionally in combination with any of the embodiments provided above or below for the peptide of formula (I), (Ibis1), (Ibis2) or (Ibis3) or a pharmaceutical salt thereof where "q" is 1, and "m", "n", and "p" are 0, $X_3$ is a D-amino acid other than Ser. In one embodiment, optionally in combination with any of the embodiments provided above or below for the peptide of formula (I), (Ibis1), (Ibis2) or (Ibis3) or a pharmaceutical salt thereof where "q" is 1, $X_4$ is a D-amino acid other than Phe. In one embodiment, optionally in combination with any of the embodiments provided above or below for the peptide of formula (I), (Ibis1), (Ibis2) or (Ibis3) or a pharmaceutical salt thereof where "q" is 1, $X_3$ represents a non-polar amino acid and $X_4$ represents a non-polar amino acid selected from Ala, Ile, Leu, Val, and Gly. In another embodiment, optionally in combination with any of the embodiments provided above or below for the peptide of formula (I), (Ibis1), (Ibis2) or (Ibis3) or a pharmaceutical salt thereof where "q" is 1, $X_3$ and $X_4$ are the same. In one embodiment, optionally in combination with any of the embodiments provided above or below for the peptide of formula (I), (Ibis1), (Ibis2) or (Ibis3) or a pharmaceutical salt thereof where "q" is 1, and "m", "n", and "p" are 0, $X_4$ is Ala. In another embodiment, optionally in combination with any of the embodiments provided above or below for the peptide of formula (I), (Ibis1), (Ibis2) or (Ibis3) or a pharmaceutical salt thereof where "q" is 1, $X_3$ and $X_4$ represent Ala. In another embodiment, optionally in combination with any of the embodiments provided above or below for the peptide of formula (I), (Ibis1), (Ibis2) or (Ibis3) or a pharmaceutical salt thereof where "q" is 1, $X_2$ is a basic amino acid and $X_6$ is an acid amino acid.

In another embodiment, the peptide of formula (I) is one of formula (I6) (hereinafter also referred as SEQ ID NO: 6 or "S03"):

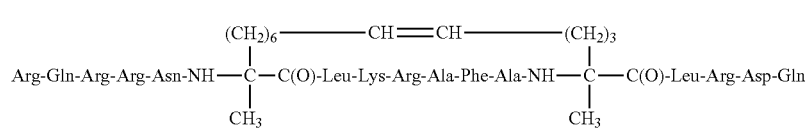

SEQ ID NO: 6

In another embodiment, the present invention provides the following metabolites derived from sequence SEQ ID NO: 6 ("S03"):

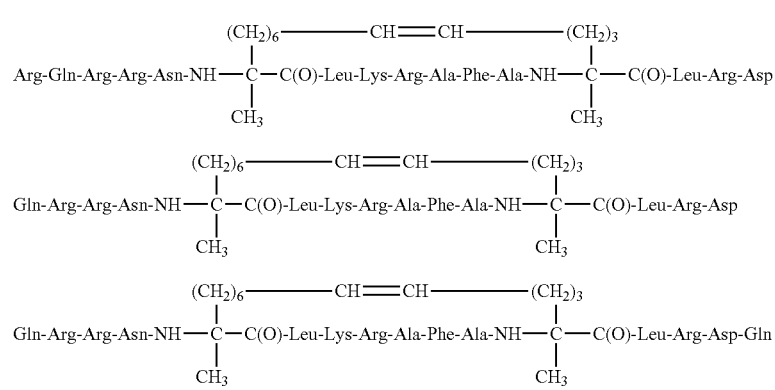

S311 (SEQ ID NO: 29)

S312 (SEQ ID NO: 30)

S313 (SEQ ID NO: 31)

As it is shown below, these metabolites show anti-cancer activity.

In another embodiment of the first aspect of the invention, the peptide of formula (I), (Ibis1), (Ibis2) or (Ibis3) or a pharmaceutical salt thereof is one wherein "m", "n", "p", and "q" are 0. In another embodiment of the first aspect of the invention, the peptide of formula (I), (Ibis1), (Ibis2) or (Ibis3) or a pharmaceutical salt thereof is one wherein "m", "n", "p", and "q" are 0, and $X_1$ to $X_6$ are amino acids, provided that at least three of $X_1$ to $X_6$ are amino acids selected from: $X_1$ represents an amino acid other than Glu, $X_2$ represents an amino acid other than Lys, $X_3$ represents an amino acid other than Ser, $X_4$ represents an amino acid other than Phe, $X_5$ represents an amino acid other than Ala, and $X_6$ represents an amino acid other than Gln. In another embodiment of the first aspect of the invention, the peptide of formula (I), (Ibis1), (Ibis2) or (Ibis3) or a pharmaceutical salt thereof is one wherein "m", "n", "p", and "q" are 0, and three of the radicals $X_1$ to $X_6$ are selected from: $X_1$ represents an amino acid other than Glu, $X_2$ represents an amino acid other than Lys, $X_3$ represents an amino acid other than Ser, $X_4$ represents an amino acid other than Phe, $X_5$ represents an amino acid other than Ala, and $X_6$ represents an amino acid other than Gln. In another embodiment of the first aspect of the invention, the peptide of formula (I), (Ibis1), (Ibis2) or (Ibis3) or a pharmaceutical salt thereof is one wherein "m", "n", "p", and "q" are 0, and $X_3$ represents an amino acid other than Ser, $X_5$ represents an amino acid other than Ala, and $X_6$ represents an amino acid other than Gln. In another embodiment of the first aspect of the invention, optionally in combination with any of the embodiments provided above or below for m, n, p, and q equal to 0, the peptide of formula (I), (Ibis1), (Ibis2) or (Ibis3) or a pharmaceutical salt thereof is one wherein "m", "n", "p", and "q" are 0, and $X_3$ represents an amino acid other than Ser. In another embodiment of the first aspect of the invention, optionally in combination with any of the embodiments provided above or below for m, n, p, and q equal to 0, the peptide of formula (I), (Ibis1), (Ibis2) or (Ibis3) or a pharmaceutical salt thereof is one wherein "m", "n", "p", and "q" are 0, and $X_3$ represents a D-amino acid other than Ser. In another embodiment of the first aspect of the invention, optionally in combination with any of the embodiments provided above or below for m, n, p, and q equal to 0, the peptide of formula (I), (Ibis1), (Ibis2) or (Ibis3) or a pharmaceutical salt thereof is one wherein "m", "n", "p", and "q" are 0, and $X_3$ is Leu. In another embodiment of the first aspect of the invention, optionally in combination with any of the embodiments provided above or below for m, n, p, and q equal to 0, the peptide of formula (I), (Ibis1), (Ibis2) or (Ibis3) or a pharmaceutical salt thereof is one wherein "m", "n", "p", and "q" are 0, and $X_5$ represents a D-amino acid other than Ala. In another embodiment of the first aspect of the invention, optionally in combination with any of the embodiments provided above or below for m, n, p, and q equal to 0, the peptide of formula (I), (Ibis1), (Ibis2) or (Ibis3) or a pharmaceutical salt thereof is one wherein "m", "n", "p", and "q" are 0, and $X_5$ is Thr. In another embodiment of the first aspect of the invention, optionally in combination with any of the embodiments provided above or below for m, n, p, and q equal to 0, the peptide of formula (I), (Ibis1), (Ibis2) or (Ibis3) or a pharmaceutical salt thereof is one wherein: "m", "n", "p", and "q" are 0, and $X_6$ represents a D-amino acid other than Gln. In another embodiment of the first aspect of the invention, optionally in combination with any of the embodiments provided above or below for m, n, p, and q equal to 0, the peptide of formula (I), (Ibis1), (Ibis2) or (Ibis3) or a pharmaceutical salt thereof is one wherein "m", "n", "p", and "q" are 0 and $X_6$ is Ile. In another embodiment of the first aspect of the invention, optionally in combination with any of the embodiments provided above or below for m, n, p, and q equal to 0, the peptide of formula (I), (Ibis1), (Ibis2) or (Ibis3) or a pharmaceutical salt thereof which is of formula (I7) (hereinafter also referred as SEQ ID NO: 7 or "L05"):

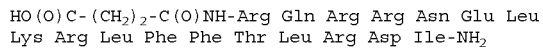
HO(O)C-(CH$_2$)$_2$-C(O)NH-Arg Gln Arg Arg Asn Glu Leu Lys Arg Leu Phe Phe Thr Leu Arg Asp Ile-NH$_2$ In this peptide, the amino group of the residue in N(t) (i.e., Arg) corresponds to a —NH-succinyl group and the carboxylic group of the residue in C(t) (i.e., Ile) corresponds to an amide, —CO—NH$_2$.

In a second aspect, the present invention provides a peptide or pharmaceutical salt thereof of formula (IV).

In one embodiment of the second aspect of the invention, z is 1, and the peptide or salt thereof is of formula (IVbis1):

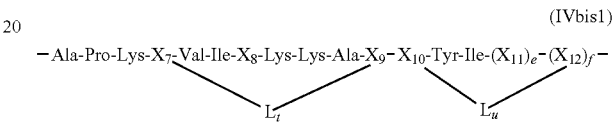

In a further embodiment of the second aspect of the invention, z is 1, and the peptide or salt thereof consisting of the formula (IVbis2):

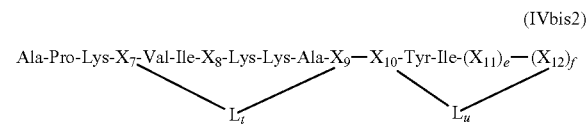

In another embodiment of the second aspect of the invention, the peptide or pharmaceutical salt is one wherein when v is 1, then: (a) the C-terminal group of the peptide corresponds to a —C(O)R$_{15}$, wherein R$_{15}$ is a radical selected from the group consisting of: —OR$_{16}$, —NR$_{17}$R$_{18}$, —O(C$_1$-C$_{20}$)alkylC(O)OR$_{19}$, —O(C$_1$-C$_{20}$)alkylC(O)R$_{20}$, —O(C$_1$-C$_{20}$)alkylOR$_{21}$, —O(C$_1$-C$_{20}$)C(O)NR$_{22}$R$_{23}$, or a polymer, such as a polyol, such as polyethylene glycol (PEG) being R$_{15}$, R$_{16}$, R$_{17}$, R$_{18}$, R$_{19}$, R$_{20}$, R$_{21}$, R$_{22}$ and R$_{23}$ radicals selected from the group consisting of: hydrogen, (C$_1$-C$_{10}$)alkyl, (C$_2$-C$_{10}$)alkenyl, (C$_2$-C$_{10}$)alkenyl, and a known ring system comprising from 3 to 14 carbon atoms, the system comprising from 1 to 3 rings, where:
  each one of the rings is saturated, partially unsaturated, or aromatic;
    the rings are isolated, partially or totally fused, each one of the members forming the known ring system is selected from the group consisting of: —CH—, —CH$_2$—, —NH—, —N—, —SH—, —S—, and —O—; and
  the ring system is optionally substituted by one or more radicals independently selected from the group consisting of halogen, —OH, —NO$_2$, (C$_1$-C$_{10}$)alkyl, (C$_1$-C$_{10}$) haloalkyl, and (C$_1$-C$_{10}$)alkyl-O—;
and (b) the N-terminal group is selected from —NR$_{24}$R$_{25}$, —NHC(O)R$_{26}$, and a N-fluorophore moiety, wherein R$_{24}$ and R$_{25}$ are independently selected from the group consisting of: hydrogen, (C$_1$-C$_{10}$)alkyl, (C$_2$-C$_{10}$)alkenyl, (C$_2$-C$_{10}$) alkynyl and a known ring system comprising from 3 to 14 carbon atoms, the system comprising from 1 to 3 rings, where:

each one of the rings is saturated, partially unsaturated, or aromatic;
the rings are isolated, partially or totally fused, each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$) haloalkyl, and (C$_1$-C$_{10}$)alkyl-O—; and R$_{26}$ is a radical selected from —OR$_{27}$, —(C$_1$-C$_{20}$)alkylC(O)OR$_{28}$, —(C$_1$-C$_{20}$)alkylC(O)R$_{29}$, —(C$_1$-C$_{20}$)alkylOR$_{30}$, and —O(C$_1$-C$_{20}$)CONR$_{31}$R$_{32}$, wherein R$_{27}$ to R$_{32}$ are radicals independently selected from hydrogen, (C$_1$-C$_{10}$) alkyl, (C$_2$-C$_{10}$)alkenyl, and (C$_2$-C$_{10}$)alkenyl and a known ring system comprising from 3 to 14 carbon atoms, the system comprising from 1 to 3 rings, where:
each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$) haloalkyl, and (C$_1$-C$_{10}$)alkyl-O—.

In one embodiment of the second aspect of the invention, the C-terminal group is —COOH and the N-terminal group is —NH$_2$. In another embodiment, the C-terminal group is —CO—NH$_2$ and the N-terminal group is —NHC(O)R$_{26}$, being R$_{26}$ as defined above. In another embodiment, the C-terminal group is —CO—NH$_2$ and the N-terminal group is —NHC(O)R$_{26}$, being R$_{26}$ a radical —(C$_1$-C$_{20}$)alkylC(O) OR$_{28}$. In another embodiment, the C-terminal group is —CO—NH$_2$ and the N-terminal group is —NHC(O)R$_{26}$, being R$_{26}$ a radical —(CH$_2$)$_2$C(O)OH (i.e., succinyl). In one embodiment, v is 1, the C-terminal group is —COOH and the N-terminal group is a —NH$_2$. In another embodiment, v is 1, the C-terminal group is —CO—NH$_2$ and the N-terminal group is —NHC(O)R$_{26}$, being R$_{26}$ as defined above. In another embodiment, v is 1, the C-terminal group is —CO—NH$_2$ and the N-terminal group is —NHC(O)R$_{26}$, being R$_{26}$ a radical —(C$_1$-C$_{20}$)alkylC(O)OR$_{28}$. In another embodiment, v is 1, the C-terminal group is —CO—NH$_2$ and the N-terminal group is —NHC(O)R$_{26}$, being R$_{26}$ a radical —(CH$_2$)$_2$C(O)OH (i.e., succinyl).

In another embodiment of the second aspect of the invention, the peptide or pharmaceutical salt thereof of formula (IV), (IVbis1) or (IVbis2) one wherein one of "t" and "u" is 1. In another embodiment of the second aspect of the invention, the peptide or pharmaceutical salt thereof of formula (IV), (IVbis1) or (IVbis2) one wherein one of "t" and "u" is 1, and the X birradicals of the backbone peptide sequence of formula (IV) or (IVbis), which are not bound to the "L" birradical, are amino acids, provided that at least one of them is selected from the group consisting of: X$_7$ represents an amino acid other than Val, X$_8$ represents an amino acid other than Leu, X$_9$ represents an amino acid other than Thr, and X$_{10}$ represents an amino acid other than Ala.

In this way, in the peptide of formula (IV), (IVbis1) or (IVbis2), or pharmaceutical salt thereof, when "t" is 1 and "u" is 0, the X's birradicals not bound to the backbone of the peptide are X$_8$, X$_{10}$, X$_{11}$ and X$_{12}$, at least one of X$_8$ and X$_{10}$ being selected from: X$_8$ represents an amino acid other than Leu, and X$_{10}$ represents an amino acid other than Ala. Alternatively, in the peptide of formula (IV) or (IVbis1) or (IVbis2), or pharmaceutical salt thereof, when "u" is 1, and "t" is 0 the X's birradicals not bound to the backbone of the peptide are X$_7$, X$_8$, X$_9$, and X$_{11}$, at least one of X$_7$, X$_8$, X$_9$, being selected from the group consisting of: X$_7$ represents an amino acid other than Val, X$_8$ represents an amino acid other than Leu, X$_9$ represents an amino acid other than Thr, and X$_{10}$ represents an amino acid other than Ala.

In another embodiment of the second aspect of the invention, the peptide or pharmaceutical salt thereof of formula (IV), (IVbis1) or (IVbis2) is one wherein one of "t" and "u" is 1. In another embodiment of the second aspect of the invention, the peptide or pharmaceutical salt thereof of formula (IV), (IVbis1) or (IVbis2) is one wherein one of "t" and "u" is 1, and the X birradicals of the backbone peptide sequence of formula (IV), which are not bound to the "L" birradical are D-amino acids, provided that at least one of them is selected from the group consisting of: X$_7$ represents an amino acid other than Val, X$_8$ represents an amino acid other than Leu, X$_9$ represents an amino acid other than Thr, and X$_{10}$ represents an amino acid other than Ala.

In an embodiment of the second aspect of the invention, L corresponds to a birradical of formula (II) wherein one of "a" and "b" are 0. In another embodiment of the second aspect of the invention, "a" and "b" are 0. In another embodiment of the second aspect of the invention, L corresponds to a birradical of formula (II) wherein "c" is comprised from 1 to 6. In another embodiment of the second aspect of the invention, L corresponds to a birradical of formula (II) wherein "c" is 1. In another embodiment of the second aspect of the invention, L corresponds to a compound of formula (II) wherein:
"a" and "b" are 0; and
"c" is 1.

In another embodiment of the second aspect of the invention, L corresponds to a birradical of formula (II) wherein P and Q are the same or different and represent a (C$_1$-C$_{10}$)alkyl. In another embodiment of the second aspect of the invention, L corresponds to a birradical of formula (II) wherein:
"a" and "b" are 0;
"c" is 1; and
P and Q are the same or different and represent a (C$_1$-C$_{10}$)alkyl.

In another embodiment of the second aspect of the invention R$_2$ is selected from the group consisting of: (C$_1$-C$_{10}$)alkyl, (C$_2$-C$_{10}$)alkenyl, and (C$_2$-C$_{10}$)alkynyl. In another embodiment of the second aspect of the invention, R$_2$ is (C$_2$-C$_{10}$)alkenyl. In another embodiment of the first aspect of the invention, R$_2$ is ethylene.

In another embodiment of the second aspect of the invention, the peptide of formula (IV), (IVbis1), or (IVbis2) or a pharmaceutical salt thereof, is one wherein L corresponds to a birradical of formula (II) wherein "a" and "b" are 0; "c" is 1; and R$_2$ is selected from the group consisting of: (C$_1$-C$_{10}$)alkyl, (C$_2$-C$_{10}$)alkenyl, (C$_2$-C$_{10}$)alkynyl, and a known ring system comprising from 3 to 14 carbon atoms, the system comprising from 1 to 3 rings, where:
each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—. In another embodiment of the second aspect of the invention, the peptide of formula (IV), (IVbis1) or (IVbis2), or a pharmaceutical salt thereof, is one wherein L corresponds to a birradical of formula (II) wherein "a" and "b" are 0, "c" is 1; and R$_2$ is (C$_2$-C$_{10}$)alkenyl. In another embodiment of the second aspect of the invention, the peptide of formula (IV), (IVbis1), or (IVbis2) or a pharmaceutical salt thereof, is one wherein L corresponds to a birradical of formula (II) wherein "a" and "b" are 0, "c" is 1, and R$_2$ is ethylene.

In another embodiment of the second aspect of the invention, the peptide of formula (IV), (IVbis1) or (IVbis2), or a pharmaceutical salt thereof, is one wherein L corresponds to a birradical of formula (II) wherein P and Q are the same or different and represent a (C$_1$-C$_{10}$)alkyl; and R$_2$ is selected from the group consisting of: (C$_1$-C$_{10}$)alkyl, (C$_2$-C$_{10}$)alkenyl, (C$_2$-C$_{10}$)alkynyl, and a known ring system comprising from 3 to 14 carbon atoms, the system comprising from 1 to 3 rings, where:
  each one of the rings is saturated, partially unsaturated, or aromatic;
  the rings are isolated, partially or totally fused,
  each one of the members forming the known ring system is selected from the group consisting of: —CH—, —CH$_2$—, —NH—, —N—, —SH—, —S—, and —O—; and
  the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—. In another embodiment of the second aspect of the invention, the peptide of formula (IV), (IVbis1) or (IVbis2), or a pharmaceutical salt thereof, is one wherein L corresponds to a birradical of formula (II) wherein P and Q are the same or different and represent a (C$_1$-C$_{10}$)alkyl; and R$_2$ is (C$_2$-C$_{10}$)alkenyl. In another embodiment of the second aspect of the invention, the peptide of formula (IV), (IVbis1) or (IVbis2), or a pharmaceutical salt thereof, is one wherein L corresponds to a birradical of formula (II) wherein P and Q are the same or different and represent a (C$_1$-C$_{10}$)alkyl, and R$_2$ is ethylene.

In another embodiment of the second aspect of the invention, the peptide of formula (IV), (IVbis1) or (IVbis2), or a pharmaceutical salt thereof, is one wherein L corresponds to a birradical of formula (II) wherein:
  "a" and "b" are 0;
  "c" is 1;
  P and Q are the same or different and represent a (C$_1$-C$_{10}$)alkyl; and
  R$_2$ is selected from the group consisting of: (C$_1$-C$_{10}$)alkyl, (C$_2$-C$_{10}$)alkenyl, (C$_2$-C$_{10}$)alkynyl and a known ring system comprising from 3 to 14 carbon atoms, the system comprising from 1 to 3 rings, where:
    each one of the rings is saturated, partially unsaturated, or aromatic;
    the rings are isolated, partially or totally fused,
    each one of the members forming the known ring system is selected from the group consisting of: —CH—, —CH$_2$—, —NH—, —N—, —SH—, —S—, and —O—; and
    the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—.

In another embodiment of the second aspect of the invention, the peptide of formula (IV), (IVbis1) or (IVbis2), or a pharmaceutical salt thereof, is one wherein L corresponds to a birradical of formula (II) wherein:
  "a" and "b" are 0;
  "c" is 1;
  P and Q are the same or different and represent a (C$_1$-C$_{10}$)alkyl; and
  R$_2$ is (C$_2$-C$_{10}$)alkenyl.

In another embodiment of the second aspect of the invention, the peptide of formula (IV), (IVbis1) or (IVbis2), or a pharmaceutical salt thereof, is one wherein L corresponds to a birradical of formula (II) wherein:
  "a" and "b" are 0;
  "c" is 1;
  P and Q are the same or different and represent a (C$_1$-C$_{10}$)alkyl; and
  R$_2$ is ethylene.

In another embodiment of the second aspect of the invention, the peptide of formula (IV), (IVbis1) or (IVbis2), or a pharmaceutical salt thereof, is one wherein L corresponds to a birradical of formula (II) wherein "a" and "b" are 0; "c" is 1; R$_2$ is selected from the group consisting of: (C$_1$-C$_{10}$)alkyl, (C$_2$-C$_{10}$)alkenyl, (C$_2$-C$_{10}$)alkynyl, and a known ring system comprising from 3 to 14 carbon atoms, the system comprising from 1 to 3 rings, where:
  each one of the rings is saturated, partially unsaturated, or aromatic;
  the rings are isolated, partially or totally fused,
  each one of the members forming the known ring system is selected from the group consisting of: —CH—, —CH$_2$—, —NH—, —N—, —SH—, —S—, and —O—; and
  the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—; and the X birradicals of the backbone peptide sequence of formula (IV), which are not bound to the "L" birradical, are amino acids, provided that at least one of them is selected from the group consisting of: X$_7$ represents an amino acid other than Val, X$_8$ represents an amino acid other than Leu, X$_9$ represents an amino acid other than Thr, and X$_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein "a" and "b" are 0, "c" is 1; R$_2$ is (C$_2$-C$_{10}$)alkenyl; and the X birradicals of the backbone peptide sequence of formula (IV), which are not bound to the "L" birradical, are amino acids, provided that at least one of them is selected from the group consisting of: X$_7$ represents an amino acid other than Val, X$_8$ represents an amino acid other than Leu, X$_9$ represents an amino acid other than Thr, and X$_{10}$ represents an amino acid other than Ala. In another embodiment of the second aspect of the invention, the peptide of formula (IV), (IVbis1) or (IVbis2), or a pharmaceutical salt thereof, is one wherein L corresponds to a birradical of formula (II) wherein "a" and "b" are 0, "c" is 1, R$_2$ is ethylene; and the X birradicals of the backbone peptide sequence of formula (IV), which are not bound to the "L" birradical, are amino acids, provided that at least one of them is selected from the group consisting of: X$_7$ represents an amino acid other than Val, X$_8$ represents an amino acid other than Leu, X$_9$ represents an amino acid other than Thr, and X$_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein P and Q are the same or different and represent a $(C_1-C_{10})$alkyl; $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where:
  each one of the rings is saturated, partially unsaturated, or aromatic;
  the rings are isolated, partially or totally fused,
  each one of the members forming the known ring system is selected from the group consisting of: —CH—, —CH$_2$—, —NH—, —N—, —SH—, —S—, and —O—; and
  the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—; and the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala. In another embodiment of the second aspect of the invention, the peptide of formula (IV), (IVbis1) or (IVbis2), or a pharmaceutical salt thereof, is one wherein L corresponds to a birradical of formula (II) wherein P and Q are the same or different and represent a $(C_1-C_{10})$alkyl; $R_2$ is $(C_2-C_{10})$alkenyl; and the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala. In another embodiment of the second aspect of the invention, the peptide of formula (IV) or (IVbis1) or a pharmaceutical salt thereof, is one wherein L corresponds to a birradical of formula (II) wherein P and Q are the same or different and represent a $(C_1-C_{10})$alkyl, $R_2$ is ethylene; and the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein:
  "a" and "b" are 0;
  "c" is 1;
  P and Q are the same or different and represent a $(C_1-C_{10})$alkyl;
  $R_2$ is selected from the group consisting of: $(C_1-C_{10})$alkyl, $(C_2-C_{10})$alkenyl, $(C_2-C_{10})$alkynyl and a known ring system comprising from 3 to 14 carbon atoms, the system comprising from 1 to 3 rings, where:
    each one of the rings is saturated, partially unsaturated, or aromatic;
    the rings are isolated, partially or totally fused,
    each one of the members forming the known ring system is selected from the group consisting of: —CH—, —CH$_2$—, —NH—, —N—, —SH—, —S—, and —O—; and
    the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—; and
  the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein:
  "a" and "b" are 0;
  "c" is 1;
  P and Q are the same or different and represent a $(C_1-C_{10})$alkyl;
  $R_2$ is $(C_2-C_{10})$alkenyl; and
  X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein:
  "a" and "b" are 0;
  "c" is 1;
  P and Q are the same or different and represent a $(C_1-C_{10})$alkyl;
  $R_2$ is ethylene; and
  the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein "a" and "b" are 0; "c" is 1; $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where:
  each one of the rings is saturated, partially unsaturated, or aromatic;
  the rings are isolated, partially or totally fused,
  each one of the members forming the known ring system is selected from the group consisting of: —CH—, —CH$_2$—, —NH—, —N—, —SH—, —S—, and —O—; and
  the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—; the X birradicals, which are bound to the "L" birradical, are compounds of formula (III), wherein $R_{11}$ is $(C_1-C_{10})$alkyl; and the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala. In another embodiment of the second aspect of the invention, the peptide of formula (IV), (IVbis1) or (IVbis2), or a pharmaceutical salt thereof, is one wherein L corresponds to a birradical of formula (II) wherein "a" and "b" are 0, "c" is 1; $R_2$ is $(C_2-C_{10})$alkenyl; the X birradicals, which are bound to the "L" birradical, are compounds of formula (III), wherein $R_{11}$ is $(C_1-C_{10})$alkyl; and the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein "a" and "b" are 0, "c" is 1, $R_2$ is ethylene; the X birradicals, which are bound to the "L" birradical, are compounds of formula (III), wherein $R_{11}$ is $(C_1-C_{10})$alkyl; and the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein P and Q are the same or different and represent a $(C_1-C_{10})$alkyl; $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where:
  each one of the rings is saturated, partially unsaturated, or aromatic;
  the rings are isolated, partially or totally fused,
  each one of the members forming the known ring system is selected from the group consisting of: —CH—, —CH$_2$—, —NH—, —N—, —SH—, —S—, and —O—; and
  the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—; the X birradicals, which are bound to the "L" birradical, are compounds of formula (III), wherein $R_{11}$ is $(C_1-C_{10})$alkyl; and the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala. In another embodiment of the second aspect of the invention, the peptide of formula (IV), (IVbis1) or (IVbis2), or a pharmaceutical salt thereof, is one wherein L corresponds to a birradical of formula (II) wherein P and Q are the same or different and represent a $(C_1-C_{10})$alkyl; $R_2$ is $(C_2-C_{10})$alkenyl; the X birradicals, which are bound to the "L" birradical, are compounds of formula (III), wherein $R_{11}$ is $(C_1-C_{10})$alkyl; and the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala. In another embodiment of the second aspect of the invention, the peptide of formula (IV), (IVbis1) or (IVbis2), or a pharmaceutical salt thereof, is one wherein L corresponds to a birradical of formula (II) wherein P and Q are the same or different and represent a $(C_1-C_{10})$alkyl, $R_2$ is ethylene; the X birradicals, which are bound to the "L" birradical, are compounds of formula (III), wherein $R_{11}$ is $(C_1-C_{10})$alkyl; and the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein:
  "a" and "b" are 0;
  "c" is 1;
  P and Q are the same or different and represent a $(C_1-C_{10})$alkyl;
  $R_2$ is selected from the group consisting of: $(C_1-C_{10})$alkyl, $(C_2-C_{10})$alkenyl, $(C_2-C_{10})$alkynyl and a known ring system comprising from 3 to 14 carbon atoms, the system comprising from 1 to 3 rings, where:
    each one of the rings is saturated, partially unsaturated, or aromatic;
    the rings are isolated, partially or totally fused,
    each one of the members forming the known ring system is selected from the group consisting of: —CH—, —CH$_2$—, —NH—, —N—, —SH—, —S—, and —O—; and
    the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—;
  the X birradicals, which are bound to the "L" birradical, are compounds of formula (III), wherein $R_{11}$ is $(C_1-C_{10})$alkyl; and
  the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein:
  "a" and "b" are 0;
  "c" is 1;
  P and Q are the same or different and represent a $(C_1-C_{10})$alkyl;
  $R_2$ is $(C_2-C_{10})$alkenyl;
  the X birradicals, which are bound to the "L" birradical, are compounds of formula (III), wherein $R_{11}$ is $(C_1-C_{10})$alkyl; and X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide of formula (IV), (IVbis1) or (IVbis2), or a pharmaceutical salt thereof, is one wherein L corresponds to a birradical of formula (II) wherein:
"a" and "b" are 0;
"c" is 1;
P and Q are the same or different and represent a $(C_1$-$C_{10})$alkyl;
$R_2$ is ethylene;
the X birradicals, which are bound to the "L" birradical, are compounds of formula (III), wherein $R_{11}$ is $(C_1$-$C_{10})$alkyl; and
the X birradicals of the backbone peptide sequence of formula (IV), which are not bound to the "L" birradical, are amino acids, provided that at least one of them is selected from the group consisting of: $X_7$ represents an amino acid other than Val, $X_8$ represents an amino acid other than Leu, $X_9$ represents an amino acid other than Thr, and $X_{10}$ represents an amino acid other than Ala.

In another embodiment of the second aspect of the invention, the peptide or pharmaceutical salt thereof is one wherein "e" and "f" are 1.

In one embodiment of the second aspect of the invention, the peptide or pharmaceutical salt thereof is one where: "t" is 1, and "u" is 0. In another embodiment of the second aspect of the invention, the peptide or pharmaceutical salt thereof is one of formula (IVbis3):

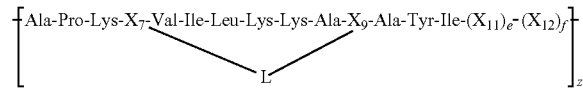
(IVbis3)

In another embodiment of the second aspect of the invention, the peptide or pharmaceutical salt thereof is one of formula (IVbis4):

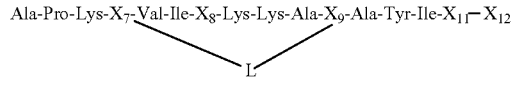
(IVbis4)

In another embodiment of the second aspect of the invention, the peptide or pharmaceutical salt thereof is one of formula (IV), (IVbis1), (IVbis2), (IVbis3) or (IVbis4), where: "t" is 1, "u" is 0, and "e" and "f" are 1. In another embodiment of the second aspect of the invention, the peptide or pharmaceutical salt thereof is one of formula (IV), (IVbis1), (IVbis2), (IVbis3) or (IVbis4) wherein: "t" is 1, "u" is 0, and L corresponds to a birradical of formula (II) wherein: "a" and "b" are 0; and "c" is 1. In another embodiment of the second aspect of the invention, the peptide or pharmaceutical salt thereof is one of formula (IV), (IVbis1), (IVbis2) or (IVbis3) wherein: "t" is 1, "u" is 0, "e" and "f" are 0, and L corresponds to a birradical of formula (II) wherein: "a" and "b" are 0; and "c" is 1. In another embodiment of the second aspect of the invention, the peptide or pharmaceutical salt thereof, is one of formula (IV), (IVbis1), (IVbis2), (IVbis3) or (IVbis4) wherein: "t" is 1, "u" is 0, and L corresponds to a birradical of formula (II) wherein P and Q are the same or different and represent a $(C_1$-$C_{10})$alkyl, $(C_2$-$C_{10})$alkenyl, or $(C_2$-$C_{10})$alkynyl radical, said radicals being substituted or non-substituted In another embodiment of the second aspect of the invention, the peptide or pharmaceutical salt thereof, is one of formula (IV), (IVbis1), (IVbis2), (IVbis3) or (IVbis4) wherein: "t" is 1, "u" is 0, and L corresponds to a birradical of formula (II) wherein P and Q are the same or different and represent a $(C_1$-$C_{10})$alkyl. In another embodiment of the second aspect of the invention, the peptide or pharmaceutical salt thereof, is one of formula (IV), (IVbis1), (IVbis2), (IVbis3) or (IVbis4) wherein: "t" is 1, "u" is 0, "e" and "f" are 1, and L corresponds to a birradical of formula (II) wherein P and Q are the same or different and represent a $(C_1$-$C_{10})$alkyl, $(C_2$-$C_{10})$alkenyl, or $(C_2$-$C_{10})$alkynyl radical. In another embodiment of the second aspect of the invention, the peptide or pharmaceutical salt thereof, is one of formula (IV), (IVbis1), (IVbis2), (IVbis3) or (IVbis4) wherein: "t" is 1, "u" is 0, "e" and "f" are 1, and L corresponds to a birradical of formula (II) wherein P and Q are the same or different and represent a $(C_1$-$C_{10})$alkyl. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; "a" and "b" are 0; "c" is 1; and P and Q are the same or different and represent a $(C_1$-$C_{10})$alkyl. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; "e" and "f" are 1; "a" and "b" are 0; "c" is 1; and P and Q are the same or different and represent a $(C_1$-$C_{10})$alkyl. In another embodiment of the second aspect of the invention, the peptide or pharmaceutical salt thereof is one of formula (IV), (IVbis1), (IVbis2), (IVbis3) or (IVbis4) wherein "t" is 1; "u" is 0; and $R_2$ is selected from the group consisting of: $(C_1$-$C_{10})$alkyl, $(C_2$-$C_{10})$alkenyl, $(C_2$-$C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1$-$C_{10})$alkyl, $(C_1$-$C_{10})$haloalkyl, and $(C_1$-$C_{10})$alkyl-O—. In another embodiment of the second aspect of the invention, the peptide or pharmaceutical salt thereof is one of formula (IV), (IVbis1), (IVbis2), (IVbis3) or (IVbis4) wherein "t" is 1; "u" is 0; "e" and "f" are 0; and $R_2$ is selected from the group consisting of: $(C_1$-$C_{10})$alkyl, $(C_2$-$C_{10})$alkenyl, $(C_2$-$C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1$-$C_{10})$alkyl, $(C_1$-$C_{10})$haloalkyl, and $(C_1$-$C_{10})$alkyl-O—. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; L corresponds to a birradical of formula (II) wherein: "a" and "b" are 0; and "c" is 1; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; "e" and "f" are 0; L corresponds to a birradical of formula (II) wherein: "a" and "b" are 0; and "c" is 1; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—.

In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; L corresponds to a birradical of formula (II) wherein P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; "e" and "f" are 1; L corresponds to a birradical of formula (II) wherein P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; "a" and "b" are 0; "c" is 1; P and Q are the same or different and represent a $(C_1-C_{10})$alkyl, $(C_2-C_{10})$alkenyl, or $(C_2-C_{10})$alkynyl radical and $R_2$ is selected from the group consisting of: $(C_1-C_{10})$alkyl, $(C_2-C_{10})$alkenyl, or $(C_2-C_{10})$alkynyl radical. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; "a" and "b" are 0; "c" is 1; P and Q are the same or different and represent a $(C_1-C_{10})$alkyl; and $R_2$ is selected from the group consisting of: $(C_1-C_{10})$alkyl, $(C_2-C_{10})$alkenyl. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; "e" and "f" are 1; "a" and "b" are 0; "c" is 1; P and Q are the same or different and represent a $(C_1-C_{10})$alkyl; and $R_2$ is selected from the group consisting of: $(C_1-C_{10})$alkyl, $(C_2-C_{10})$alkenyl. In another embodiment of the second aspect of the invention, "t" is 1; "u" is 0; and $R_2$ is $(C_2-C_{10})$alkenyl. In another embodiment of the second aspect of the invention, the peptide or pharmaceutical salt thereof is one of formula (IV), (IVbis1), (IVbis2), (IVbis3) or (IVbis4) wherein "t" is 1; "u" is 0; "e" and "f" are 1; and $R_2$ is $(C_2-C_{10})$alkenyl. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; L corresponds to a birradical of formula (II) wherein: "a" and "b" are 0; and "c" is 1; and $R_2$ is $(C_2-C_{10})$alkenyl. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; "e" and "f" are 1; L corresponds to a birradical of formula (II) wherein: "a" and "b" are 0; and "c" is 1; and $R_2$ is $(C_2-C_{10})$alkenyl. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; L corresponds to a birradical of formula (II) wherein P and Q are the same or different and represent a $(C_1-C_{10})$alkyl; and $R_2$ is $(C_2-C_{10})$alkenyl. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; "e" and "f" are 1; L corresponds to a birradical of formula (II) wherein P and Q are the same or different and represent a $(C_1-C_{10})$alkyl; and $R_2$ is $(C_2-C_{10})$alkenyl. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; "a" and "b" are 0; "c" is 1; P and Q are the same or different and represent a $(C_1-C_{10})$alkyl; and $R_2$ is $(C_2-C_{10})$alkenyl. In another embodiment of the second aspect of the invention, the peptide or pharmaceutical salt thereof is one of formula (IV), (IVbis1), (IVbis2), (IVbis3) or (IVbis4) wherein: "t" is 1; "u" is 0; "e" and "f" are 1; "a" and "b" are 0; "c" is 1; P and Q are the same or different and represent a $(C_1-C_{10})$alkyl; and $R_2$ is $(C_2-C_{10})$alkenyl. In another embodiment of the second aspect of the invention, the peptide or pharmaceutical salt thereof is one of formula (IV), (IVbis1), (IVbis2), (IVbis3) or (IVbis4) wherein "t" is 1; "u" is 0; and $R_2$ is ethylene. In another embodiment of the second aspect of the invention, the peptide or pharmaceutical salt thereof is one of formula (IV), (IVbis1), (IVbis2), (IVbis3) or (IVbis4) wherein "t" is 1; "u" is 0; "e" and "f" are 1; and R₂ is ethylene. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; L corresponds to a birradical of formula (II) wherein: "a" and "b" are 0; and "c" is 1; and R₂ is ethylene. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; "e" and "f" are 1; L corresponds to a birradical of formula (II) wherein: "a" and "b" are 0; and "c" is 1; and R₂ is ethylene. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; L corresponds to a birradical of formula (II) wherein P and Q are the same or different and represent a $(C_1-C_{10})$alkyl; and R₂ is ethylene. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; "e" and "f" are 1; L corresponds to a birradical of formula (II) wherein P and Q are the same or different and represent a $(C_1-C_{10})$alkyl; and R₂ is ethylene. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; "a" and "b" are 0; "c" is 1; P and Q are the same or different and represent a $(C_1-C_{10})$alkyl; and R₂ is ethylene. In another embodiment of the second aspect of the invention, the peptide or pharmaceutical salt thereof, is one of formula (IV), (IVbis1), (IVbis2), (IVbis3) or (IVbis4) wherein: "t" is 1; "u" is 0; "e" and "f" are 1; "a" and "b" are 0; "c" is 1; P and Q are the same or different and represent a $(C_1-C_{10})$alkyl; and R₂ is ethylene. In another embodiment of the second aspect of the invention, the peptide or pharmaceutical salt thereof is one of formula (IV), (IVbis1), (IVbis2), (IVbis3) or (IVbis4) wherein "t" is 1; "u" is 0; "e" and "f" are 1; and "L" birradical is of formula (VII)

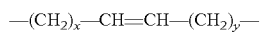

wherein x and y are the same or different and are integer values selected from 1 to 10.

In any of the embodiments provided above or below for the peptide of the second aspect of the invention, where "t" is 1, and "u" is 0 $X_7$ and $X_9$ can be the same. In one embodiment, optionally in combination with any of the embodiments provided above or below for the peptide of formula (IV), (IVbis1), (IVbis2), (IVbis3), (IVbis4) or pharmaceutical salt thereof where "t" is 1 and "u" is 0, $X_7$ and $X_9$ are the same. In one embodiment, optionally in combination with any of the embodiments provided above or below for the peptide of formula (IV), (IVbis1), (IVbis2), (IVbis3), (IVbis4) or pharmaceutical salt thereof where "t" is 1 and "u" is 0, $X_7$ and $X_9$ are the same and correspond to the compound of formula (III) wherein $R_{11}$ represents a $(C_1-C_{10})$alkyl, $(C_2-C_{10})$alkenyl, or $(C_2-C_{10})$alkynyl. In one embodiment, optionally in combination with any of the embodiments provided above or below for the peptide of formula (IV), (IVbis1), (IVbis2), (IVbis3), (IVbis4) or pharmaceutical salt thereof where "t" is 1 and "u" is 0, $X_7$ and $X_9$ are the same and correspond to the compound of formula (III) wherein $R_{11}$ represents a $(C_1-C_{10})$alkyl or $(C_1-C_{10})$alkyl substituted with one or more halogen radicals. In one embodiment, optionally in combination with any of the embodiments provided above or below for the peptide of formula (IV), (IVbis1), (IVbis2), (IVbis3), (IVbis4) or pharmaceutical salt thereof where "t" is 1 and "u" is 0, $X_7$ and $X_9$ are the same and correspond to the compound of formula (III) wherein $R_{11}$ represents a methyl radical:

(IIIbis)

In one embodiment, optionally in combination with any of the embodiments provided above or below for the peptide of formula (IV), (IVbis1) or (IVbis2) or pharmaceutical salt thereof where "t" is 1 and "u" is 0, $X_8$, $X_{10}$, $X_{11}$, and $X_{12}$ are amino acids, provided that at least one of $X_8$ and $X_{10}$ is selected from the group consisting of: $X_8$ represents an amino acid other than Leu, and $X_{10}$ represents an amino acid other than Ala. In one embodiment, optionally in combination with any of the embodiments provided above or below for the peptide of formula (IV), (IVbis1) or (IVbis2) or pharmaceutical salt thereof where "t" is 1 and "u" is 0, $X_8$, $X_{10}$, $X_{11}$, and $X_{12}$ are amino acids, provided that $X_8$ represents an amino acid other than Leu. In one embodiment, optionally in combination with any of the embodiments provided above or below for the peptide of formula (IVbis4) or pharmaceutical salt thereof where "t" is 1 and "u" is 0, and $X_8$ represents an amino acid other than Leu. In one embodiment, optionally in combination with any of the embodiments provided above or below for the peptide of formula (IV), (IVbis1) or (IVbis2) or pharmaceutical salt thereof where "t" is 1 and "u" is 0, $X_8$, $X_{10}$, $X_{11}$, and $X_{12}$ are amino acids, provided that $X_8$ represents a D-amino acid other than Leu. In one embodiment, optionally in combination with any of the embodiments provided above or below for the peptide of formula (IVbis4), or pharmaceutical salt thereof where "t" is 1 and "u" is 0, and $X_8$ represents a D-amino acid other than Leu. In one embodiment, optionally in combination with any of the embodiments provided above or below for the peptide of formula (IV), (IVbis1) or (IVbis2) or pharmaceutical salt thereof where "t" is 1 and "u" is 0, $X_8$, $X_{10}$, $X_{11}$, and $X_{12}$ are amino acids, provided that $X_8$ represents a D-Phe. In one embodiment, optionally in combination with any of the embodiments provided above or below for the peptide of formula (IVbis4) or pharmaceutical salt thereof where "t" is 1 and "u" is 0, and $X_8$ represents a D-Phe.

In one embodiment, optionally in combination with any of the embodiments provided above or below for the peptide of the second aspect of the invention of formula (IV), (IVbis1), (IVbis2), (IVbis3) or (IVbis4), where "t" is 1, and "u" is 0, "e" is 1 and $X_{11}$ represents a non-polar amino acid. In one embodiment, optionally in combination with any of the embodiments provided above or below for the peptide of the second aspect of the invention of formula (IV), (IVbis1), (IVbis2), (IVbis3) or (IVbis4), where "t" is 1, and "u" is 0, "f" is 1 and $X_{12}$ represents a polar neutral amino acid. In one embodiment, optionally in combination with any of the embodiments provided above or below for the peptide of the second aspect of the invention of formula (IV), (IVbis1), (IVbis2), (IVbis3) or (IVbis4), where "t" is 1, and "u" is 0, "e" and "f" are 1, $X_{11}$ represents a non-polar amino acid, and $X_{12}$ represents a polar neutral amino acid. In one embodiment, optionally in combination with any of the embodiments provided above or below for the peptide of the second aspect of the invention, where "t" is 1, and "u" is 0, "e" and "f" are 1, $X_{11}$ represents Leu, and $X_{12}$ represents Ser.

In another embodiment, the peptide of the second aspect of the invention is one of SEQ ID NO: 8 (hereinafter also referred as "S09") and SEQ ID NO: 9 (hereinafter also referred as "S14"):

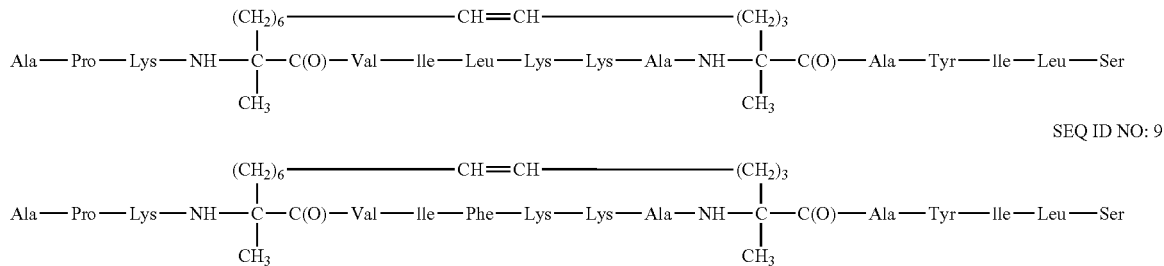

SEQ ID NO: 8

SEQ ID NO: 9

In another embodiment of the second aspect of the invention, the peptide or pharmaceutical salt thereof, is one wherein: "t" is 0; "u" is 1; L corresponds to a birradical of formula (II) wherein P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the second aspect of the invention, the peptide or pharmaceutical salt thereof, is one wherein: "t" is 0; "u" is 1; "e" and "f" are 1; L corresponds to a birradical of formula (II) wherein P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the second aspect of the invention, the peptide or pharmaceutical salt thereof is one wherein: "t" is 0; "u" is 1; "a" and "b" are 0; "c" is 1; P and Q are the same or different and represent a $(C_1-C_{10})$alkyl; and $R_2$ is selected from the group consisting of: $(C_1-C_{10})$alkyl, $(C_2-C_{10})$alkenyl. In another embodiment of the second aspect of the invention, the peptide or pharmaceutical salt thereof is one wherein: "t" is 0; "u" is 1; "e" and "f" are 1; "a" and "b" are 0; "c" is 1; P and Q are the same or different and represent a $(C_1-C_{10})$alkyl; and $R_2$ is selected from the group consisting of: $(C_1-C_{10})$alkyl, $(C_2-C_{10})$alkenyl. In another embodiment of the second aspect of the invention, "t" is 0; "u" is 1; and $R_2$ is $(C_2-C_{10})$alkenyl. In another embodiment of the second aspect of the invention, "t" is 0; "u" is 1; "e" and "f" are 1; and $R_2$ is $(C_2-C_{10})$alkenyl. In another embodiment of the second aspect of the invention, the peptide or pharmaceutical salt thereof is one wherein: "t" is 0; "u" is 1; L corresponds to a birradical of formula (II) wherein: "a" and "b" are 0; and "c" is 1; and $R_2$ is $(C_2-C_{10})$alkenyl. In another embodiment of the second aspect of the invention, the peptide or pharmaceutical salt thereof is one wherein: "t" is 0; "u" is 1; "e" and "f" are 1; L corresponds to a birradical of formula (II) wherein: "a" and "b" are 0; and "c" is 1; and $R_2$ is $(C_2-C_{10})$alkenyl. In another embodiment of the second aspect of the invention, the peptide or pharmaceutical salt thereof is one wherein: "t" is 0; "u" is 1; L corresponds to a birradical of formula (II) wherein P and Q are the same or different and represent a $(C_1-C_{10})$alkyl; and $R_2$ is $(C_2-C_{10})$alkenyl. In another embodiment of the second aspect of the invention, the peptide or pharmaceutical salt thereof is one wherein: "t" is 0; "u" is 1; "e" and "f" are 1; L corresponds to a birradical of formula (II) wherein P and Q are the same or different and represent a $(C_1-C_{10})$alkyl; and $R_2$ is $(C_2-C_{10})$alkenyl. In another embodiment of the second aspect of the invention, the peptide or pharmaceutical salt thereof is one wherein: "t" is 0; "u" is 1; "a" and "b" are 0; "c" is 1; P and Q are the same or different and represent a $(C_1-C_{10})$alkyl; and $R_2$ is $(C_2-C_{10})$alkenyl. In another embodiment of the second aspect of the invention, the peptide or pharmaceutical salt thereof is one wherein: "t" is 0; "u" is 1; "e" and "f" are 1; "a" and "b" are 0; "c" is 1; P and Q are the same or different and represent a $(C_1-C_{10})$alkyl; and $R_2$ is $(C_2-C_{10})$alkenyl. In another embodiment of the second aspect of the invention, "t" is 0; "u" is 1; and $R_2$ is ethylene. In another embodiment of the second aspect of the invention, "t" is 0; "u" is 1; "e" and "f" are 1; and $R_2$ is ethylene. In another embodiment of the second aspect of the invention, the peptide or pharmaceutical salt thereof, is one wherein: "t" is 0; "u" is 1; L corresponds to a birradical of formula (II) wherein: "a" and "b" are 0; and "c" is 1; and $R_2$ is ethylene. In another embodiment of the second aspect of the invention, the peptide or pharmaceutical salt thereof, is one wherein: "t" is 0; "u" is 1; "e" and "f" are 1; L corresponds to a birradical of formula (II) wherein: "a" and "b" are 0; and "c" is 1; and $R_2$ is ethylene. In another embodiment of the second aspect of the invention, the peptide or pharmaceutical salt thereof, is one wherein: "t" is 0; "u" is 1; L corresponds to a birradical of formula (II) wherein P and Q are the same or different and represent a $(C_1-C_{10})$alkyl; and $R_2$ is ethylene. In another embodiment of the second aspect of the invention, the peptide or pharmaceutical salt thereof, is one wherein: "t" is 0; "u" is 1; "e" and "f" are 1; L corresponds to a birradical of formula (II) wherein P and Q are the same or different and represent a $(C_1-C_{10})$alkyl; and $R_2$ is ethylene. In another embodiment of the second aspect of the invention, the peptide or pharmaceutical salt thereof, is one wherein: "t" is 0; "u" is 1; "a" and "b" are 0; "c" is 1; P and Q are the same or different and represent a $(C_1-C_{10})$alkyl; and $R_2$ is ethylene. In another embodiment of the second aspect of the invention, the peptide or pharmaceutical salt thereof, is one wherein: "t" is 0; "u" is 1; "e" and "f" are 1; "a" and "b" are 0; "c" is 1; P and Q are the same or different and represent a $(C_1-C_{10})$alkyl; and $R_2$ is ethylene. In one embodiment, optionally in combination with any of the embodiments provided above or below for the peptide of the second aspect of the invention where "t" is 0, "u" is 1, and "e" and "f" are 1, $X_{10}$ and $X_{12}$ are the same. In one embodiment, optionally in combination with any of the embodiments provided above or below for the peptide of the second aspect of the invention where "t" is 0 and "u" is 1; "e" and "f" are 1, and $X_{10}$ and $X_{12}$ are the same and correspond to the compound of formula (III) wherein $R_{11}$ represents a $(C_1-C_{10})$alkyl, $(C_2-C_{10})$alkenyl, or $(C_2-C_{10})$alkynyl. In one embodiment, optionally in combination with any of the embodiments provided above or below for the peptide of the second aspect of the invention where "t" is 0 and "u" is 1, "e" and "f" are 1, $X_{10}$ and $X_{12}$ are the same and correspond to the compound of formula (III) wherein $R_{11}$ represents a $(C_1-C_{10})$alkyl or $(C_1-C_{10})$alkyl substituted with one or more halogen radicals. In one embodiment, optionally in combination with any of the embodiments provided above or below for the peptide of the second aspect of the invention where "t" is 0 and "u" is 1, "e" and "f" are 1, $X_{10}$ and $X_{12}$ are the same and correspond to the compound of formula (III) wherein $R_{11}$ represents a methyl radical:

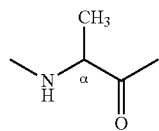

(IIIbis)

In one embodiment, the peptide of the second aspect of the invention is of formula (IV3) (also referred hereinafter as SEQ ID NO: 10 or "S08"):

the group consisting of: $X_7$ represents a d-amino acid other than Val, $X_8$ represents a D-amino acid other than Leu, and $X_9$ represents a D-amino acid other than Thr.

In another embodiment of the peptide or pharmaceutical salt thereof of the second aspect of the invention, "t" and "u" are 0, and $X_7$ to $X_{12}$ are the same or different and represent amino acids, provided that at least three of the radicals $X_7$ to $X_{10}$ are selected from the group consisting of: $X_7$ represents an amino acid other than Val, $X_8$ represents an amino acid other than Leu, $X_9$ represents an amino acid other than Thr, and $X_{10}$ represents an amino acid other than Ala. In another embodiment of the peptide or pharmaceutical salt thereof of the second aspect of the invention, "t" and "u" are 0, "e" and "f" are 0, and $X_7$ to $X_{12}$ are the same or different and represent amino acids, provided that at least three of the radicals $X_7$ to $X_{10}$ are selected from the group consisting of: $X_7$ represents an amino acid other than Val, $X_8$ represents an amino acid other than Leu, $X_9$ represents an amino acid other than Thr, and $X_{10}$ represents an amino acid other than Ala. In another embodiment of the peptide or pharmaceutical salt thereof of the second aspect of the invention, "t" and "u" are 0, and $X_7$ to $X_{12}$ are amino acids, provided that three of $X_7$ to $X_{10}$ are selected from the group consisting of: $X_7$ represents an amino acid other than Val, $X_8$ represents an amino acid other than Leu, $X_9$ represents an amino acid other than Thr, and $X_{10}$ represents an amino acid other than Ala. In another embodiment of the peptide or pharmaceutical salt thereof of the second aspect of the invention, "t" and "u" are 0, "e" and "f" are 0, and $X_7$ to $X_{12}$ are amino acids, provided that three of the radicals $X_7$ to $X_{10}$ are selected from the group consisting of: $X_7$ represents an amino acid other than Val, $X_8$ represents an amino acid other than Leu, $X_9$ represents an amino acid other than Thr, and $X_{10}$ represents an amino acid other than Ala. In another embodiment of the peptide or pharmaceutical salt thereof of the second aspect of the invention, "t" and "u" are 0, and $X_7$ to $X_{12}$ are amino acids, wherein: $X_7$ represents an amino acid other than Val, $X_8$ represents an amino acid other than Leu, $X_9$ represents an amino acid other than Thr, and $X_{10}$ to $X_{12}$ represent any amino acid. In another embodiment of the peptide or pharmaceutical salt thereof of the second aspect of the invention, "t" and "u" are 0, "e" and "f" are 0, and $X_7$ to $X_{12}$ are amino acids, provided that: $X_7$ represents an amino acid other than Val, $X_8$ represents an amino acid other

SEQ ID NO: 10

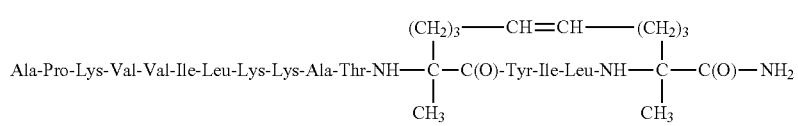

In one embodiment, optionally in combination with any of the embodiments provided above or below for the peptide of the second aspect of the invention where "t" is 0 and "u" is 1, and "e" and "f" are 1, $X_7$, $X_8$, $X_9$, and $X_{11}$ and $X_{12}$ are amino acids, provided that at least one of $X_7$, $X_8$ and $X_9$ are selected from the group consisting of: $X_7$ represents an amino acid other than Val, $X_8$ represents an amino acid other than Leu, and $X_9$ represents an amino acid other than Thr. In one embodiment, optionally in combination with any of the embodiments provided above or below for the peptide of the second aspect of the invention where "t" is 0 and "u" is 1, and "e" and "f" are 1, $X_7$, $X_8$, $X_9$, and $X_{11}$ are amino acids, provided that at least one of $X_7$, $X_8$ and $X_9$ are selected from than Leu, $X_9$ represents an amino acid other than Thr, and $X_{10}$ represents any amino acid.

In one embodiment, optionally in combination with any of the embodiments provided above or below for the peptide or pharmaceutical salt of the second aspect of the invention wherein "t" and "u" are 0, $X_7$ is a D-amino acid other than Val, $X_8$ represents an amino acid other than Leu, and $X_9$ represents an amino acid other than Thr. In one embodiment, optionally in combination with any of the embodiments provided above or below for the peptide or pharmaceutical salt thereof of the second aspect of the invention wherein "t" and "u" are 0, $X_7$ is Leu, $X_8$ represents an amino acid other than Ile, and $X_9$ represents an amino acid other than Thr. In one embodiment, optionally in combination with any of the embodiments provided above or below for the peptide or pharmaceutical salt of the second aspect of the invention wherein "t" and "u" are 0, $X_7$ is an amino acid other than Val, $X_8$ represents a D-amino acid other than Leu, and $X_9$ represents an amino acid other than Thr. In one embodiment, optionally in combination with any of the embodiments provided above or below for the peptide or pharmaceutical salt thereof of the second aspect of the invention wherein "t" and "u" are 0, $X_7$ is an amino acid other than Val, $X_8$ is Phe or Ser, and $X_9$ represents an amino acid other than Thr. In another embodiment, optionally in combination with any of the embodiments provided above or below for the peptide or pharmaceutical salt thereof of the second aspect of the invention wherein "t" and "u" are 0, $X_7$ is an amino acid other than Val, $X_8$ represents an amino acid other than Leu, and $X_9$ represents a D-amino acid other than Thr. In one aspect of the invention, optionally in combination with any of the embodiments provided above or below for the peptide or pharmaceutical salt thereof of the second aspect of the invention wherein "t" and "u" are 0, $X_7$ is an amino acid other than Val, $X_8$ is an amino acid other than Leu, and $X_9$ is Leu.

In another embodiment of the second aspect of the invention, the peptide of the second aspect is one of formula IV5 (hereinafter also referred as SEQ ID NO: 11 (or "L15"):

```
SEQ ID NO: 11
Succ-Ala-Pro-Lys-Ile-Val-Ile-Phe-Lys-Lys-Ala-Leu-
Ala-Tyr-Ile-NH₂
```

In this peptide, the amino group of the residue in N(t) (i.e., Ala) corresponds to a —NH-succinyl group and the carboxylic group of the residue in C(t) (i.e., Ile) corresponds to an amide group, —CO—NH$_2$.

In a further aspect, the present invention provides a peptide or pharmaceutical salt thereof of formula (VIII).

In one embodiment, the peptide or pharmaceutical salt thereof of formula (VIII) is one wherein "e" and "f" are 1. In another embodiment the peptide or pharmaceutical salt thereof of formula (VIII) is one wherein L corresponds to a birradical of formula (II) wherein: "a" and "b" are 0; and "c" is 1. In another embodiment, the peptide or pharmaceutical salt thereof of formula (VIII) is one wherein L corresponds to a birradical of formula (II) wherein: "a" and "b" are 0; and "c" is 1. In another embodiment of the peptide or pharmaceutical salt thereof of formula (VIII), L corresponds to a birradical of formula (II) wherein P and Q are the same or different and represent a $(C_1-C_{10})$alkyl, $(C_2-C_{10})$alkenyl, or $(C_2-C_{10})$alkynyl radical, said radicals being substituted or non-substituted In another embodiment of the peptide or pharmaceutical salt thereof of formula (VIII), L corresponds to a birradical of formula (II) wherein P and Q are the same or different and represent a $(C_1-C_{10})$alkyl. In another embodiment of the peptide or pharmaceutical salt thereof of formula (VIII), "e" and "f" are 1, and L corresponds to a birradical of formula (II) wherein P and Q are the same or different and represent a $(C_1-C_{10})$alkyl, $(C_2-C_{10})$alkenyl, or $(C_2-C_{10})$alkynyl radical. In another embodiment of the peptide or pharmaceutical salt thereof of formula (VIII), "e" and "f" are 1, and L corresponds to a birradical of formula (II) wherein P and Q are the same or different and represent a $(C_1-C_{10})$alkyl. In another embodiment of the peptide or pharmaceutical salt thereof of formula (VIII), "a" and "b" are 0; "c" is 1; and P and Q are the same or different and represent a $(C_1-C_{10})$alkyl. In another embodiment of the peptide or pharmaceutical salt thereof of formula (VIII), "e" and "f" are 1; "a" and "b" are 0; "c" is 1; and P and Q are the same or different and represent a $(C_1-C_{10})$alkyl. In another embodiment of the peptide or pharmaceutical salt thereof of formula (VIII), $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the peptide or pharmaceutical salt thereof of formula (VIII), L corresponds to a birradical of formula (II) wherein: "a" and "b" are 0; and "c" is 1; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the peptide or pharmaceutical salt thereof of formula (VIII), L corresponds to a birradical of formula (II) wherein: "a" and "b" are 0; and "c" is 1; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—.

In another embodiment of the peptide or pharmaceutical salt thereof of formula (VIII), L corresponds to a birradical of formula (II) wherein P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—. In another embodiment of the peptide or pharmaceutical salt thereof of formula (VIII), "e" and "f" are 1; L corresponds to a birradical of formula (II) wherein P and Q are the same or different and represent a $(C_1-C_{10})$alkyl; and $R_2$ is selected from the group consisting of: $(C_1-C_{10})$alkyl, $(C_2-C_{10})$alkenyl, $(C_2-C_{10})$alkynyl, and a known ring system comprising from 3 to 14 carbon atoms, the system comprising from 1 to 3 rings, where: each one of the rings is saturated, partially unsaturated, or aromatic; the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$) alkyl-O—. In another embodiment of the peptide or pharmaceutical salt thereof of formula (VIII), "a" and "b" are 0; "c" is 1; P and Q are the same or different and represent a (C$_1$-C$_{10}$)alkyl, (C$_2$-C$_{10}$)alkenyl, or (C$_2$-C$_{10}$)alkynyl radical and R$_2$ is selected from the group consisting of: (C$_1$-C$_{10}$) alkyl, (C$_2$-C$_{10}$)alkenyl, or (C$_2$-C$_{10}$)alkynyl radical. In another embodiment of the peptide or pharmaceutical salt thereof of formula (VIII), "a" and "b" are 0; "c" is 1; P and Q are the same or different and represent a (C$_1$-C$_{10}$)alkyl; and R$_2$ is selected from the group consisting of: (C$_1$-C$_{10}$) alkyl, (C$_2$-C$_{10}$)alkenyl. In another embodiment of the peptide or pharmaceutical salt thereof of formula (VIII), "e" and "f" are 1; "a" and "b" are 0; "c" is 1; P and Q are the same or different and represent a (C$_1$-C$_{10}$)alkyl; and R$_2$ is selected from the group consisting of: (C$_1$-C$_{10}$)alkyl, (C$_2$-C$_{10}$)alkenyl. In another embodiment of the peptide or pharmaceutical salt thereof of formula (VIII), R$_2$ is (C$_2$-C$_{10}$)alkenyl. In another embodiment of the peptide or pharmaceutical salt thereof of formula (VIII), "e" and "f" are 1; and R$_2$ is (C$_2$-C$_{10}$)alkenyl. In another embodiment of the peptide or pharmaceutical salt thereof of formula (VIII), L corresponds to a birradical of formula (II) wherein: "a" and "b" are 0; and "c" is 1; and R$_2$ is (C$_2$-C$_{10}$)alkenyl. In another embodiment of the peptide or pharmaceutical salt thereof of formula (VIII), "e" and "f" are 1; L corresponds to a birradical of formula (II) wherein: "a" and "b" are 0; and "c" is 1; and R$_2$ is (C$_2$-C$_{10}$)alkenyl. In another embodiment of the peptide or pharmaceutical salt thereof of formula (VIII), L corresponds to a birradical of formula (II) wherein P and Q are the same or different and represent a (C$_1$-C$_{10}$)alkyl; and R$_2$ is (C$_2$-C$_{10}$)alkenyl. In another embodiment of the peptide or pharmaceutical salt thereof of formula (VIII), "e" and "f" are 1; L corresponds to a birradical of formula (II) wherein P and Q are the same or different and represent a (C$_1$-C$_{10}$)alkyl; and R$_2$ is (C$_2$-C$_{10}$)alkenyl. In another embodiment of the peptide or pharmaceutical salt thereof of formula (VIII), "a" and "b" are 0; "c" is 1; P and Q are the same or different and represent a (C$_1$-C$_{10}$)alkyl; and R$_2$ is (C$_2$-C$_{10}$)alkenyl. In another embodiment of the peptide or pharmaceutical salt thereof of formula (VIII), "a" and "b" are 0; "c" is 1; P and Q are the same or different and represent a (C$_1$-C$_{10}$)alkyl; and R$_2$ is (C$_2$-C$_{10}$)alkenyl. In another embodiment of the peptide or pharmaceutical salt thereof of formula (VIII), R$_2$ is ethylene. In another embodiment of the peptide or pharmaceutical salt thereof of formula (VIII), "e" and "f" are 1; and R$_2$ is ethylene. In another embodiment of the peptide or pharmaceutical salt thereof of formula (VIII), L corresponds to a birradical of formula (II) wherein: "a" and "b" are 0; and "c" is 1; and R$_2$ is ethylene. In another embodiment of the peptide or pharmaceutical salt thereof of formula (VIII), "e" and "f" are 1; L corresponds to a birradical of formula (II) wherein: "a" and "b" are 0; and "c" is 1; and R$_2$ is ethylene. In another embodiment of the peptide or pharmaceutical salt thereof of formula (VIII), L corresponds to a birradical of formula (II) wherein P and Q are the same or different and represent a (C$_1$-C$_{10}$)alkyl; and R$_2$ is ethylene. In another embodiment of the peptide or pharmaceutical salt thereof of formula (VIII), "e" and "f" are 1; L corresponds to a birradical of formula (II) wherein P and Q are the same or different and represent a (C$_1$-C$_{10}$)alkyl; and R$_2$ is ethylene. In another embodiment of the peptide or pharmaceutical salt thereof of formula (VIII), "a" and "b" are 0; "c" is 1; P and Q are the same or different and represent a (C$_1$-C$_{10}$)alkyl; and R$_2$ is ethylene. In another embodiment of the peptide or pharmaceutical salt thereof of formula (VIII), "e" and "f" are 1; "a" and "b" are 0; "c" is 1; P and Q are the same or different and represent a (C$_1$-C$_{10}$)alkyl; and R$_2$ is ethylene. In another embodiment of the peptide or pharmaceutical salt thereof of formula (VIII), "e" and "f" are 1; and "L" birradical is of formula (VII)

—(CH$_2$)$_x$—CH=CH—(CH$_2$)$_y$— wherein x and y are the same or different and are integer values selected from 1 to 10.

In any of the embodiments provided above or below for the peptide of formula (VIII) X$_8$ and X$_{13}$ can be the same. In one embodiment, optionally in combination with any of the embodiments provided above or below for the peptide of formula or pharmaceutical salt thereof of formula (VIII), X$_8$ and X$_{13}$ are the same. In one embodiment, optionally in combination with any of the embodiments provided above or below for the peptide of formula (VIII) or pharmaceutical salt thereof, X$_8$ and X$_{13}$ are the same and correspond to the compound of formula (III) wherein R$_{11}$ represents a (C$_1$-C$_{10}$)alkyl, (C$_2$-C$_{10}$)alkenyl, or (C$_2$-C$_{10}$)alkynyl. In one embodiment, optionally in combination with any of the embodiments provided above or below for the peptide of formula (VIII) or pharmaceutical salt thereof, X$_8$ and X$_{13}$ are the same and correspond to the compound of formula (III) wherein R$_{11}$ represents a (C$_1$-C$_{10}$)alkyl or (C$_1$-C$_{10}$)alkyl substituted with one or more halogen radicals. In one embodiment, optionally in combination with any of the embodiments provided above or below for the peptide of formula (VIII) or pharmaceutical salt thereof, X$_8$ and X$_{13}$ are the same and correspond to the compound of formula (III) wherein R$_{11}$ represents a methyl radical:

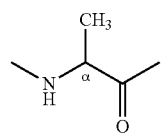

(IIIbis)

In one embodiment, optionally in combination with any of the embodiments provided above or below for a peptide of formula (VIII) or a pharmaceutically acceptable salt thereof, X$_7$ is a non-polar amino acid other than Val. In another embodiment, X$_7$ is Ile.

In another embodiment, optionally in combination with any of the embodiments provided above or below for the peptide of formula (VIII) or a pharmaceutically acceptable salt thereof, X$_9$ is a non-polar amino acid other than Thr. In another embodiment, X$_9$ is Leu.

In one embodiment, optionally in combination with any of the embodiments provided above or below for the peptide of formula (VIII), "e" is 1 and X$_{11}$ represents a non-polar amino acid. In one embodiment, optionally in combination with any of the embodiments provided above or below for the peptide of formula (VIII), "f" is 1 and X$_{12}$ represents a polar neutral amino acid. In one embodiment, optionally in combination with any of the embodiments provided above or below for the peptide of formula (VIII), "e" and "f" are 1, $X_{11}$ represents a non-polar amino acid, and $X_{12}$ represents a non-charged polar amino acid. In one embodiment, optionally in combination with any of the embodiments provided above or below for the peptide of formula (VIII), "e" and "f" are 1, $X_{11}$ represents Leu, and $X_{12}$ represents Ser.

In one embodiment, the peptide or pharmaceutical salt thereof is one of sequence SEQ ID NO: 28 (hereinafter also referred as "S25"):

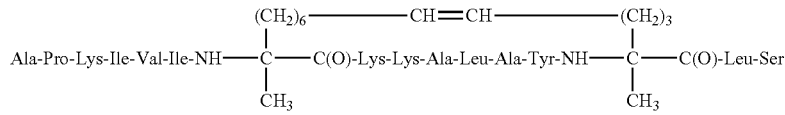

In one embodiment, the peptide or pharmaceutical salt thereof as defined in any of the previous aspects of the invention, or alternatively, a peptide comprising the sequence SEQ ID NO: 12:

```
Ala-Pro-Lys-Val-Val-Ile-Leu-Lys-Lys-Ala-Thr-Ala-
Tyr-Ile
``` or a variant thereof having at least a 85% of identity with SEQ ID NO: 12, or a pharmaceutical salt thereof,
is conjugated to a label.

In the present invention the term "identity" refers to the percentage of residues or bases that are identical in the two sequences when the sequences are optimally aligned. If, in the optimal alignment, a position in a first sequence is occupied by the same amino acid residue or nucleotide as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity= (number of identical positions/total number of positions)× 100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof). For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences.

BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol, v. 215, pages 403-410.

For multiple sequence analysis, the CLUSTAL W program can be used. The CLUSTAL W program desirably is run using "dynamic" (versus "fast") settings. Amino acid sequences are evaluated using a variable set of BLOSUM matrixes depending on the level of identity between the sequences. The CLUSTAL W program and underlying principles of operation are further described in, e.g., Higgins et al., "CLUSTAL V: improved software for multiple sequence alignment", 1992, CABIOS, 8(2), pages 189-191.

A "label" as used herein is a molecule or compound that can be detected by a variety of methods including fluorescence, electrical conductivity, radioactivity, size, and the like. The label may be intrinsically capable of emitting a signal, such as for example fluorescent label that emits light of a particular wavelength following excitation by light of another lower, characteristic wavelength. Alternatively, the label may not be capable of intrinsically emitting a signal but it may be capable of being bound by another compound that does emit a signal. An example of this latter situation is a label such as biotin which itself does not emit a signal but which when bound to labeled avidin or streptavidin molecules can be detected. Other examples of this latter kind of label are ligands that bind specifically to particular receptors. Detectably labeled receptors are allowed to bind to ligand labeled unit specific markers in order to visualize such markers.

Labels that may be used according to the invention include but are not limited to electron spin resonance molecule, a fluorescent molecule, a chemiluminescent molecule, a radioisotope, an enzyme substrate, an enzyme, a biotin molecule, an avidin molecule, an electrical charge transferring molecule, a semiconductor nanocrystal, a semiconductor nanoparticle, a colloid gold nanocrystal, a ligand, a microbead, a magnetic bead, a paramagnetic molecule, a quantum dot, a chromogenic substrate, an affinity molecule, a protein, a peptide, nucleic acid, a carbohydrate, a hapten, an antigen, an antibody, an antibody fragment, and a lipid.

Radioisotopes can be detected with film or charge coupled devices (CCDs), ligands can be detected by binding of a receptor having a fluorescent, chemiluminescent or enzyme tag, and microbeads can be detected using electron or atomic force microscopy.

The conjugation of the label to the peptide can be performed following routine protocols well-known for the skilled in the art.

In one embodiment, the peptide or pharmaceutical salt thereof as defined in any of the previous aspects, or alternatively,
a peptide comprising the sequence SEQ ID NO: 12:

```
Ala-Pro-Lys-Val-Val-Ile-Leu-Lys-Lys-Ala-Thr-Ala-
Tyr-Ile
``` or a variant thereof having at least a 85% of identity with SEQ ID NO: 12, or a pharmaceutical salt thereof,
is conjugated to a cell penetrating peptide.

In the present invention the term "cell penetrating peptide" ("CPP") refers to short peptides that facilitate cellular uptake of various molecular cargo (from nanosize particles to small chemical molecules and large fragments of DNA). The "cargo" is associated to peptides via the C(t) or N(t)-end, either through chemical linkage via covalent bonds or through non-covalent interactions. The function of the CPPs are to deliver the cargo into cells, a process that commonly occurs through endocytosis with the cargo delivered to delivery vectors for use in research and medicine. Current use is limited by a lack of cell specificity in CPP-mediated cargo delivery and insufficient understanding of the modes of their uptake. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. The conjugation of the CPP to the peptide provided in the present invention can be performed following well-known routine protocols, such as solid phase synthesis or solution selective capping. (cf. Copolovici D. M. et al., "Cell-Penetrating Peptides: Design, Synthesis, and Applications", 2014, ACS Nano, 2014, 8 (3), pp 1972-1994).

In one embodiment, the peptide of the invention conjugated to a CPP is selected from the group consisting of:

```
                                        SEQ ID NO: 13
HO(O)C-(CH₂)₂C(O)NH-Arg Arg Arg Arg Arg Arg Arg
Ala Pro Lys Val Val Ile Leu Lys Lys Ala Thr Ala
Tyr-IleNH₂
                                        SEQ ID NO: 14
HO(O)C-(CH₂)₂C(O)NH-Arg Arg Arg Arg Arg Arg Arg
Ala Pro Lys Ile Val Ile Ser Lys Lys Ala Leu Ala
Tyr IleNH₂
                                        SEQ ID NO: 15
HO(O)C-(CH₂)₂C(O)NH-Arg Arg Arg Arg Arg Arg Arg
Ala Pro Lys Ile Val Ile Phe Lys Lys Ala Leu Ala
Tyr IleNH₂
                                        SEQ ID NO: 16
HO(O)C-(CH₂)₂C(O)NH-Arg Gln Ile Lys Ile Trp Phe
Gln Asn Arg Arg Met Lys Trp Lys Lys Ala Pro Lys
Val Val Ile Leu Lys Lys Ala Thr Ala Tyr IleNH₂
                                        SEQ ID NO: 17
HO(O)C-(CH₂)₂C(O)NH-Arg Gln Ile Lys Ile Trp Phe
Gln Asn Arg Arg Met Lys Trp Lys Lys Ala Pro Lys
Ile Val Ile Phe Lys Lys Ala Leu Ala Tyr IleNH₂
```

In these peptides, the amino group of the residue in N(t) (i.e., Arg) corresponds to a —NH-succinyl group and the carboxylic group of the residue in C(t) (i.e., Ile) corresponds to an amide, —CO—NH₂.

The process of preparation of a peptide according to the invention, is one wherein:

(1) when the peptide or pharmaceutical salt thereof is one of formula (I) and "m", "n", "p", and "q" are 0, or the peptide or pharmaceutical salt thereof is one of formula (IV) and "t" and "u" are 0, the process comprises the coupling, by condensation, of the carboxylic group or C-terminus of one amino acid with the amino group or N-terminus of another, this coupling reaction being repeated the number of times required until the desired peptide is obtained; or, alternatively, (2) when the peptide or pharmaceutical salt thereof is one of formula (I) wherein one of "m", "n", "p", and "q" is 1, or the peptide or pharmaceutical salt thereof is one of formula (IV) wherein one of "t" and "u" is 1, or of formula (VIII), the process comprises:

(2.a) the coupling, by condensation, of the corresponding amino acids of the peptide with a compound of formula (Va) and a compound of formula (Vb), which are the ones that suffer the subsequent cyclization step (and thus, contribute to generate the "L" birradical"):

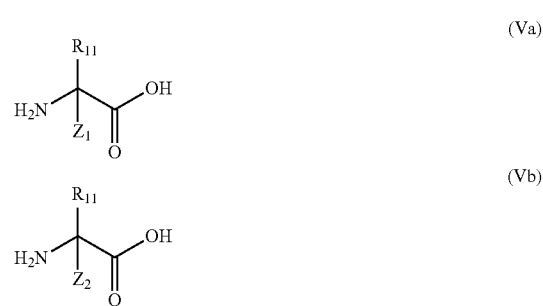

wherein $R_{11}$ is as defined above, $Z_1$ and $Z_2$ are selected from the group consisting of: —SH, —NHR₃₃, —OH, $(C_2-C_{10})$alkyl-SH, $(C_1-C_{10})$alkyl-OH, $(C_1-C_{10})$alkyl-NHR₃₄, C(=O)OH, $(C_1-C_{10})$C(=O)OH, C(=O)NHR₃₅, $(C_1-C_{10})$alkylC(=O)NHR₃₆, C(=O)SH and $(C_1-C_{10})$C(=O)SH, where $R_{33}$, $R_{34}$ $R_{35}$ and $R_{36}$ are monoradicals selected from the group consisting of: hydrogen, $(C_1-C_{10})$alkyl, $(C_2-C_{10})$alkenyl, and $(C_2-C_{10})$alkinyl; and (2.b) a cyclization step comprising the nucleophilic reaction between $Z_1$ and $Z_2$ radicals and a linker of general formula (VI):

where $R_1$, $R_2$, $R_3$ and "c" are as defined above, "a" and "b" are 1, and S and T are radicals, the same or different, selected from the group consisting of halogen, OS(=O)₂R₃₇, OR₃₈, ON(=O)₂, C(=O)-halogen, C(=O)—OS(=O)₂R₃₉ and C(=O)—OR₄₀, where $R_{37}$, $R_{38}$ $R_{39}$ and $R_{40}$ are monoradicals independently selected from the group consisting of: hydrogen, $(C_1-C_{10})$alkyl and a known ring system comprising from 3 to 14 carbon atoms, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH₂—, —NH—, —N—, —SH—, —S—, and —O—; and the ring system is optionally substituted by one or more radicals independently selected from the group consisting of: halogen, —OH, —NO₂, $(C_1-C_{10})$alkyl, $(C_1-C_{10})$haloalkyl, and $(C_1-C_{10})$alkyl-O—; or, alternatively, (3) when the peptide or pharmaceutical salt thereof is one of formula (I) wherein one of "m", "n", "p", and "q" is 1, or the peptide or pharmaceutical salt thereof is one of formula (IV) wherein one of "t" and "u" is 1, the process comprises:

(3.a) the coupling, by condensation, of the corresponding amino acids of the peptide with a compound of formula (Va) and a compound of formula (Vb), which are the ones that suffer the subsequent cyclization step (and thus, contribute to generate the "L" birradical"):

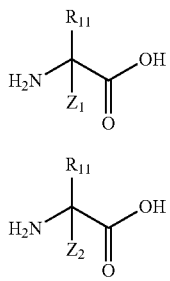
(Va)

(Vb)

wherein $R_{11}$ is as defined above, one of $Z_1$ and $Z_2$ is $(C_2-C_{10})$alkynyl and the other is $(C_2-C_{10})$alkylN$_3$; and (3.b) a cyclization step comprising the condensation of $R_{12}$ and $R'_{12}$ radicals by well-known protocols such as the Cu(I)-mediated Huisgen 1,3-dipolar cycloaddition reaction (a.k.a. a "click" reaction) to generate a 1,4-substituted 1,2,3-triazole bridge (cf. Kolb H. C. et al., "The growing impact of click chemistry on drug discovery.", 2003, Drug Discov Today, 8(24):1128-1137); or, alternatively, (4) when the peptide is one of formula (I) where one of "m", "n", "p", and "q" is 1, or one of formula (IV) where "t" and "u" is 1, the process comprises:

(4.a) the coupling, by condensation, of the corresponding amino acids of the peptide with a compound of formula of formula (Va) and a compound of formula (Vb), which are the ones that suffer the subsequent cyclization step (and thus, contributes to generate the "L" birradical"):

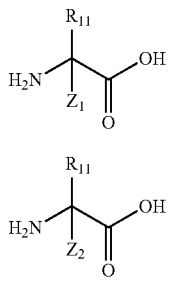
(Va)

(Vb)

wherein $R_{11}$ is as defined above, $Z_1$ and $Z_2$ are the same or different and represent $(C_2-C_{10})$alkenyl; and (4.b) a cyclization step comprising the ring-closed metathesis of $R_{12}$ and $R'_{12}$ (cf. Kim Young-Woo et al., "Synthesis of all-hydrocarbon stapled a-helical peptides by ring-closing olefin metathesis", Nature Protocols, 2011, 6(6), p. 761-771; Scott J. M. et al., "Application of Ring-Closing Metathesis to the Synthesis of Rigidified Amino Acids and Peptides", J. Am. Chem. Soc., 1996, v. 118 (40), pp 9606-9614) performed in solution with a Grubbs (I or II generation) catalyst.

The compounds of formula (Va) and (Vb) are commercially available and are coupled by condensation to the already formed portion of peptide sequence. These compounds of formula (Va) and (Vb) can carry beads for the appropriate solid phase synthesis of the peptide, as well as protecting groups of the carboxy, amino or side-chain. Illustrative non-limitative examples of compounds of formula (Va) and (Vb) are: 2-(2'-propenyl) alanine, 2-(3'-butenyl) glycine, 2-(4'-pentenyl) alanine, 2-(6'-heptenyl)alanine, 2-(7'-octenyl) alanine, allyl-glycine, among others.

Step (a) of the process can be performed in solid phase, following the protocol "deprotection-wash-coupling-wash", but using amino acids as defined above as well as alpha-alpha di-sustituted amino acids of formula (Va) and (Vb) in the order of interest to obtain the desired peptide.

The amino acid coupling by condensation of the carboxylic group of one amino acid with the amino group of another amino acid residue can be performed in solid phase (i.e., on a resin).

The general principle of solid phase peptide synthesis is one of repeated cycles of deprotection-wash-coupling-wash. The free N-terminal amine of a solid-phase attached peptide is coupled to a single N-protected amino acid unit. This unit is then deprotected, revealing a new N-terminal amine to which a further amino acid may be attached. Amino acids have reactive moieties at the N- and C-termini, which facilitates amino acid coupling during synthesis. Many amino acids also have reactive side chain functional groups, which can interact with free termini or other side chain groups during synthesis and peptide elongation and negatively influence yield and purity. To facilitate proper amino acid synthesis with minimal side chain reactivity, chemical groups have been developed to bind to specific amino acid functional groups and block, or protect, the functional group from nonspecific reactions. These protecting groups, while vast in nature, can be separated into three groups, as follows: N-terminal protecting groups, C-terminal protecting groups (mostly used in liquid-phase synthesis), and side chain protecting groups.

For coupling the peptides the carboxyl group is usually activated. This is important for speeding up the reaction. There are two main types of activating groups: carbodiimides and triazolols. However, the use of pentafluorophenyl esters (FDPP, PFPOH]) and BOP-Cl are useful for cyclising peptides.

Purified, individual amino acids are reacted with these protecting groups prior to synthesis and then selectively removed during specific steps of peptide synthesis.

Exemplary resins which may be employed by the present invention include, but are not limited to: (1) alkenyl resins (e.g., REM resin, vinyl sulfone polymer-bound resin, vinyl-polystyrene resin); (2) amine functionalized resins (e.g., amidine resin, N-(4-Benzyloxybenzyl)hydroxylamine polymer bound, (aminomethyl)polystyrene, polymer bound (R)-(+)-a-methylbenzylamine, 2-Chlorotrityl Knorr resin, 2-N-Fmoc-Amino-dibenzocyclohepta-1,4-diene, polymer-bound resin, 4-[4-(1-Fmoc-aminoethyl)-2-methoxy-5-nitrophenoxy]butyramidomethyl-polystyrene resin, 4-Benzyloxybenzylamine, polymer-bound, 4-Carboxybenzenesulfonamide, polymer-bound, Bis(tert-butoxycarbonyl)thiopseudourea, polymer-bound, Dimethylaminomethyl-polystyrene, Fmoc-3-amino-3-(2-nitrophenyl)propionic acid, polymer-bound, N-Methyl aminomethylated polystyrene, PAL resin, Sieber amide resin, tert-Butyl N-(2-mercaptoethyl)carbamate, polymer-bound, Triphenylchloromethane-4-carboxamide polymer bound); (3) benzhydrylamine (BHA) resins (e.g., 2-Chlorobenzhydryl chloride, polymer-bound, HMPB-benzhydrylamine polymer bound, 4-Methylbenzhydrol, polymer-bound, Benzhydryl chloride, polymer-bound, Benzhydrylamine polymer-bound); (4) Br-functionalized resins (e.g., 4-(Benzyloxy) benzyl bromide polymer bound, 4-Bromopolystyrene, Brominated PPOA resin, Brominated Wang resin, Bromoacetal, polymer-bound, Bromopolystyrene, HypoGel® 200 Br, Polystyrene A-Br for peptide synthesis, Selenium bromide, polymer-bound, TentaGel HL-Br, TentaGel MB-Br, TentaGel S-Br, TentaGel S-Br); (5) Chloromethyl resins (e.g., 5-[4-(Chloromethyl)phenyl]pentyl]styrene, polymer-bound, 4-(Benzyloxy)benzyl chloride polymer bound, 4-Methoxybenzhydryl chloride, polymer-bound); (6) CHO-functionalized resins (e.g., (4-Formyl-3-methoxyphenoxymethyl) polystyrene, (4-Formyl-3-methoxyphenoxymethyl) polystyrene, 3-Benzyloxybenzaldehyde, polymer-bound, 4-Benzyloxy-2,6-dimethoxybenzaldehyde, polymer-bound, Formylpolystyrene, HypoGel® 200 CHO, Indole resin, Polystyrene A—CH(OEt)2, TentaGel HL—CH(OEt)2); (7) Cl-functionalized resins (e.g., Benzoyl chloride polymer bound, (chloromethyl)polystyrene, Merrifield's resin); N(8) CO2H functionalized resins (e.g., Carboxyethylpolystryrene, HypoGel® 200 COOH, Polystyrene AM—COOH, TentaGel HL—COOH, TentaGel MB—COOH, TentaGel S—COOH); (9) Hypo-Gel resins (e.g., HypoGel® 200 FMP, HypoGel® 200 PHB, HypoGel® 200 Trt-OH, HypoGel® 200 HMB); (10) 1-functionalized resins (e.g., 4-Iodophenol, polymer-bound, Iodopolystyrene); Janda-Jels™ (JandaJel<ä>-Rink amide, JandaJel-NH2, JandaJel—Cl, JandaJel-4-Mercaptophenol, JandaJel—OH, JandaJel-1-(3-Dimethylaminopropyl)-3-ethylcarbodiimide, JandaJel-1,3,4,6,7,8-hexahydro-2H-pyrimido-[1,2-a]pyrimidine, JandaJel-morpholine, JandaJel-polypyridine, JandaJel-Triphenylphosphine, JandaJel-Wang); (11) MBHA resins (3[4'-(Hydroxymethyl)phenoxy] propionic acid-4-methylbenzhydrylamine resin, 4-(Hydroxymethyl)phenoxyacetic acid polymer-bound to MBHA resin, HMBA-4-methylbenzhydrylamine polymer bound, 4-Methylbenzhydrylamine hydrochloride polymer bound Capacity (amine)); (12) NH2 functionalized resins ((Aminomethyl)polystyrene, (Aminomethyl)polystyrene, HypoGel® 200 NH2, Polystyrene AM-NH2, Polystyrene Microspheres 2-aminoethylated, Polystyrol Microspheres 2-bromoethylated, Polystyrol Microspheres 2-hydroxyethylated, TentaGel HL-NH2, Tentagel M Br, Tentagel M NH2, Tentagel M OH, TentaGel MB-NH2, TentaGel S-NH2, TentaGel S-NH2); (13) OH-functionalized resins (e.g., 4-hydroxymethylbenzoic acid, polymer-bound, Hydroxymethyl Resins, OH-functionalized Wang Resins); (14) oxime resins (e.g., 4-Chlorobenzophenone oxime polymer bound, Benzophenone oxime polymer bound, 4-Methoxybenzophenone oxime polymer bound); (15) PEG resins (e.g., ethylene glycol polymer bound); (16) Boc-/Blz peptide synthesis resins (e.g., Boc-Lys(Boc)-Lys[Boc-Lys(Boc)]-Cys(Acm)-b-Ala-O-PAM resin, Boc-Lys(Fmoc)-Lys[Boc-Lys(Fmoc)]-b-Ala-O-Pam resin, Boc-Lys(Boc)-Lys[Boc-Lys(Boc)]-Lys{Boc-Lys(Boc)-Lys[Boc-Lys(Boc)]}-b-Ala-O-PAM resin, Boc-Lys(Fmoc)-Lys[Boc-Lys(Fmoc)]-Lys[Boc-Lys (Fmoc)-Lys{Boc-Lys(Fmoc)]}-b-Ala-O-PAM resin, Boc-Lys(Boc)-Lys[Boc-Lys(Boc)]-Lys{Boc-Lys(Boc)-Lys[Boc-Lys(Boc)]}-Cys(Acm)-b-Ala-O-PAM resin, Preloaded PAM resins); (17) Fmoc-/t-Bu peptide synthesis resins (e.g., Fmoc-Lys(Fmoc)-Lys[Fmoc-Lys(Fmoc)]-b-Ala-O-Wang resin, Fmoc-Lys(Fmoc)-Lys[Fmoc-Lys(Fmoc)]-Lys{Fmoc-Lys(Fmoc)-Lys[Fmoc-Lys(Fmoc)]}-b-Ala-O-Wang resin, Preloaded TentaGel® S Trityl Resins, Preloaded TentaGel® Resins, Preloaded Trityl Resins, Preloaded Wang Resins, Trityl Resins Preloaded with Amino Alcohols); (19) thiol-functionalized resins (e.g., HypoGel® 200 S-Trt, Polystyrene AM-S-Trityl, TentaGel HL-S-Trityl, TentaGel MB-S-Trityl, TentaGel S-S-Trityl); and (20) Wang resins (e.g., Fmoc-Ala-Wang resin, Fmoc-Arg(Pbf)-Wang resin, Fmoc-Arg(Pmc)-Wang resin, Fmoc-Asn(Trt)-Wang resin, Fmoc-Asp(OtBu)-Wang resin, Fmoc-Cys(Acm)-Wang resin, Fmoc-Cys(StBu)-Wang resin, Fmoc-Cys(Trt) Wang resin, Fmoc-Gln(Trt)-Wang resin, Fmoc-Glu(OtBu)-Wang resin, Fmoc-Gly-Wang resin, Fmoc-His(Trt)-Wang resin, Fmoc-Ile-Wang resin, Fmoc-Leu-Wang resin, Fmoc-Lys(Boc)-Wang resin, Fmoc-Met-Wang resin, Fmoc-D-Met-Wang resin, Fmoc-Phe-Wang resin, Fmoc-Pro-Wang resin, Fmoc-Ser(tBu)-Wang resin, Fmoc-Ser(Trt)-Wang resin, Fmoc-Thr(tBu)-Wang resin, Fmoc-Trp(Boc) Wang resin, Fmoc-Trp-Wang resin, Fmoc-Tyr(tBu)-Wang resin, Fmoc-Val-Wang resin).

"Protecting group" (PG) refers to a grouping of atoms that when attached to a reactive group in a molecule masks, reduces or prevents that reactivity.

Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)

ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, Ntriphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

In case that "m", "n", "p", and "q" are 0 for the peptide of formula (I) or "t" and "u" are 0, for the peptide of formula (IV), the peptides are synthesized in solid-phase as disclosed above.

The present invention also provides a fusion protein comprising any of the peptides provided herein. The fusion comprising will exhibit the activity shown by the peptide of any of the aspects and embodiments provided above. There are routine techniques to fuse the peptide of the invention to another of interest.

In a fourth aspect the present invention provides a pharmaceutical or veterinary composition.

The expression "therapeutically effective amount" as used herein, refers to the amount of a compound that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio. Likewise, the term "veterinary acceptable" means suitable for use in contact with a non-human animal. Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The formulations of the pharmaceutical compositions described herein may be prepared by any method known or hereafter developed in the art of pharmacology. In general, such preparatory methods include the step of bringing the active ingredient into association with a excipient and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered.

Pharmaceutically or veterinary acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters {e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically or veterinary acceptable liposomes emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as polyethoxylated castor oil (e.g. CREMOPHOR™), alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. Alternatively, the preparation can be in the form of liposomes.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The peptides of the invention can be in micro-encapsulated form with one or more excipients as noted above. In one embodiment, the peptides of the invention are formulated in liposomes. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

It will be appreciated that peptides and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive conjugate useful for detecting tumors may be administered concurrently with another agent useful for detecting tumors), or they may achieve different effects (e.g., control of any adverse effects).

The pharmaceutical composition of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies to employ in a combination regimen will take into account compatibility of the desired therapeutics and/or procedures and/or the desired therapeutic effect to be achieved. It will be appreciated that the therapies employed may achieve a desired effect for the same disorder (for example, an inventive polypeptide may be administered concurrently with another biologically active agent used to treat the same disorder), and/or they may achieve different effects (e.g., control of any adverse effects). In will further be appreciated that biologically active agents utilized in this combination may be administered together in a single composition or administered separately in different compositions.

The expression "in combination with" also encompasses the possibility of conjugating (by chemical-physical interactions) the peptide of the invention to any of the further agents mentioned above and below, which can be either a therapeutic agent or an agent for improving the profile of the peptide (such as bioavailability), among others.

In one embodiment, the peptides of the invention are administered in combination with one or more anti-cancer agents. An anti-cancer agent may be, for instance, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX895 if, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'-deoxycoformycin), Semustine (methyl-CCNU), Teniposide (VM-26) or Vindesine sulfate, signal transduction inhibitors (such as MEK, BRAF, AKT, her2, mTOR, and PI3K inhibitors), but it is not so limited.

As it is illustrated below, the peptides of the invention are useful in the treatment of a cancer selected from the group consisting of: leukemia, breast cancer, lung cancer, myeloma, and lymphoma.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

1. Materials and Methods
Synthetic General Procedure
Compounds IDP-L05, IDP-L06, IDP-L08, IDP-L09, IDP-L10, IDP-L11, IDP-L12, IDP-L13, IDP-L14a, IDP-L15, IDP-L16, IDP-L17

Materials were purchased as following: Fmoc-protected α-amino acids (---); Rinkamide MBHA Resin (Tianjin Nankai HECHENG S&T Co., Ltd); HBTU ((2-(1H-benzotriazol-1-yl)-1,1,3,3-tetramethyluronium hexafluorophosphate), GL Biochem); N-methyl morpholine (Sinopharm Chemical Reagent Co., Ltd.); Succinic anhydride (Aladdin); acetonitrile (Xingke Chemical); ninhydrin (Sinopharm Chemical Reagent Co., Ltd.); Piperidine (Vertellus); Dimethylformamide, DMF (Zhejiang jiangshan chemical co., Ltd); trifluoroacetic acid, TFA (Trifluoroacetic acid, Solvay), TIS (Thioanisole, Solvay)

Briefly, the linear polypeptides were synthesized manually using Fmoc based SPPS (solid phase peptides synthesis) on Rink amide MBHA resin as support.

The following protocol was used:
1. The Fmoc protective group was removed with 20% piperidine in DMF.
2. The resin was washed with DMF five times.
3. The subsequent Fmoc-protected amino acid was coupled for 45 min using Fmoc-AA (3 equiv.), HBTU (3 equiv.), and N-methyl morpholine (6 equiv.).
4. The resin was washed with DMF five times. Coupling was checked by ninhydrin test.
5. Repeat from step 1.
6. N-terminal was capped by reacting with succinic anhydride (10 equiv.) and N-methyl morpholine (10 equiv.).

The peptide was cleaved from the resin and deprotected by exposure to solution F (95% TFA, 2.5% water, 2.5% TIS) and lyophilized.

The lyophilized peptides were purified by reverse phase HPLC using a C18 column (see compounds characterization for details). The peptides were identified by LC-MS-ESI. All the mass spectral data for all the compounds are shown below in Table 3.

Compounds IDP-S01, IDP-S02, IDP-S03, IDP-S04, IDP-S08, IDP-S09, IDP-S12, IDP-S13, IDP-S14, IDP-S311, IDP-S-312 and IDP-S313

Materials were purchased as following: Fmoc-protected α-amino acids (include than the olefinic amino acids Fmoc-[(S)-2-(4 pentenyl)alanine]OH, Fmoc-[(R)-2-(4 pentenyl)alanine]OH, Fmoc-[(S)-2-(7 octenyl)alanine]OH, Fmoc-[(R)-2-(4 pentenyl)alanine]OH, 2-(6-chloro-1-H-benzotriazole-1-yl)-1,1,3,3-tetramethylaminium hexafluorophosphate (TBTU), resins, dimethylformamide (DMF), N,N-diisopropylethylamine (DIEA), trifluoroacetic acid (TFA), 1,2-dichloroethane (DCE), Grubbs Ru (IV) catalyst and piperidine were purchased from different suppliers.

Briefly, the linear polypeptides were synthesized with automatic synthesizer using Fmoc solid phase peptide chemistry. Only the coupling with olefinic amino acids was performed manually after removing the resins from the reactor vessel, as disclosed in the previous section The ring-closing metathesis reaction was performed in solution with a first generation Grubbs catalyst after cleaving the linear peptide from the resin, as disclosed by Scott J. M. and colleagues (Scott J. M. et al., "Application of Ring-Closing Metathesis to the Synthesis of Rigidified Amino Acids and Peptides", 1996, J. Am. Chem. Soc., 1996, 118 (40), pp 9606-9614).

The deprotected peptide precipitated with methyl-tert-butyl ether at 4° C. and lyophilized.

The lyophilized peptides were purified by reverse phase HPLC using a C18 column (see compounds characterization for details). The peptides were identified by LC-MS-ESI. All the mass spectral data for all the compounds are shown below in Table 3.

HPLC Conditions:

IDP-L05. The compound was purified by HPLC-RP (C-18 column; Pump A: $H_2O$ with 0.1% TFA; Pump B Acetonitrile with 0.1% TFA) using a linear gradient 20%-40% of B in 20 minutes (R. T.=8,84). Purity grade 96.67% by HPLC;

IDP-L06. The compound was purified by HPLC-RP (C-18 column; Pump A: $H_2O$ with 0.1% TFA; Pump B Acetonitrile with 0.1% TFA) using a linear gradient 18%-38% of B in 30 minutes (R. T.=21.35). Purity grade 95.62% by HPLC;

IDP-L08. The compound was purified by HPLC-RP (C-18 column; Pump A: $H_2O$ with 0.1% TFA; Pump B Acetonitrile with 0.1% TFA) using a linear gradient 22%-42% of B in 30 minutes (R. T.=22.43). Purity grade 98.66% by HPLC;

IDP-L09. The compound was purified by HPLC-RP (C-18 column; Pump A: $H_2O$ with 0.1% TFA; Pump B Acetonitrile with 0.1% TFA) using a linear gradient 22%-42% of B in 20 minutes (R.T.=13.07). Purity grade 95.4% by HPLC;

IDP-L10. The compound was purified by HPLC-RP (C-18 column; Pump A: $H_2O$ with 0.1% TFA; Pump B Acetonitrile with 0.1% TFA) using a linear gradient 18%-38% of B in 30 minutes (R. T.=23.35). Purity grade 95.62% by HPLC;

IDP-L11. The compound was purified by HPLC-RP (C-18 column; Pump A: $H_2O$ with 0.1% TFA; Pump B Acetonitrile with 0.1% TFA) using a linear gradient 18%-38% of B in 30 minutes (R. T.=21.35). Purity grade 95.62% by HPLC;

IDP-L12. The compound was purified by HPLC-RP (C-18 column; Pump A: H2O with 0.1% TFA; Pump B Acetonitrile with 0.1% TFA) using a linear gradient 18%-38% of B in 30 minutes (R. T.=21.35). Purity grade 95.62% by HPLC;

IDP-L13. The compound was purified by HPLC-RP (C-18 column; Pump A: H2O with 0.1% TFA; Pump B Acetonitrile with 0.1% TFA) using a linear gradient 18%-38% of B in 30 minutes (R. T.=21.35). Purity grade 95.62% by HPLC;

IDP-L14a. The compound was purified by HPLC-RP (C-18 column; Pump A: H2O with 0.1% TFA; Pump B Acetonitrile with 0.1% TFA) using a linear gradient 23%-33% of B in 20 minutes (R. T.=5.97). Purity grade 96.49% by HPLC.

IDP-L15. The compound was purified by HPLC-RP (C-18 column; Pump A: H2O with 0.% TFA; Pump B Acetonitrile with 0.1% TFA) using a linear gradient 24%-34% of B in 20 minutes (R. T.=14.52). Purity grade 99.75% by HPLC;

IDP-L16. The compound was purified by HPLC-RP (C-18 column; Pump A: H2O with 0.1% TFA; Pump B Acetonitrile with 0.1% TFA) using a linear gradient 25%-35% of B in 20 minutes (R. T.=8.02). Purity grade 99.03% by HPLC;

IDP-L17. The compound was purified by HPLC-RP (C-18 column; Pump A: H2O with 0.1% TFA; Pump B Acetonitrile with 0.1% TFA) using a linear gradient 25%-35% of B in 20 minutes (R. T.=13.68). Purity grade 98.14% by HPLC;

IDP-S01. The compound was purified by HPLC-RP (C-18 column; Pump A: H2O with 0.1% TFA; Pump B Acetonitrile with 0.1% TFA) using a linear gradient 5%-60% of B in 8 minutes (R. T.=5.01). Purity grade 95.41% by HPLC; IDP-S02. The compound was purified by HPLC-RP (C-18 column; Pump A: H2O with 0.1% TFA; Pump B Acetonitrile with 0.1% TFA) using a linear gradient 0%-100% of B in 20 minutes (R. T.=11.48). Purity grade 94.9% by HPLC;

IDP-S03. The compound was purified by HPLC-RP (C-18 column; Pump A: H2O with 0.1% TFA; Pump B Acetonitrile with 0.1% TFA) using a linear gradient 5%-60% of B in 8 minutes (R. T.=5.62). Purity grade 94.56% by HPLC;

IDP-S04. The compound was purified by HPLC-RP (C-18 column; Pump A: H2O with 0.1% TFA; Pump B Acetonitrile with 0.1% TFA) using a linear gradient 5%-100% of B in 20 minutes (R. T.=11.08). Purity grade 95.5% by HPLC;

IDP-S08. The compound was purified by HPLC-RP (C-18 column; Pump A: H2O with 0.1% TFA; Pump B Acetonitrile with 0.1% TFA) using a linear gradient 5%-60% of B in 8 minutes (R. T.=5.57). Purity grade 96.66% by HPLC;

IDP-S09. The compound was purified by HPLC-RP (C-18 column; Pump A: H2O with 0.1% TFA; Pump B Acetonitrile with 0.1% TFA) using a linear gradient 5%-60% of B in 12 minutes (R. T.=6.55). Purity grade 95.05% by HPLC;

IDP-S12. The compound was purified by HPLC-RP (C-18 column; Pump A: H2O with 0.1% TFA; Pump B Acetonitrile with 0.1% TFA) using a linear gradient 5%-60% of B in 12 minutes (R. T.=6.81.48). Purity grade 97.3% by HPLC;

IDP-S13. The compound was purified by HPLC-RP (C-18 column; Pump A: H2O with 0.1% TFA; Pump B Acetonitrile with 0.1% TFA) using a linear gradient 5%-60% of B in 12 minutes (R. T.=7.18). Purity grade 95.32% by HPLC;

IDP-S14. The compound was purified by HPLC-RP (C-18 column; Pump A: H2O with 0.1% TFA; Pump B Acetonitrile with 0.1% TFA) using a linear gradient 5%-60% of B in 12 minutes (R. T.=7.63). Purity grade 96.67% by HPLC;

IDP-S311. The compound was purified by HPLC-RP (C-18 column; Pump A: H2O with 0.1% TFA; Pump B Acetonitrile with 0.1% TFA) using a linear gradient 5%-60% of B in 12 minutes (R. T.=6.58). Purity grade 96.48% by HPLC;

IDP-S312. The compound was purified by HPLC-RP (C-18 column; Pump A: H2O with 0.1% TFA; Pump B Acetonitrile with 0.1% TFA) using a linear gradient 5%-60% of B in 12 minutes (R. T.=6.81). Purity grade 95.6% by HPLC, and IDP-S313. The compound was purified by HPLC-RP (C-18 column; Pump A: H2O with 0.1% TFA; Pump B Acetonitrile with 0.1% TFA) using a linear gradient 36%-46% of B in 20 minutes (R. T.=9.98). Purity grade 98.20% by HPLC.

TABLE 3 mass characterization

| N. ID | Sequence | | MW (1H) | Mass | Mass | Mass | Mass |
|---|---|---|---|---|---|---|---|
| IDP-L06 | Succ-RRRRRRRAPKVVILKKATAYI-NH2 | calcul. | 2705.7 | 1353.9 | 902.9 | 677.4 | |
| | | found | | 1353.7 | 902.9 | 677.6 | |
| IDP-L09 | Succ-RRRRRRAPKIVIFKKALAYI-NH2 | calcul. | 2765.7 | 1383.9 | 922.9 | 692.4 | |
| | | found | | 1383.7 | 922.9 | 692.6 | |
| IDP-L10 | NELKRSFFALRDQ | calcul. | 1623.8 | 812.9 | 542.3 | 407.0 | |
| | | found | | 813.1 | | | |
| IDP-L11 | RQRRNELKRSFFALRDQ | calcul. | 2220.5 | 1111.3 | 741.2 | 556.1 | |
| | | found | | 1111.4 | 741.7 | | |
| IDP-L12 | RQRRNELKRSFAALRDQ | calcul. | 2244.5 | 1123.3 | 749.2 | 562.1 | |
| | | found | | 1123.4 | 749.3 | 562.4 | |
| IDP-L13 | RQRRNELKRAFAALRDQ | calcul. | 2228.5 | 1115.3 | 743.8 | 558.1 | |
| | | found | | 1115.4 | 743.9 | 558.2 | |
| IDP-L14a | PKIVIFKKALAYI | calcul. | 1503.9 | 753.0 | 502.3 | | |
| | | found | 1504.1 | | | | |
| IDP-L15 | Succ-APKIVIFKKALAYI-NH2 | calcul. | 1675.1 | 838.6 | 559.4 | | |
| | | found | 1675.8 | 838.4 | 559.4 | | |
| IDP-L16 | Succ-RQIKIWFQNRRMKWKKAPKVVILKKATAYI-NH2 | calcul. | 3840.0 | 1921.0 | 1281.0 | 961.0 | 769.0 |
| | | found | | 1282.6 | 962.3 | 770.1 | |
| IDP-L17 | Succ-RQIKIWFQNRRMKWKKAPKIVIFKKALAYI-NH2 | calcul. | 3903.1 | 1952.6 | 1302.0 | 976.8 | 781.6 |
| | | found | | 1302.6 | 977.3 | 782.2 | |
| IDP-S02 | RQRRNXLKRXFAALRDQ-NH2 | calcul. | 2176.5 | 1089.2 | 726.5 | 545.1 | 436.3 |
| | | found | | | 726.9 | 545.3 | 436.5 |
| IDP-S03 | RQRRNXLKRAFAXLRDQ-OH | calcul. | 2220.1 | 1111.1 | 741.0 | 556.0 | 445.0 |
| | | found | | 1111.1 | 741.1 | 556.2 | 445.2 |
| IDP-S04 | RQRRNELKRXFAALRDX-NH2 | calcul. | 2220.1 | 1111.1 | 741.0 | 556.0 | 445.0 |
| | | found | | 111.4 | 741.1 | 556.0 | 445.1 |
| IDP-S09 | APKXVILKKAXAYILS-OH | calcul. | 1807.3 | 904.7 | 603.4 | 452.8 | 362.5 |
| | | found | 1808.2 | 904.5 | 603.4 | | |

TABLE 3-continued mass characterization

| N. ID | Sequence | | MW (1H) | Mass | Mass | Mass | Mass |
|---|---|---|---|---|---|---|---|
| IDP-S12 | RQRRNELKRXFFALRDX-NH2 | calcul. | 2296.7 | 1149.4 | 766.6 | 575.2 | 460.3 |
| | | found | | 1149.1 | 766.8 | 575.4 | 460.6 |
| IDP-S13 | NELKRXFFALRDX-NH2 | calcul. | 1699.7 | 850.9 | 567.6 | | |
| | | found | 1701.2 | 851.0 | 567.8 | | |
| IDP-S14 | APKXVIFKKAXAYILS-OH | calcul. | 1840.9 | 921.5 | 614.6 | | |
| | | found | 1842.3 | 921.5 | 614.9 | | |
| IDP-S311 | RQRRNXLKRAFAXLRD-OH | calcul. | 2091.5 | 1046.8 | 698.2 | 523.9 | 419.3 |
| | | found | | 1044.7 | | | |
| IDP-S2 | QRRNXLKRAFAXLRD-OH | calcul. | 1935.3 | 968.7 | 645.1 | 484.8 | 388.1 |
| | | found | | 966.7 | | | |
| IDP-S313 | RQRRNXLFAXLRDQ-OH | calcul. | 2064.2 | 1033.1 | 689.1 | 517.1 | 413.8 |
| | | found | | | 689.2 | 517.3 | |

Cell Lines:

A549, epithelial (lung cancer), ATCC: CCL-185

HL-60, promyeloblast (acute myelocytic leukemia, AML), ECACC: 98070106

MCF-7, epithelial (breast cancer), ECACC: 86012803

MM.1S, B Lymphoblast (multiple myeloma), ATCC: CRL-2974

RAMOS, B lymphocyte (Burkitt's Lymphoma), ATCC: CRL-1596

BJ, fibroblast (normal skin), ATCC® CRL-2522™

Cell Culture

Cell lines A549, MCF-7 and RAMOS were cultured in incubator under $CO_2$ (6%) at 37° C. in DMEM high glucose (Dulbecco's Modified Eagle Solution, Gibco-BRL 31966-21) medium with 10% fetal bovine serum inactivated (FBS) (Gibco-BRL 10106-169). Cell lines HL-60 and MM.1S were cultured in incubator at 37° C. in RPMI-1640 (Sigma R8758) medium with 10% of fetal bovine serum inactivated (FBS) and 2 mM glutamine (Sigma G7513). Cell lines BJ were cultured in incubator under $CO_2$ (6%) at 37° C. in Eagle's Minimum Essential Medium (Sigma, M-2279) with 10% fetal bovine serum inactivated (FBS) (Gibco-BRL 10106-169).

During the amplification step and the assays adherent cells were rinsed with DPBS (Dulbecco's Phosphate Buffered Saline, Sigma D1283) three times and afterward treated for 5 minutes with trypsin ([0.5 g/ml]/EDTA [0.2 g/ml]) (Gibco-BRL, 15400054) in solution of DPBS at 37° C., and, once detached, transferred in the culturing medium. No-adherent cells were centrifuged and transferred in the culturing medium. Cells were counted in a Neubauer chamber after labelling with Tripan-Blue. Each assay was performed only when the viability was superior to 90%.

Viability Assay

A549, MCF-7 and JB cells were seeded at a density of 5000 cells/well and HL-60, MM.1S and Ramos at 10000 cells/well in 100 μl of medium in 96 well plates. After 24 h, the compounds to be tested were added to calculate the dose/response curve at the starting concentration of 100 μM with serial dilutions (1:1). Controls are the untreated cells. Each experiment was performed in triplicate.

Cells were incubated during 72 h in incubator under $CO_2$ atmosphere at 37° C. Cell viability was measured by means of MTT (3-(4,5-dimethylthiazol-2-yl)-2,5-diphenyltetrazolium bromide) assay, Alamar Blue® (Biosource DAL1100) and Hexosaminidase activity test, consecutively, following manufacturer instructions.

Assay Proceeding Follows:

MTT: 1. Stock solution of MTT (475989 Calbiochem) was 5 mg/ml in PBS 1×. As negative control (experiment noise) 3 wells were treated with 20 μl/well of a solution of SDS 10% in $H_2O$. The same control was used for Alamar Blue/Hexosaminidase. 10 μl/well of MTT solution were added and the plate was incubated for 3-4 hr. The medium was discarded and 100 μl of extracting buffer (PBS 1×, 15% SDS, 50% Na N,N-Dimethylformamide, pH 4.7) were added to each well. Plates were incubated for 16 h at room temperature under orbital shaking. Absorbance at 570 nm was finally measured.

Alamar Blue: 10 μl Alamar Blue solution was added to each well and the plates were incubated for 4 in the incubator. Fluorescence ratio at 535/590 (excitation/emission) was measured in Cytofluor (Millipore) fluorimeter. Blank control was determined by lysis of untreated cells with con 2% of Triton X100, right before adding Alamar Blue solution.

Hexosaminidase activity test: after Alamar Blue lecture, medium was discarded and plates were rinsed once with PBS. 60 μl hexosaminidase substrate (p-nitrophenol-N-acetyl-beta-D-glucosamide 7.5 mM [Sigma N-9376], sodium citrate 0.1 M, pH 5.0, 0.25% Triton X-100) was added to each well and the plates were incubated at 37° C. for 2-5 h, according to the cell type (hexosaminidase activity changes according to the cell type). After incubation time, 90 μl of revealing solution (Glycine 50 mM, pH 10.4; EDTA 5 mM) were added to each well, and absorbance at 410 nM was measured. Blank control was the same as described before.

Statistics

Data analysis was performed calculating the percentage of cell viability normalized vs. the values of negative control, which was considered equal to 100%. The dose/response curve was fitted through the sigmoidal equation dose-response (variable slope) and the $EC_{50}$ values were calculated as follow:

$$Y = \text{Bottom} + (\text{Top} - \text{Bottom})/(1 + 10^{[(\log EC_{50} - X) * \text{HillSlope}]}),$$

where: X is compound concentration (log scale) and Y is the response

Calculations and graphs were conducted using GraphPad Prism (Prism 6 for Windows).

Mechanism of Action—APO-One® Caspase 3/7

Promega Apo-ONE® Homogeneous Caspase-3/7 Assay Kit was used. Cell lines HL-60, MM.1S were seeded at the density of 15000 cells/well in 50 µl of medium in 96-wells opaque black plates with transparent bottom. After 24 h, compounds at the concentration reported in the table 4 were added to the wells.

TABLE 4

| µM | HL60 | MM.1S |
|---|---|---|
| IL09 | 20 | 33 |
| S04 | 26 | 18 |
| S09 | 4.4 | 18 |

Untreated cells were used as negative control and cell treated with Staurosporine (1 µM) was used as positive control. Blank was Apo-ONE® Caspase-3/7 reagent with cell culture medium without cells. Each experiment was performed in triplicate.

Cells were incubated during 4 h, 8 h y 16 h in incubator under $CO_2$ atmosphere at 37° C. Afterwards, 50 µl of Apo-ONE® Caspase-3/7 reagent (rhodamine 110, bis-(N-CBZ-L-aspartyl-L-glutamyl-L-valyl-L-aspartic acid amide; Z-DEVD-R110) were added. Samples were gently mixed using a plate shaker at 300-500 rpm up to read time. Plates were incubated and analyzed from 1 h to 24 h, to determine the optimal incubation period. Fluorescence of each well was measured (excitation/emission, 499 nm/521 nm).

Statistics

The data reported represent the average of three experiments of each condition. Error bar represents standard deviation. Unpaired two-tailed student t test was applied to evaluate the significant difference (p value) between data sets using GraphPad Prism (Prism 6 for Windows).

Annexin V Assay by Flow Cytometry

Miltenyi Biotec Annexin V-FITC Kit was used. To detect apoptosis in early stage Phosphatidylserine in plasmatic membrane localization was measured, though the calcium dependent reaction with Annexine V. Annexin V molecules were labelled with different fluorophores (FITC) and analyzed by FACS. To detect apoptosis in late stage DNA-intercalating agents, such Propidium iodide (PI) were used.

Cells were seeded at a density range of 150000-30000 cells/well in 12 wells plates, and incubated at 37° C. in the incubator under $CO_2$ atmosphere. After 24 h, treatments at 4 h, 8 h, 18 h, 48 h and 72 h were performed in cell lines A549, HL-60 and MM.1S, at $IC_{30}$ and/or $IC_{80}$, with compounds IDP-S09 and IL-09, in cell lines HL-60 and MM.1S with compound IDP-S04 and in cell line A549 with compounds IDP-S02 and IDP-S03. Staurosporine and compound 100258-F4 (Sigma) were used as positive control and reference compound, respectively.

Stability Test

Reagents: ACN LC-MS (Scharlab AC03712500); MeOH LC-MS (Scharlab ME03262500); IPA LC-MS (Scharlab AL03262500); HCOOH (Carlo Erba 405792); DPBS (Lonza BE17-512F); human plasma with EDTAK2 as anticoagulant were provided by Centre d'Investigació de Medicaments located at the Hospital de la Santa Creu i Sant Pau, C/. Sant Antoni Maria Claret 167, Pavelló Sant Frederic, 08025 Barcelona. Plasma was extracted from a healthy patient on 1 Feb. 2015. It was kept at −20° C. until the experiment day.

A calibration curve of eight non-zero concentration levels (from P1 to P8) was prepared in a concentration interval from 5 to 100 µM for S09. One blank sample of DPBS was also included. All calibration samples were analysed in duplicate. Calibration standard samples were prepared by addition of 30 µL of each calibration solution (from P1 to P8 and blank) to 270 µL of human plasma. Samples for incubation were prepared adding 15 µL of 1 mM solution of S09 to 135 µL of human plasma (final concentration 100 µM). 15 samples were prepared. Samples were incubated at 37° C. for 0, 0.5, 2, 6 and 24 h (three replicates were prepared for each incubation time).

An aliquot of 125 µL human plasma sample (blank, calibration standards and incubation samples) were processed using Sirocco™ Protein Precipitation plates (Waters). 375 µL of ACN were added to each well of the Sirocco plate. Then the samples were filtered applying vacuum (8-10 mm Hg) for about 5 minutes. The filtrates were evaporated under a steady stream of nitrogen (40° C.) and reconstituted with 150 µL of MeOH:$H_2O$ 0.1% HCOOH for analysis. Samples were analyzed by UPLC(ACQUITY Ultra Performance LC-MS/MS(API 3000).

UPLC conditions (X-Bridge C18 column; Pump A: H2O with 0.1% formic acid; Pump B Acetonitrile with 0.1% formic acid) using a linear gradient 5%-95% of B in 8 minutes (R. T.=5.95). The mean (out of 3 experiments) of the normalized percentage integrated area corresponding to the peak of S09 at different time are reported in table 11 below.

2. Results 2.1 Efficacy Results

The experimental data are summarized in Tables 5 and 6 below:

TABLE 5 data for peptides of formula (I)

| | Active compound (EC50) | | | Reference compounds | |
|---|---|---|---|---|---|
| Cell line | IDP-S02 | IDP-S03 | IDP-S12 | Int-HI-S6A-F8 | 10058-F4 |
| MM.1S | 17 ± 6 | ≈14 | 22 ± 2 | >100 | >100 |
| HL-60 | 11 ± nd | ≈6.6 | 23 ± 1 | >100 | 54 ± 2 |
| A549 | ≈43 | 34 ± 6 | 50 | >100 | >100 |
| Ramos | 14 ± 7 | ≈13 | 52 ± 2 | >100 | ≈57 |
| MCF7 | 24 ± 2 | 32 ± 5 | 42 ± 2 | >100 | ≈52 |
| JB | >100 | >100 | np | np | np |

| | | Reference compounds | |
|---|---|---|---|
| Cell line | IDP-S04 | Int-HI-S6A-F8 | 10058-F4 |
| MM.1S | 19 ± 1 | >100 | >100 |
| HL-60 | ≈24 | >100 | 54 ± 2 |
| Ramos | ≈64 | >100 | ≈57 |
| MCF7 | ≈60 | >100 | ≈2 |
| JB | >100 | np | np |

TABLE 5 bis

| | | | | Reference compounds | |
|---|---|---|---|---|---|
| Cell | IDP-S311 | IDP-S312 | IDP-S313 | Int-HI-S6A-F8 | 10058-F4 |
| MM.1S | ≈15 | ≈25 | ≈14 | >100 | >100 |

TABLE 6 data for peptides of formula (IV)

| Cell line | IDP-L09 | IDP-S09 | IDP-S14 | Reference compounds Int-HI-S6A-F8 | 10058-F4 |
|---|---|---|---|---|---|
| MM.1S | 25 ± 1 | ≈6.2 | 6.6 ± 0.9 | >100 | >100 |
| HL-60 | 46 ± 6 | 3.5 ± 0.2 | 7.8 ± 0.4 | >100 | 54 ± 2 |
| A549 | 48 ± 5 | 9.4 ± 4.1 | 9.1 ± 0.8 | >100 | >100 |
| Ramos | 28 ± 1 | ≈28 | 55 | >100 | ≈57 |
| MCF7 | ≈28 | 9.0 ± 1 | 3 ± 0.2 | >100 | ≈52 |
| JB | >100 | 47 ± 0.2 | np | np | np |

Reference compounds:
Int-HI-S6A-F8 inhibitor. as a positive control (compounds were purchased from Enzo Technology);
10058-F4 as active reference compounds (purchased from Sigma).

As it can be derived from these data, the peptides of the invention show a better specificity and sensitivity.

In addition to the above, it was found that peptide L10 (SEQ ID NO: 18), L11 (SEQ ID NO: 33), L12 (SEQ ID NO: 19), L13 (SEQ ID NO: 32), and S13 (SEQ ID NO: 4) were inactive. However, when S04 was synthesized, comprising the exact mutation of L12 and the staple in the same positions as in S13, the resulting peptide was surprisingly active in front of several tumor cell lines:

TABLE 6bis comparative data for peptides of formula (I)

| Cell line | Active compound (EC50, uM) | | | | | |
|---|---|---|---|---|---|---|
| | IDP-L10 | IDP-L11 | IDP-L12 | IDP-L13 | IDP-S13 | IDP-S04 |
| MM.1S | >100 | >100 | >100 | >100 | >100 | 19 ± 1 |
| HL-60 | >100 | >100 | >100 | >100 | >100 | ≈24 |
| Ramos | >100 | >100 | >100 | >100 | >100 | ≈64 |
| MCF7 | >100 | >100 | >100 | >100 | >100 | ≈60 |

2.2 APO-One® Caspase 3/7 Results

Region A and B: HL60 and MM.1S cells were incubated with concentrations corresponding to the $IC_{80}$ of compounds IDP-S04 and IDP-S09, as shown in the following table 7:

TABLE 7

| | Concentration (μM) | |
|---|---|---|
| | IDP-S04 | IDP-S09 |
| HL-60 | 26 | 4.4 |
| MM.1S | 18 | 18 |

The response was measured at three incubation times (4 h, 8 h y 16 h). The best condition resulted to be the measurement at 8 h. IDP-S04 induces apoptosis in both cell lines, while IDP-S09 shows a significant effect in MM.1S as shows in FIG. 1.

2.3 Annexin V by FACS Results

IDP-S04 was tested on HL-60 (see table 8) and MM.1S (see table 9) cell lines. Induction of apoptosis was observed in both cell lines after 48 h and 72 h. HL-60 is more sensitive, since the apoptosis is induced at lower concentration ($IC_{30}$). In MM.1S at higher concentration the induction is faster (4-8 h).

IDP-L09 was tested on HL-60 (table 8), MM.1S (table 9) and A459 (table 10) cell lines It shows different behavior according to the cell line. In HL-60 apoptosis induction is significant after 48 h and 72 h at low concentrations ($IC_{30}$), while in MM.1S it induces apoptosis at 8 h, 48 h and 72 h at low concentration ($IC_{30}$) and at 8 h at high concentration ($IC_{80}$). In A549 a fast induction (4 h) is observed, and at 16 h.

IDP-S09 was tested HL-60 (table 8), MM.1S (table 9) and A459 (table 10) cell lines. In HL-60 apoptosis induction is significant after 48 h and 72 h at low concentrations ($IC_{30}$), while in MM.1S, IDP-S09 induces apoptosis at 48 h and 72 h at low concentration ($IC_{30}$) and at 4 h and 8 h at high concentration ($IC_{80}$). Finally, in A549 a fast induction (4 h) is observed, and at high level retained at 16 h, 48 h and 72 h at both concentrations tested.

Also IDP-S02 and IDP-S03 were tested in A549 cell line. In this case apoptosis induction is detected after 4 h at both $IC_{30}$ and $IC_{80}$.

TABLE 8

Percentage of HL-60 gated cells (positive to Annexin V) after treatments with the compounds.

| | Control | IS04 (EC30) | L09 (EC30) | S09 (EC30) |
|---|---|---|---|---|
| HL60 48 h | 100% | 600% | 590% | 300% |
| HL60 72 h | 100% | 430% | 230% | 180% |

TABLE 9

Percentage of MM.1S gated cells (positive to Annexin V) after treatments with the compounds

| | Control | IS04 (EC30) | IS04 (EC80) | L09 (EC30) | L09 (EC80) | S09 (EC30) | S09 (EC80) |
|---|---|---|---|---|---|---|---|
| MM.1S 4 h | 100% | n.t. | 390% | 50% | 50% | 120% | 2000% |
| MM.1S 8 h | 100% | n.t. | 630% | 220% | 310% | 300% | 1800% |
| MM.1S 48 h | 100% | 310% | n.t. | 190% | n.t. | 2300% | n.t. |
| MM.1S 72 h | 100% | 100% | n.t. | 500% | n.t. | 1200% | n.t. |

TABLE 10

Percentage of A549 gated cells (positive to Annexin V) after treatments with the compounds

|  | Control | L09 (EC30) | L09 (EC80) | S09 (EC30) | S09 (EC80) |
|---|---|---|---|---|---|
| A549 4 h | 100% | 900% | 2400% | 2500% | 2500% |
| A549 16 h | 100% | 400% | 950% | 2000% | 1800% |
| A549 48 h | 100% | n.t. | n.t. | 300% | 300% |
| A549 72 h | 100% | n.t. | n.t. | 300% | 450% |

The results reported here indicate that the main mechanism responsible for the activity of the peptides of this invention is the induction of the apoptotic process. The fast and high activation of apoptosis in certain experimental conditions do not exclude a second mechanism with amplify the response for example in MM.1S cell line.

2.4. Stability Results

TABLE 11

| Incubation Time | % Remaining of starting compound (mean) | % Remaining of active metabolyte (mean) |
|---|---|---|
| 0 h | 100 | 0 |
| 2 h | 106 ± 4.9 | 0 |
| 6 h | 90 ± 16 | 0 |
| 24 h | 97 ± 10 | 0 |

From the above data, it can be concluded that the peptides of the invention have a high half-life and stability in plasma.

3. Comparative Test Showing that the Particular Position of the Staple is Critical in the Activity of the Peptides of Formula (IV)

In order to demonstrate that the particular position of the staple in the peptides of formula (IVbis3) was critical in the activity, the inventors compared the activity of the peptide S09 (SEQ ID NO: 8) with versions thereof differing in the position of the staple.

Table 12 lists the peptides synthesized for comparative purposes:

TABLE 12

| Name | Sequence |
|---|---|
| SEQ ID NO. 22 (IDP-S19) | AXKVVILKXATAYILS |
| SEQ ID NO. 23 (IDP-S21) | APKVXILKKATXYILS |
| SEQ ID NO. 24 (IDP-S22) | APKVVXLKKATAXILS |
| SEQ ID NO. 25 (IDP-S23) | APKVVILKXATAYILXV |
| SEQ ID NO. 26 (IDP-S17) | APKVVIXKKATAYXLS |
| SEQ ID NO. 27 (IDP-S18) | APKVVILXKATAYIXS |

The X birradical represents, in all cases, the compound of formula:

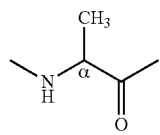

and a L birradical corresponding to —(CH$_2$)$_6$—CH=CH—(CH$_2$)$_3$— links both Xs radicals in each sequence.

The protocol followed was substantially the same as the one already disclosed above.

HPLC Conditions:

IDP-S19. The compound was purified by HPLC-RP (C-18 column; Pump A: H2O with 0.1% TFA; Pump B Acetonitrile with 0.1% TFA) using a linear gradient 47%-57% of B in 20 minutes (R. T.=8.59). Purity grade 95.11% by HPLC;

IDP-S20. The compound was purified by HPLC-RP (C-18 column; Pump A: H2O with 0.1% TFA; Pump B Acetonitrile with 0.1% TFA) using a linear gradient 53%-63% of B in 20 minutes (R. T.=11.75). Purity grade 97.56% by HPLC;

IDP-S21. The compound was purified by HPLC-RP (C-18 column; Pump A: H2O with 0.1% TFA; Pump B Acetonitrile with 0.1% TFA) using a linear gradient 35%-45% of B in 20 minutes (R. T.=12.04). Purity grade 95.12% by HPLC;

IDP-S22. The compound was purified by HPLC-RP (C-18 column; Pump A: H2O with 0.1% TFA; Pump B Acetonitrile with 0.1% TFA) using a linear gradient 40%-50% of B in 20 minutes (R. T.=14.11). Purity grade 95.09% by HPLC;

IDP-S23. The compound was purified by HPLC-RP (C-18 column; Pump A: H2O with 0.1% TFA; Pump B Acetonitrile with 0.1% TFA) using a linear gradient 50%-60% of B in 20 minutes (R. T.=8.80). Purity grade 98.60% by HPLC;

IDP-S17. The compound was purified by HPLC-RP (C-18 column; Pump A: H2O with 0.1% TFA; Pump B Acetonitrile with 0.1% TFA) using a linear gradient 5%-60% of B in 12 minutes (R. T.=7.01). Purity grade 99.11% by HPLC; and IDP-S18. The compound was purified by HPLC-RP (C-18 column; Pump A: H2O with 0.1% TFA; Pump B Acetonitrile with 0.1% TFA) using a linear gradient 5%-60% of B in 12 minutes (R. T.=8.2). Purity grade 97.8% by HPLC.

TABLE 12bis mass characterization

| Name | Sequence | MW (calc) | MW (Found, 1H) |
|---|---|---|---|
| IDP-S19 | AXKVVILKXATAYILS | 1781.01 | 1782.05 |
| IDP-S21 | APKVXILKKATXYILS | 1836.09 | 1837.1 |
| IDP-S22 | APKVVXLKKATAXILS | 1729.97 | 1730.97 |
| IDP-S23 | APKVVILKXATAYILXV | 1890.18 | 1891.3 |
| IDP-S17 | APKVVIXKKATAYXLS | 1780.2 | 1781.2 |
| IDP-S18 | APKVVILXKATAYIXS | 1765.2 | 1766.6 |

Following the same protocol as the one disclosed in previous sections, the following activity data were obtained:

TABLE 13

| Cell line | Compound (EC50, uM) | | | | | | | |
|---|---|---|---|---|---|---|---|---|
| | IDP-L14a | IDP-S09 | IDP-S19 | IDP-S21 | IDP-S22 | IDP-S23 | IDP-S17 | IDP-S18 |
| MM.1S | >100 | ≈6.2 | >100 | >100 | >100 | >100 | >100 | >100 |
| HL-60 | >100 | 3.5 ± 0.2 | >100 | >100 | >100 | >100 | >100 | >100 |
| A549 | >100 | 9.4 ± 4.1 | >100 | >100 | >100 | >100 | >100 | >100 |
| Ramos | >100 | ≈28 | >100 | >100 | >100 | >100 | >100 | >100 |
| MCF7 | >100 | 9.0 ± 1 | >100 | >100 | >100 | >100 | >100 | >100 |

The wild-type sequence became significantly active, surprisingly, only when a staple was made between positions $3^{rd}$ and $10^{th}$ of the sequence, whereas the other versions, based on creating a staple in different positions, did not confer the sequence a significant activity that make them appropriate candidates as anti-cancer agents. This is something surprising because, up to date, staples have been disclosed as providing stability of a peptide. No hint was in the prior art about the possible effect of a staple in the activation of the wild-type peptide sequence SEQ ID NO: 21 which, originally, was inactive.

4. Anti-Cancer Peptides of Formula (VIII)

The peptide of sequence SEQ ID NO: 28 (S25) was synthesized analogously to the protocol disclosed above. The compound was purified by HPLC-RP (C-18 column; Pump A: H2O with 0.1% TFA; Pump B Acetonitrile with 0.1% TFA) using a linear gradient 45%-55% of B in 20 minutes (R. T.=8.39). Purity grade 96.04% by HPLC. Mass characterization: found 904.8 ($M+2H^+$), 603.8 ($M+3H^+$), (calc. 1807.39).

This peptide was tested against several cancer cell lines (the same as used in previous sections and using the same protocols).

The results are summarized in Table 14:

TABLE 14

| Cell line | EC50 IDP-S25 |
|---|---|
| MM.1S | ≈8 |
| HL-60 | ≈8 |
| A549 | ≈45 |
| MCF7 | ≈30 |

5. In vivo Studies

Animals:

CB17-SCID immunosuppressed mice (female) of 6-7 weeks old housed and handled in a pathogen-free zone. They were purchased from Janvier Labs. All experiments were carried out within the facilities of the University of Salamanca.

Groups Studied:

Control: Medium (PBS) i.p. each 12 hours from Monday to Friday.

S03 i.p. each 12 hours from Monday to Friday (in PBS until end point)

S04 15 mg/kg i.p. each 12 hours from Monday to Friday (in PBS until end point)

S09 5 mg/kg i.p. each 12 hours from Monday to Friday (in PBS until end point)

Methods and Follow-Up of the Study:

Subcutaneous Xenograft Model:

The mice were shaved on the right flank and anesthetized by inhalation to decrease their mobility, were inoculated subcutaneously with $3\times10^6$ MM1S cells in 50 μl of RPMI-1640 medium and 50 μl of Corning® Matrigel® Basement Membrane Matrix. When the tumors became palpable (at 30 days), the mice were randomized into the different groups (5 mice in the control group and 4 in the remaining groups) according to the tumor volume. This was estimated by measurements with a caliper of the two tumor diameters and using the following formula of a spheroid: $V=(a \cdot b^2 \cdot \pi)/6$, where a and b correspond to the longest and shortest diameter, respectively. Tumor volume was monitored three times per week.

Survival evaluation: Mice were sacrificed when their tumor diameter reached 2 cm. The time to reach the endpoint criterion was estimated from the day of treatment start. The statistical differences were evaluated using Kaplan-Meier curves with the log rank test. Statistical analyzes were performed using the SPSS-17.0 program.

As can be seen in Table 15, S03, S04 and S09 reduced significantly tumor growth with respect to the control. In particular, at the end-time (when the control in sacrificed) the tumor reduction corresponds to 50% in the case of S03 and S04, and to 70% in the case of S09.

TABLE 15

Comparison of the tumor volume and of the % tumor volume between groups of untreated mice (control) and treated mice with S03, S04 and S09.

| | Group | Day of treatment | | | | | |
|---|---|---|---|---|---|---|---|
| | | 1 | 5 | 10 | 15 | 19 | 26 |
| Tumor Volume | Control | 61.6 | 170.4 | 388.9 | 949.4 | 1529.3 | 3164.3 |
| | IDPS03 5 mg/kg 12 h | 59.0 | 114.1 | 262.1 | 390.7 | 572.6 | 1465.2 |
| | IDPS04 15 mg/kg 12 h | 60.9 | 94.4 | 265.3 | 487.4 | 655.8 | 1546.9 |
| | IDP9 5 mg/kg 12 h | 60.6 | 54.3 | 167.5 | 397.1 | 447.4 | 1010.5 |
| % Tumor Volume | Control | 100 | 276.6 | 631.2 | 1540.7 | 2481.7 | 5134.0 |
| | IDPS03 5 mg/kg 12 h | 100 | 193.2 | 443.9 | 661.6 | 969.5 | 2481.2 |
| | IDPS04 15 mg/kg 12 h | 100 | 154.9 | 435.4 | 799.9 | 1076.2 | 2538.7 |
| | IDPS09 5 mg/kg 12 h | 100 | 89.6 | 276.1 | 654.7 | 737.7 | 1666.1 |

With respect to survival, Tables 16 and 17 show the means of survival and comparison between the different groups. As can be observed, differences in survival were of 9.5 for S03, 5.5 for S04 and 10.5 for S09, reaching statistical significance with respect to the control for S03 and S09.

TABLE 16

Mean survival (95% CI) of the
mice treated with S03, S04 and S09

| Group | Average (days) | IC95% |
|---|---|---|
| Control | 31.0 | 26.0-35.9 |
| S03/12 h | 40.5 | 36.9-44.0 |
| S04/12 h | 36.5 | 30.9-42.0 |
| S09/12 h | 41.5 | 37.2-45.7 |

TABLE 17

Analysis of the statistical differences (Log-Rank)
of the treatments vs. the control

| Group | Comparison* | Chi-square | df | Sig. |
|---|---|---|---|---|
| ControlvsS03_12 h | Log Rank (Mantel-Cox) | 4.102 | 1 | 0.043 |
| ControlvsS04_12 h | Log Rank (Mantel-Cox) | 1.223 | 1 | 0.269 |
| ControlvsS09_12 h | Log Rank (Mantel-Cox) | 5.303 | 1 | 0.021 |

*Chi-square = statistical distribution.
df = degree of freedom;
sig = statistical significance (p < 0.1)

REFERENCES CITED IN THE APPLICATION

Altschul et al., "Basic local alignment search tool", 1990, J. Mol. Biol, v. 215, pages 403-410;
Copolovici D. M. et al., "Cell-Penetrating Peptides: Design, Synthesis, and Applications", 2014, ACS Nano, 2014, 8 (3), pp 1972-1994);
Higgins et al., "CLUSTAL V: improved software for multiple sequence alignment", 1992, CABIOS, 8(2), pages 189-191;
Kim Young-Woo et al., "Synthesis of all-hydrocarbon stapled a-helical peptides by ring-closing olefin metathesis", Nature Protocols, 2011, 6(6), p. 761-771;
Kolb H. C. et al., "The growing impact of click chemistry on drug discovery.", 2003, Drug Discov Today, 8(24):1128-1137); and
Scott J. M. et al., "Application of Ring-Closing Metathesis to the Synthesis of Rigidified Amino Acids and Peptides", J. Am. Chem. Soc., 1996, v. 118 (40), pp 9606-9614.

Clauses

For reasons of clompleteness, various aspects of the invention are set out in the following numbered clauses:

Clause 1. A peptide or a pharmaceutical salt thereof comprising the sequence of formula (I)

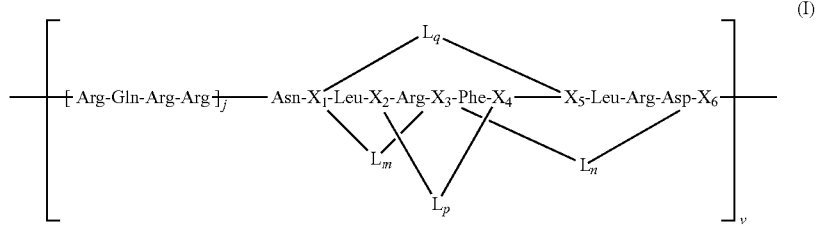

(I)

wherein
m, n, p, and q is 0 or 1,
j is 0 or 1, and
v is comprised from 1 to 10, and wherein
when one of "m", "n", "p", and "q" is 1, then the others are 0 and L corresponds to a dirradical of formula (II)

—P—[(R$_1$)$_a$—(R$_2$)—(R$_3$)$_b$]$_c$-Q-    (II)

"a" and "b" are the same or different and are 0 or 1;
"c" is comprised from 1 to 10;
R$_1$ and R$_3$ are dirradicals independently selected from the group consisting of: (C$_1$-C$_{10}$)alkyl, (C$_2$-C$_{10}$)alkenyl, (C$_2$-C$_{10}$)alkynyl, (C$_1$-C$_{10}$)alkyl-O—(C$_1$-C$_{10}$)alkyl, (C$_1$-C$_{10}$)alkyl-C(=O)—(C$_1$-C$_{10}$)alkyl, (C$_1$-C$_{10}$)alkyl-O—C(O)—(C$_1$-C$_{10}$)alkyl, (C$_1$-C$_{10}$)alkyl-C(O)—NR$_8$—(C$_1$-C$_{10}$)alkyl, (C$_1$-C$_{10}$)alkyl-S—(C$_1$-C$_{10}$)alkyl, (C$_1$-C$_{10}$)alkyl-SR$_9$—(C$_1$-C$_{10}$)alkyl, (C$_1$-C$_{10}$)alkyl-S(=O)$_2$—(C$_1$-C$_{10}$)alkyl, (C$_1$-C$_{10}$)alkyl-S(=O)—(C$_1$-C$_{10}$)alkyl, (C$_1$-C$_{10}$)alkyl-O—S(=O)$_2$—O—(C$_1$-C$_{10}$)alkyl, and (C$_1$-C$_{10}$)alkyl-NR$_{10}$—(C$_1$-C$_{10}$)alkyl;
R$_2$ is a dirradical selected from the group consisting of: —O—, C(=O), C(=O)R$_4$, C(=O)NR$_5$, C(=O)O, S(=O), S(=O)$_2$, S(R$_6$), N(R$_7$), (C$_1$-C$_{10}$)alkyl, (C$_2$-C$_{10}$)alkenyl, (C$_2$-C$_{10}$)alkynyl, NR$_{13}$R$_{14}$, —NH—NH—, —N=N—, —S—S—, and a known ring system comprising from 3 to 14 carbon atoms, the system comprising from 1 to 3 rings, where:
each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—;
R$_4$, R$_5$, R$_6$, R$_7$, R$_8$, R$_9$, R$_{10}$, R$_{13}$, and R$_{14}$ are monoradicals selected from the group consisting of: hydrogen, (C$_1$-C$_{10}$)alkyl, (C$_2$-C$_{10}$)alkenyl, and (C$_2$-C$_{10}$)alkynyl;
P and Q are dirradicals, the same or different, provided that when "a" and "b" are 0, or alternatively one of "a" and "b" is 0, then P and Q have a meaning different from R$_2$ radical, said P and Q dirradicals being selected from the group consisting of: (C$_1$-C$_{10}$)alkyl, (C$_2$-C$_{10}$)alkenyl, and (C$_2$-C$_{10}$)alkynyl; or, alternatively, when "a" and "b" are 0, or alternatively one of "a" and "b" is 0, then P and Q are C(=O), and R$_2$ is selected from the group consisting of: —O—, S(R$_6$), N(R$_7$), (C$_1$-C$_{10}$)alkyl, (C$_2$-C$_{10}$)alkenyl, (C$_2$-C$_{10}$)alkynyl, —NR$_{13}$R$_{14}$, —NH—NH—, —N=N—, —S—S—, and a known ring system comprising from 3 to 14 carbon atoms, the system comprising from 1 to 3 rings, where:
each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—;
when both "a" and "b", are 1, then P and Q are selected from the group consisting of: —S—, (C$_1$-C$_{10}$)alkyl-S—, —NR'$_{10}$—, (C$_1$-C$_{10}$)alkyl-NR'$_{10}$, —O—, (C$_1$-C$_{10}$)-alkyl-O—, —C(=O), (C$_1$-C$_{10}$)alkyl-C(=O)—, —C(=O)O, (C$_1$-C$_{10}$)alkylC(=O)O—, C(=O)N—, (C$_1$-C$_{10}$)alkylC(=O)—, C(=O)S— and (C$_1$-C$_{10}$)alkyl-C(=O)S— being R'$_{10}$ a radical selected from the group consisting of: hydrogen, (C$_1$-C$_{10}$)alkyl, (C$_2$-C$_{10}$)alkenyl, and (C$_1$-C$_{10}$)alkynyl;
the L birradical being bound to the backbone of the peptide sequence of formula (I) via X$_1$ and X$_3$ birradicals, or alternatively via X$_1$ and X$_5$ birradicals, or alternatively via X$_2$ and X$_4$ birradicals, or alternatively via X$_3$ and X$_6$ birradicals,
the X birradicals which are bound to L birradical having the same or different meaning and being of formula (III):

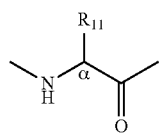

(III)

wherein
the L birradical binds to the X birradical of formula (III) via the alpha carbon atom;
R$_{11}$ is a monoradical selected from the group consisting of: (C$_1$-C$_{10}$)alkyl, (C$_2$-C$_{10}$)alkenyl, (C$_2$-C$_{10}$)alkynyl, (C$_1$-C$_{10}$)alkyl-O—(C$_1$-C$_{10}$)alkyl, (C$_1$-C$_{10}$)alkyl-C(=O)—(C$_1$-C$_{10}$)alkyl, (C$_1$-C$_{10}$)alkyl-O—C(O)—(C$_1$-C$_{10}$)alkyl, (C$_1$-C$_{10}$)alkyl-C(O)—NR$_8$—(C$_1$-C$_{10}$)alkyl, (C$_1$-C$_{10}$)alkyl-S—(C$_1$-C$_{10}$)alkyl, (C$_1$-C$_{10}$)alkyl-SR$_9$—(C$_1$-C$_{10}$)alkyl, (C$_1$-C$_{10}$)alkyl-S(=O)$_2$—(C$_1$-C$_{10}$)alkyl, (C$_1$-C$_{10}$)alkyl-S(=O)—(C$_1$-C$_{10}$)alkyl, (C$_1$-C$_{10}$)alkyl-O—S(=O)$_2$—O—(C$_1$-C$_{10}$)alkyl, (C$_1$-C$_{10}$)alkyl-NR$_{10}$—(C$_1$-C$_{10}$)alkyl, each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—,
and the other X birradicals of the backbone peptide sequence of formula (I), which are not bound to the "L" birradical, are the same or different and represent amino acids;
or, alternatively,
when m, n, p, and q are 0, then X$_1$ to X$_6$ are the same or different and represent amino acids, provided that at least three of the radicals X$_1$ to X$_6$ are selected from the group consisting of:
X$_1$ represents an amino acid other than Glu,
X$_2$ represents an amino acid other than Lys,
X$_3$ represents an amino acid other than Ser,
X$_4$ represents an amino acid other than Phe,
X$_5$ represents an amino acid other than Ala, and
X$_6$ represents an amino acid other than Gln.
wherein:
the (C$_1$-C$_{10}$)alkyl, (C$_2$-C$_{10}$)alkenyl, and (C$_2$-C$_{10}$)alkynyl are non-substituted or substituted,
"substituted (C$_1$-C$_{10}$)alkyl" means that the (C$_1$-C$_{10}$)alkyl is substituted by one or more radicals selected from the group consisting of:
halogen, —OR'$_{11}$, —NO$_2$, —NR'$_{11}$R$_{12}$, —SR'$_{11}$, —SO$_2$R'$_{11}$, —CO$_2$R'$_{11}$, and (C$_1$-C$_{10}$)alkyl-O—, being R'$_{11}$ and R$_{12}$ the same or different and selected from the group consisting of: —H, (C$_1$-C$_{10}$)alkyl, (C$_2$-C$_{10}$)alkenyl, and (C$_1$-C$_{10}$)alkynyl;
"substituted (C$_2$-C$_{10}$)alkenyl" means that the (C$_2$-C$_{10}$)alkenyl is substituted by one or more radicals selected from the group consisting of:
halogen, —OR'$_{11}$, —NO$_2$, —NR'$_{11}$R$_{12}$, —SR'$_{11}$, —SO$_2$R'$_{11}$, —CO$_2$R'$_{11}$, and (C$_1$-C$_{10}$)alkyl-O—, being R'$_{11}$ and R$_{12}$ the same or different and selected from the group consisting of: —H, (C$_1$-C$_{10}$)alkyl, (C$_2$-C$_{10}$)alkenyl, and (C$_1$-C$_{10}$)alkynyl; and
"substituted (C$_2$-C$_{10}$)alkynyl" means that the (C$_2$-C$_{10}$)alkynyl is substituted by one or more radicals selected from the group consisting of:
halogen, —OR'$_{11}$, —NO$_2$, —NR'$_{11}$R$_{12}$, —SR'$_{11}$, —SO$_2$R'$_{11}$, —CO$_2$R'$_{11}$, and (C$_1$-C$_{10}$)alkyl-O—, being R'$_{11}$ and R$_{12}$ the same or different and selected from the group consisting of: —H, (C$_1$-C$_{10}$)alkyl, (C$_2$-C$_{10}$)alkenyl, and (C$_1$-C$_{10}$)alkynyl.
Clause 2. A peptide or a pharmaceutical salt thereof comprising the sequence of formula (IV):

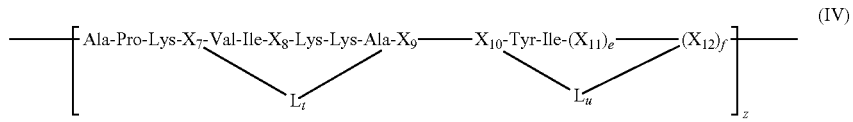

(IV)

and a known ring system comprising from 3 to 14 carbon atoms, the system comprising from 1 to 3 rings, where:

wherein
"t" and "u" are 0 or 1,
"e" and "f" are comprised from 0 to 10, and z is comprised from 1 to 10, and
wherein
when one of "t" and "u" is 1, then
the other is 0,
L corresponds to a dirradical of formula (II)

—P—[(R$_1$)$_a$—(R$_2$)—(R$_3$)$_b$]$_c$-Q- (II)

"a" and "b" are the same or different and are 0 or 1;
"c" is comprised from 1 to 10;
R$_1$ and R$_3$ are dirradicals independently selected from the group consisting of: (C$_1$-C$_{10}$)alkyl, (C$_2$-C$_{10}$)alkenyl, (C$_2$-C$_{10}$)alkynyl, (C$_1$-C$_{10}$)alkyl-O—(C$_1$-C$_{10}$)alkyl, (C$_1$-C$_{10}$)alkyl-C(=O)—(C$_1$-C$_{10}$)alkyl, (C$_1$-C$_{10}$)alkyl-O—C(O)—(C$_1$-C$_{10}$)alkyl, (C$_1$-C$_{10}$)alkyl-C(O)—NR$_8$—(C$_1$-C$_{10}$)alkyl, (C$_1$-C$_{10}$)alkyl-S—(C$_1$-C$_{10}$)alkyl, (C$_1$-C$_{10}$)alkyl-SR$_9$—(C$_1$-C$_{10}$)alkyl, (C$_1$-C$_{10}$)alkyl-S(=O)$_2$—(C$_1$-C$_{10}$)alkyl, (C$_1$-C$_{10}$)alkyl-S(=O)—(C$_1$-C$_{10}$)alkyl, (C$_1$-C$_{10}$)alkyl-O—S(=O)$_2$—O—(C$_1$-C$_{10}$)alkyl, (C$_1$-C$_{10}$)alkyl-NR$_{10}$—(C$_1$-C$_{10}$)alkyl;
R$_2$ is a dirradical selected from the group consisting of: O, C(=O), C(=O)R$_4$, C(=O)NR$_5$, C(=O)O, S(=O), S(=O)$_2$, S(R$_6$), N(R$_7$), (C$_1$-C$_{10}$)alkyl, (C$_2$-C$_{10}$)alkenyl, (C$_2$-C$_{10}$)alkynyl, NR$_{13}$R$_{14}$, —NH—NH—, —N=N—, —S—S—, and a known ring system comprising from 3 to 14 carbon atoms, the system comprising from 1 to 3 rings, where:
each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—;
R$_4$, R$_5$, R$_6$, R$_7$, R$_8$, R$_9$, R$_{10}$, R$_{13}$, and R$_{14}$ are monoradicals selected from the group consisting of: hydrogen, (C$_1$-C$_{10}$)alkyl, (C$_2$-C$_{10}$)alkenyl, and (C$_2$-C$_{10}$)alkynyl;
when "a" and "b" are 0, or alternatively one of "a" and "b" is 0, then P and Q have a meaning different from R$_2$ radical, said P and Q dirradicals being selected from the group consisting of: (C$_1$-C$_{10}$)alkyl, (C$_2$-C$_{10}$)alkenyl, and (C$_2$-C$_{10}$)alkynyl; or, alternatively,
when "a" and "b" are 0, or alternatively one of "a" and "b" is 0, then P and Q are C(=O) and R$_2$ is selected from the group consisting of: —O—, S(R$_6$), N(R$_7$), (C$_1$-C$_{10}$)alkyl, (C$_2$-C$_{10}$)alkenyl, (C$_2$-C$_{10}$)alkynyl, NR$_{13}$R$_{14}$, —NH—NH—, —N=N—, —S—S—, and a known ring system comprising from 3 to 14 carbon atoms, the system comprising from 1 to 3 rings, where:
each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—; or, alternatively,
when both "a" and "b", are 1, then P and Q are selected from the group consisting of: —S—, (C$_1$-C$_{10}$)alkyl-S—, —NR'$_{10}$—, (C$_1$-C$_{10}$)alkyl-NR'$_{10'}$, —O—, (C$_1$-C$_{10}$)-alkyl-O—, —C(=O), (C$_1$-C$_{10}$)alkyl-C(=O)—, —C(=O)O, (C$_1$-C$_{10}$)alkylC(=O)O—, C(=O)N—, (C$_1$-C$_{10}$)alkylC(=O)—, C(=O)S— and (C$_1$-C$_{10}$)alkyl-C(=O)S— being R'$_{10}$ a radical selected from the group consisting of: hydrogen, (C$_1$-C$_{10}$)alkyl, (C$_2$-C$_{10}$)alkenyl, and (C$_1$-C$_{10}$)alkynyl;
the L birradical being bound to the backbone of the peptide sequence of formula (IV) via X$_7$ and X$_9$ birradicals, or alternatively via X$_{10}$ and X$_{12}$ birradicals,
the X birradicals which are bound to L birradical having the same or different meaning and being of formula (III):

wherein
the L birradical binds to the X birradical of formula (III) via the alpha carbon atom;
R$_{11}$ is a monoradical selected from the group consisting of: (C$_1$-C$_{10}$)alkyl, (C$_2$-C$_{10}$)alkenyl, (C$_2$-C$_{10}$)alkynyl, (C$_1$-C$_{10}$)alkyl-O—(C$_1$-C$_{10}$)alkyl, (C$_1$-C$_{10}$)alkyl-C(=O)—(C$_1$-C$_{10}$)alkyl, (C$_1$-C$_{10}$)alkyl-O—C(O)—(C$_1$-C$_{10}$)alkyl, (C$_1$-C$_{10}$)alkyl-C(O)—NR$_8$—(C$_1$-C$_{10}$)alkyl, (C$_1$-C$_{10}$)alkyl-S—(C$_1$-C$_{10}$)alkyl, (C$_1$-C$_{10}$)alkyl-SR$_9$—(C$_1$-C$_{10}$)alkyl, (C$_1$-C$_{10}$)alkyl-S(=O)$_2$—(C$_1$-C$_{10}$)alkyl, (C$_1$-C$_{10}$)alkyl-S(=O)—(C$_1$-C$_{10}$)alkyl, (C$_1$-C$_{10}$)alkyl-O—S(=O)$_2$—O—(C$_1$-C$_{10}$)alkyl, (C$_1$-C$_{10}$)alkyl-NR$_{10}$—(C$_1$-C$_{10}$)alkyl, and a known ring system comprising from 3 to 14 carbon atoms, the system comprising from 1 to 3 rings, where:
each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—;
and the other X birradicals of the backbone peptide sequence of formula (I), which are not bound to the "L" birradical, are the same or different and represent amino acids;
or, alternatively,
when "t" and "u" are 0, then X$_7$ to X$_{12}$ are the same or different and represent amino acids, provided that at least three of them are selected from the group consisting of:
X$_7$ represents an amino acid other than Val,
X$_8$ represents an amino acid other than Leu,
X$_9$ represents an amino acid other than Thr, and $X_{10}$ represents an amino acid other than Ala;
wherein:
the $(C_1-C_{10})$alkyl, $(C_2-C_{10})$alkenyl, and $(C_2-C_{10})$alkynyl are non-substituted or substituted,
"substituted $(C_1-C_{10})$alkyl" means that the $(C_1-C_{10})$alkyl is substituted by one or more radicals selected from the group consisting of:
halogen, —OR'$_{11}$, —NO$_2$, —NR'$_{11}$R$_{12}$, —SR'$_{11}$, —SO$_2$R'$_{11}$, —CO$_2$R'$_{11}$, and $(C_1-C_{10})$alkyl-O—, being R'$_{11}$ and R$_{12}$ the same or different and selected from the group consisting of: —H, $(C_1-C_{10})$alkyl, $(C_2-C_{10})$alkenyl, and $(C_1-C_{10})$alkynyl;
"substituted $(C_2-C_{10})$alkenyl" means that the $(C_2-C_{10})$ alkenyl is substituted by one or more radicals selected from the group consisting of:
halogen, —OR'$_{11}$, —NO$_2$, —NR'$_{11}$R$_{12}$, —SR'$_{11}$, —SO$_2$R'$_{11}$, —CO$_2$R'$_{11}$, and $(C_1-C_{10})$alkyl-O—, being R'$_{11}$ and R$_{12}$ the same or different and selected from the group consisting of: —H, $(C_1-C_{10})$alkyl, $(C_2-C_{10})$alkenyl, and $(C_1-C_{10})$alkynyl; and
"substituted $(C_2-C_{10})$alkynyl" means that the $(C_2-C_{10})$ alkynyl is substituted by one or more radicals selected from the group consisting of:
halogen, —OR'$_{11}$, —NO$_2$, —NR'$_{11}$R$_{12}$, —SR'$_{11}$, —SO$_2$R'$_{11}$, —CO$_2$R'$_{11}$, and $(C_1-C_{10})$alkyl-O—, being R'$_{11}$ and R$_{12}$ the same or different and selected from the group consisting of: —H, $(C_1-C_{10})$alkyl, $(C_2-C_{10})$alkenyl, and $(C_1-C_{10})$alkynyl.

Clause 3. The peptide according to any of the preceding clauses, wherein
when the peptide is one of formula (I), then one of "m", "n", "p", and "q" is 1, and at least one of the X's birradicals not bound to the "L" birradical is selected from the group consisting of:
$X_1$ represents an amino acid other than Glu,
$X_2$ represents an amino acid other than Lys,
$X_3$ represents an amino acid other than Ser,
$X_4$ represents an amino acid other than Phe,
$X_5$ represents an amino acid other than Ala, and
$X_6$ represents an amino acid other than Gln; or, alternatively,
when the peptide is one of formula (IV), then one of "t" and "u" is 1, and at least one of the X's birradicals not bound to the "L" birradical is selected from the group consisting of:
$X_7$ represents an amino acid other than Val,
$X_8$ represents an amino acid other than Leu,
$X_9$ represents an amino acid other than Thr, and
$X_{10}$ represents an amino acid other than Ala.

Clause 4. The peptide as defined in any of the clauses 1-2, wherein the peptide of formula (I) is one wherein "m", "n", "p", and "q", are 0, or alternatively, the peptide of formula (IV) is one wherein "t", and "u" are 0.

Clause 5. The peptide as defined in any of the previous clauses, wherein in the peptide of formula (I) v is 1, or alternatively, wherein in the peptide of formula (IV) z is 1.

Clause 6. The peptide as defined in any of the previous clauses, wherein L is a birradical of formula (II) wherein "a" and "b" are 0, "c" is 1, and R$_2$ is $(C_2-C_{10})$alkenyl.

Clause 7. The peptide as defined in any of the previous clauses, wherein L is a birradical wherein P and Q are the same or different and represent $(C_1-C_{10})$alkyl.

Clause 8. The peptide as defined in any of the previous clauses, wherein R$_{11}$ is $(C_1-C_{10})$alkyl.

Clause 9. The peptide or pharmaceutical salt thereof of any of the previous clauses 1-8, or alternatively,
a peptide comprising the sequence SEQ ID NO: 12:

Ala-Pro-Lys-Val-Val-Ile-Leu-Lys-Lys-Ala-Thr-Ala-Tyr-Ile or a variant thereof having at least a 85% of identity with SEQ ID NO: 12, or a pharmaceutical salt thereof,
which is conjugated to a label.

Clause 10. The peptide of any of the previous clauses, which is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

Clause 11. A veterinary or pharmaceutical composition comprising a therapeutically effective amount of the peptide or a pharmaceutical salt thereof as defined in any of the clauses 1-10 together with acceptable veterinary or pharmaceutical excipients and/or carriers.

Clause 12. A peptide or a pharmaceutical salt thereof as defined in any of the clauses 1-10 for use as a medicament.

Clause 13. A peptide or a pharmaceutical salt thereof as defined in any of the clauses 1-10 for use in the treatment of cancer.

Clause 14. The peptide or a pharmaceutical salt thereof for use as defined in clause 13, wherein the cancer is selected from the group consisting of: leukemia, breast cancer, lung cancer, myeloma, and lymphoma.

The invention claimed is:

1. A peptide or a pharmaceutical salt or active metabolite thereof, wherein the peptide comprises an amino acid sequence of formula:

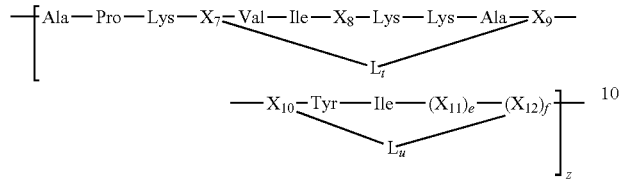

wherein
"t" is 1 and "u" is 0,
"e" and "f" are each 1, and
"z" is 1,
L is a birradical of formula (II):

wherein
"a" and "b" are the same or different and are 0 or 1;
"c" is an integer from 1 to 10;
$R_1$ and $R_3$ are birradicals independently selected from the group consisting of: $(C_1-C_{10})$alkyl, $(C_2-C_{10})$alkenyl, $(C_2-C_{10})$alkynyl, $(C_1-C_{10})$alkyl-O—$(C_1-C_{10})$alkyl, $(C_1-C_{10})$alkyl-C(=O)—$(C_1-C_{10})$alkyl, $(C_1-C_{10})$alkyl-O—C(O)—$(C_1-C_{10})$alkyl, $(C_1-C_{10})$alkyl-C(O)—$NR_8$—$(C_1-C_{10})$alkyl, $(C_1-C_{10})$alkyl-S—$(C_1-C_{10})$alkyl, $(C_1-C_{10})$alkyl-$SR_9$—$(C_1-C_{10})$alkyl, $(C_1-C_{10})$alkyl-S(=O)$_2$—$(C_1-C_{10})$alkyl, $(C_1-C_{10})$alkyl-S(=O)—$(C_1-C_{10})$alkyl, $(C_1-C_{10})$alkyl-O—S(=O)$_2$—O—$(C_1-C_{10})$alkyl, $(C_1-C_{10})$alkyl-$NR_{10}$—$(C_1-C_{10})$alkyl;
$R_2$ is a birradical selected from the group consisting of: O, C(=O), C(=O)$R_4$, C(=O)$NR_5$, C(=O)O, S(=O), S(=O)$_2$, S($R_6$), N($R_7$), $(C_1-C_{10})$alkyl, $(C_2-C_{10})$alkenyl, $(C_2-C_{10})$alkynyl, $NR_{13}R_{14}$, —NH—NH—, —N=N—, —S—S—, and a known ring system comprising from 3 to 14 carbon atoms, the known ring system comprising from 1 to 3 rings, where:
each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the known ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—;
$R_4$, $R_5$, $R_6$, $R_7$, $R_8$, $R_9$, $R_{10}$, $R_{13}$, and $R_{14}$ are monoradicals selected from the group consisting of: hydrogen, $(C_1-C_{10})$alkyl, $(C_2-C_{10})$alkenyl, and $(C_2-C_{10})$alkynyl;
when "a" and "b" are 0, or alternatively one of "a" and "b" is 0, then:
P and Q are birradicals and P and Q have a meaning different from the $R_2$ biradical, said P and Q birradicals being selected from the group consisting of: $(C_1-C_{10})$alkyl, $(C_2-C_{10})$alkenyl, and $(C_2-C_{10})$alkynyl; or P and Q are C(=O) and $R_2$ is selected from the group consisting of: —O—, S($R_6$), N($R_7$), $(C_1-C_{10})$alkyl, $(C_2-C_{10})$alkenyl, $(C_2-C_{10})$alkynyl, $NR_{13}R_{14}$, —NH—NH—, —N=N—, —S—S—, and a known ring system comprising from 3 to 14 carbon atoms, the system comprising from 1 to 3 rings, where:
each one of the rings is saturated, partially unsaturated, or aromatic;
the rings are isolated, partially or totally fused;
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, $(C_1-C_{10})$alkyl, $(C_1-C_{10})$haloalkyl, and $(C_1-C_{10})$alkyl-O—;
when both "a" and "b", are 1, then P and Q are selected from the group consisting of: —S—, $(C_1-C_{10})$alkyl-S—, —NR'$_{10}$—, $(C_1-C_{10})$alkyl-NR'$_{10}$, —O—, $(C_1-C_{10})$-alkyl-O—, —C(=O), $(C_1-C_{10})$alkyl-C(=O)—, —C(=O)O, $(C_1-C_{10})$ alkylC(=O)O—, C(=O)N—, $(C_1-C_{10})$alkyl-C(=O)N—, C(=O)S— and $(C_1-C_{10})$alkyl-C(=O)S—, wherein R'$_{10}$ a radical selected from the group consisting of: hydrogen, $(C_1-C_{10})$alkyl, $(C_2-C_{10})$alkenyl, and $(C_1-C_{10})$alkynyl;
wherein L is bound to the backbone of the amino acid sequence via $X_7$ and $X_9$, wherein the $X_7$ and $X_9$ have the same or different meaning and are of formula (III):

wherein:
L binds to $X_7$ and $X_9$ via the alpha carbon atom of formula (III);
$R_{11}$ is a monoradical selected from the group consisting of: $(C_1-C_{10})$alkyl, $(C_2-C_{10})$alkenyl, $(C_2-C_{10})$alkynyl, $(C_1-C_{10})$alkyl-O—$(C_1-C_{10})$alkyl, $(C_1-C_{10})$alkyl-C(=O)—$(C_1-C_{10})$alkyl, $(C_1-C_{10})$alkyl-O—C(O)—$(C_1-C_{10})$alkyl, $(C_1-C_{10})$alkyl-C(O)—$NR_8$—$(C_1-C_{10})$alkyl, $(C_1-C_{10})$alkyl-S—$(C_1-C_{10})$alkyl, $(C_1-C_{10})$alkyl-$SR_9$—$(C_1-C_{10})$alkyl, $(C_1-C_{10})$alkyl-S(=O)$_2$—$(C_1-C_{10})$alkyl, $(C_1-C_{10})$alkyl-S(=O)—$(C_1-C_{10})$alkyl, $(C_1-C_{10})$alkyl-O—S(=O)$_2$—O—$(C_1-C_{10})$alkyl, $(C_1-C_{10})$alkyl-$NR_{10}$—$(C_1-C_{10})$alkyl, and a known ring system comprising from 3 to 14 carbon atoms, the known ring system comprising from 1 to 3 rings, where:
each one of the rings is saturated, partially unsaturated, or aromatic;
the rings are isolated, partially or totally fused;
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—; and either:

X$_8$ is Leu and X$_{10}$ is Ala, or

X$_8$ is Phe and X$_{10}$ is Ala;

X$_{11}$ and X$_{12}$ are the same or different and represent amino acids;

wherein the (C$_1$-C$_{10}$)alkyl, (C$_2$-C$_{10}$)alkenyl, and (C$_2$-C$_{10}$)alkynyl are non-substituted or substituted, "substituted (C$_1$-C$_{10}$)alkyl" means that the (C$_1$-C$_{10}$) alkyl is substituted by one or more radicals selected from the group consisting of: halogen, —OR'$_{11}$, —NO$_2$, —NR'$_{11}$R$_{12}$, —SR'$_{11}$, —SO$_2$R'$_{11}$, —CO$_2$R'$_{11}$, and (C$_1$-C$_{10}$)alkyl-O—, being R'$_{11}$ and R$_{12}$ the same or different and selected from the group consisting of: —H, (C$_1$-C$_{10}$)alkyl, (C$_2$-C$_{10}$)alkenyl, and (C$_1$-C$_{10}$)alkynyl;

"substituted (C$_2$-C$_{10}$)alkenyl" means that the (C$_2$-C$_{10}$)alkenyl is substituted by one or more radicals selected from the group consisting of: halogen, —OR'$_{11}$, —NO$_2$, —NR'$_{11}$R$_{12}$, —SR'$_{11}$, —SO$_2$R'$_{11}$, —CO$_2$R'$_{11}$, and (C$_1$-C$_{10}$)alkyl-O—, being R'$_{11}$ and R$_{12}$ the same or different and selected from the group consisting of: —H, (C$_1$-C$_{10}$)alkyl, (C$_2$-C$_{10}$)alkenyl, and (C$_1$-C$_{10}$)alkynyl; and "substituted (C$_2$-C$_{10}$)alkynyl" means that the (C$_2$-C$_{10}$)alkynyl is substituted by one or more radicals selected from the group consisting of: halogen, —OR'$_{11}$, —NO$_2$, —NR'$_{11}$R$_{12}$, —SR'$_{11}$, —SO$_2$R'$_{11}$, —CO$_2$R'$_{11}$, and (C$_1$-C$_{10}$)alkyl-O—, being R'$_{11}$ and R$_{12}$ the same or different and selected from the group consisting of: —H, (C$_1$-C$_{10}$)alkyl, (C$_2$-C$_{10}$)alkenyl, and (C$_1$-C$_{10}$)alkynyl; and wherein the active metabolite lacks 1 amino acid in the N-terminal region or from 1 to 3 amino acids of the C-terminal region, or both.

2. The peptide or pharmaceutical salt or active metabolite thereof according to claim 1, wherein "a" and "b" are 0, and "c" is 1.

3. The peptide or pharmaceutical salt or active metabolite thereof according to claim 1, wherein P and Q are the same or different and represent a (C$_1$-C$_{10}$)alkyl, (C$_2$-C$_{10}$)alkenyl, or (C$_2$-C$_{10}$)alkynyl radical, said radicals being substituted or non-substituted.

4. The peptide or pharmaceutical salt or active metabolite thereof according to claim 1, wherein P and Q represent (C$_1$-C$_{10}$)alkyl radicals.

5. The peptide or pharmaceutical salt or active metabolite thereof according to claim 1, wherein R$_2$ represents a (C$_1$-C$_{10}$)alkyl, (C$_2$-C$_{10}$)alkenyl, or (C$_2$-C$_{10}$)alkynyl radical, said radical being substituted or non-substituted.

6. The peptide or pharmaceutical salt or active metabolite thereof according to claim 1, wherein R$_2$ represents a (C$_2$-C$_{10}$)alkenyl radical.

7. The peptide or pharmaceutical salt or active metabolite thereof according to claim 1, wherein L is of formula (VII)

—(CH$_2$)$_x$—CH=CH—(CH$_2$)$_y$— wherein x and y are the same or different and are integers from 1 to 10.

8. The peptide or pharmaceutical salt or active metabolite thereof according to claim 1, wherein X$_7$ and X$_9$ are the same.

9. The peptide or pharmaceutical salt or active metabolite thereof according to claim 1, wherein R$_{11}$ represents a (C$_1$-C$_{10}$)alkyl radical.

10. The peptide or pharmaceutical salt or active metabolite thereof according to claim 1, wherein R$_{11}$ represents a methyl radical.

11. The peptide or pharmaceutical salt or active metabolite thereof according to claim 1, wherein X$_{11}$ represents a non-polar amino acid.

12. The peptide or pharmaceutical salt or active metabolite thereof according to claim 1, wherein X$_{12}$ represents a polar neutral amino acid.

13. The peptide or pharmaceutical salt or active metabolite thereof according to claim 1, which comprises the sequence SEQ ID NO: 8.

14. The peptide or pharmaceutical salt or active metabolite thereof according to claim 1, which consists of sequence SEQ ID NO: 8.

15. The peptide or pharmaceutical salt or active metabolite thereof of claim 1 which is conjugated to a label.

16. A fusion protein comprising the peptide or pharmaceutical salt or active metabolite thereof of claim 1.

17. A veterinary or pharmaceutical composition comprising a therapeutically effective amount of the peptide or pharmaceutical salt or active metabolite thereof of claim 1, together with acceptable veterinary or pharmaceutical excipients, or carriers, or combinations thereof.

18. The peptide or pharmaceutical salt or active metabolite thereof according to claim 1, which comprises the amino acid sequence of SEQ ID NO: 9.

19. The peptide or pharmaceutical salt or active metabolite thereof according to claim 18, which consists of the amino acid sequence of SEQ ID NO: 9.

20. A method of treating cancer, comprising administering an effective amount of the peptide or pharmaceutical salt or active metabolite thereof of claim 1, to a subject in need thereof, wherein the cancer is selected from the group consisting of: leukemia, breast cancer, lung cancer, myeloma, and lymphoma.

21. The peptide or pharmaceutical salt or active metabolite thereof of claim 15, wherein said label is selected from the group consisting of electron spin resonance molecule, a fluorescent molecule, a chemiluminescent molecule, a radioisotope, an enzyme substrate, an enzyme, a biotin molecule, an avidin molecule, an electrical charge transferring molecule, a semiconductor nanocrystal, a semiconductor nanoparticle, a colloid gold nanocrystal, a ligand, a microbead, a magnetic bead, a paramagnetic molecule, a quantum dot, a chromogenic substrate, an affinity molecule, a protein, a peptide, nucleic acid, a carbohydrate, a hapten, an antigen, an antibody, an antibody fragment, and a lipid.

22. The peptide or pharmaceutical salt or active metabolite thereof of claim 1, wherein said peptide is conjugated to an agent which improves the bioavailability profile of the peptide.

23. The peptide or pharmaceutical salt or active metabolite thereof of claim 1, wherein X$_8$ is Leu and X$_{10}$ is Ala.

24. The peptide or pharmaceutical salt or active metabolite thereof of claim 1, wherein X$_8$ is Phe and X$_{10}$ is Ala.

25. The method of treating cancer according to claim 20, wherein the method further comprises administering an effective amount of one or more other anti-cancer agents.

* * * * *

SEQUENCE LISTING

```
<160> NUMBER OF SEQ ID NOS: 53

<210> SEQ ID NO 1
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (6)..(6)
<223> OTHER INFORMATION: it corresponds to a compound of formula (III)
      wherein R11 is -CH3; and this residue binds to residue at position
      10 via a L birradical which is a -(CH2)3-CH=CH-(CH2)3-
<220> FEATURE:
<221> NAME/KEY: misc_feature
<222> LOCATION: (10)..(10)
<223> OTHER INFORMATION: it corresponds to a compound of formula (III)
      wherein R11 is -CH3
```

<400> SEQUENCE: 1

Arg Gln Arg Arg Asn Xaa Leu Lys Arg Xaa Phe Ala Ala Leu Arg Asp
1               5                   10                  15

Gln

<210> SEQ ID NO 2
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (10)..(10)
<223> OTHER INFORMATION: it corresponds to a compound of formula (III)
      wherein R11 is -CH3; and this residue binds to residue at position
      17 via a L birradical which is a -(CH2)6-CH=CH-(CH2)3-
<220> FEATURE:
<221> NAME/KEY: misc_feature
<222> LOCATION: (17)..(17)
<223> OTHER INFORMATION: it corresponds to a compound of formula (III)
      wherein R11 is -CH3

<400> SEQUENCE: 2

Arg Gln Arg Arg Asn Glu Leu Lys Arg Xaa Phe Ala Ala Leu Arg Asp
1               5                   10                  15

Xaa

<210> SEQ ID NO 3
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (10)..(10)
<223> OTHER INFORMATION: it corresponds to a compound of formula (III)
      wherein R11 is -CH3; and this residue binds to residue at position
      17 via a L birradical which is a -(CH2)6-CH=CH-(CH2)3-
<220> FEATURE:
<221> NAME/KEY: MISC_FEATURE
<222> LOCATION: (17)..(17)
<223> OTHER INFORMATION: it corresponds to a compound of formula (III)
      wherein R11 is -CH3

<400> SEQUENCE: 3

Arg Gln Arg Arg Asn Glu Leu Lys Arg Xaa Phe Phe Ala Leu Arg Asp
1               5                   10                  15

Xaa

<210> SEQ ID NO 4
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (6)..(6)
<223> OTHER INFORMATION: it corresponds to a compound of formula (III)
      wherein R11 is -CH3; and this residue binds to residue at position
      13 via a L birradical which is a -(CH2)6-CH=CH-(CH2)3-
<220> FEATURE:
<221> NAME/KEY: MISC_FEATURE
<222> LOCATION: (13)..(13)
<223> OTHER INFORMATION: it corresponds to a compound of formula (III)
      wherein R11 is -CH3

```
<400> SEQUENCE: 4

Asn Glu Leu Lys Arg Xaa Phe Phe Ala Leu Arg Asp Xaa
1               5                   10

<210> SEQ ID NO 5
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (8)..(8)
<223> OTHER INFORMATION: it corresponds to a compound of formula (III)
      wherein R11 is -CH3; and this residue binds to residue at position
      12 via a L birradical which is a -(CH2)3-CH=CH-(CH2)3-
<220> FEATURE:
<221> NAME/KEY: MISC_FEATURE
<222> LOCATION: (12)..(12)
<223> OTHER INFORMATION: it corresponds to a compound of formula (III)
      wherein R11 is -CH3

<400> SEQUENCE: 5

Arg Gln Arg Arg Asn Glu Leu Xaa Arg Ala Phe Xaa Ala Leu Arg Asp
1               5                   10                  15

Gln

<210> SEQ ID NO 6
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (6)..(6)
<223> OTHER INFORMATION: it corresponds to a compound of formula (III)
      wherein R11 is -CH3; and this residue binds to residue at position
      13 via a L birradical which is a -(CH2)6-CH=CH-(CH2)3-
<220> FEATURE:
<221> NAME/KEY: MISC_FEATURE
<222> LOCATION: (13)..(13)
<223> OTHER INFORMATION: it corresponds to a compound of formula (III)
      wherein R11 is -CH3

<400> SEQUENCE: 6

Arg Gln Arg Arg Asn Xaa Leu Lys Arg Ala Phe Ala Xaa Leu Arg Asp
1               5                   10                  15

Gln

<210> SEQ ID NO 7
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: the N(t) is HOC(O)(CH2)2C(O)NH- and the C(t) is
      -CONH2

<400> SEQUENCE: 7

Arg Gln Arg Arg Asn Glu Leu Lys Arg Leu Phe Phe Thr Leu Arg Asp
1               5                   10                  15

Ile

<210> SEQ ID NO 8
```

```
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: it corresponds to a compound of formula (III)
      wherein R11 is -CH3; and this residue binds to residue at position
      11 via a L birradical which is a -(CH2)6-CH=CH-(CH2)3-
<220> FEATURE:
<221> NAME/KEY: MISC_FEATURE
<222> LOCATION: (11)..(11)
<223> OTHER INFORMATION: it corresponds to a compound of formula (III)
      wherein R11 is -CH3

<400> SEQUENCE: 8

Ala Pro Lys Xaa Val Ile Leu Lys Lys Ala Xaa Ala Tyr Ile Leu Ser
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: it corresponds to a compound of formula (III)
      wherein R11 is -CH3; and this residue binds to residue at position
      11 via a L birradical which is a -(CH2)6-CH=CH-(CH2)3-
<220> FEATURE:
<221> NAME/KEY: MISC_FEATURE
<222> LOCATION: (11)..(11)
<223> OTHER INFORMATION: it corresponds to a compound of formula (III)
      wherein R11 is -CH3

<400> SEQUENCE: 9

Ala Pro Lys Xaa Val Ile Phe Lys Lys Ala Xaa Ala Tyr Ile Leu Ser
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (12)..(12)
<223> OTHER INFORMATION: it corresponds to a compound of formula (III)
      wherein R11 is CH3; and this residue binds to residue at position
      16 via a L birradical which is a -(CH2)3-CH=CH-(CH2)3-
<220> FEATURE:
<221> NAME/KEY: MISC_FEATURE
<222> LOCATION: (16)..(16)
<223> OTHER INFORMATION: it corresponds to a compound of formula (III)
      wherein R11 is CH3

<400> SEQUENCE: 10

Ala Pro Lys Val Val Ile Leu Lys Lys Ala Thr Xaa Tyr Ile Leu Xaa
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
```

```
<222> LOCATION: (1)..(1)
<223> OTHER INFORMATION: the N(t) is HOC(O)(CH2)2C(O)NH- and the C(t) is
      -CONH2

<400> SEQUENCE: 11

Ala Pro Lys Ile Val Ile Phe Lys Lys Ala Leu Ala Tyr Ile
1               5                   10

<210> SEQ ID NO 12
<211> LENGTH: 14
<212> TYPE: PRT
<213> ORGANISM: Artificial Sequence
<220> FEATURE:
<223> OTHER INFORMATION: peptide

<400> SEQUENCE: 12

Ala Pro Lys Val Val Ile Leu Lys Lys Ala Thr Ala Tyr Ile
1               5                   10

<210> SEQ ID NO 13
<211> LENGTH: 21
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: the N(t) is HOC(O)(CH2)2C(O)NH- and the C(t) is
      -CONH2

<400> SEQUENCE: 13

Arg Arg Arg Arg Arg Arg Arg Ala Pro Lys Val Val Ile Leu Lys Lys
1               5                   10                  15

Ala Thr Ala Tyr Ile
            20

<210> SEQ ID NO 14
<211> LENGTH: 21
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: the N(t) is HOC(O)(CH2)2C(O)NH- and the C(t) is
      -CONH2

<400> SEQUENCE: 14

Arg Arg Arg Arg Arg Arg Arg Ala Pro Lys Ile Val Ile Ser Lys Lys
1               5                   10                  15

Ala Leu Ala Tyr Ile
            20

<210> SEQ ID NO 15
<211> LENGTH: 21
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (1)..(1)
<223> OTHER INFORMATION: the N(t) is HOC(O)(CH2)2C(O)NH- and the C(t) is
      -CONH2

<400> SEQUENCE: 15
```

```
Arg Arg Arg Arg Arg Arg Arg Ala Pro Lys Ile Val Ile Phe Lys Lys
1               5                   10                  15

Ala Leu Ala Tyr Ile
            20

<210> SEQ ID NO 16
<211> LENGTH: 30
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: the N(t) is HOC(O)(CH2)2C(O)NH- and the C(t) is
      -CONH2

<400> SEQUENCE: 16

Arg Gln Ile Lys Ile Trp Phe Gln Asn Arg Arg Met Lys Trp Lys Lys
1               5                   10                  15

Ala Pro Lys Val Val Ile Leu Lys Lys Ala Thr Ala Tyr Ile
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: the N(t) is HOC(O)(CH2)2C(O)NH- and the C(t) is
      -CONH2

<400> SEQUENCE: 17

Arg Gln Ile Lys Ile Trp Phe Gln Asn Arg Arg Met Lys Trp Lys Lys
1               5                   10                  15

Ala Pro Lys Ile Val Ile Phe Lys Lys Ala Leu Ala Tyr Ile
            20                  25                  30

<210> SEQ ID NO 18
<211> LENGTH: 13
<212> TYPE: PRT
<213> ORGANISM: Artificial Sequence
<220> FEATURE:
<223> OTHER INFORMATION: peptide

<400> SEQUENCE: 18

Asn Glu Leu Lys Arg Ser Phe Phe Ala Leu Arg Asp Gln
1               5                   10

<210> SEQ ID NO 19
<211> LENGTH: 17
<212> TYPE: PRT
<213> ORGANISM: Artificial Sequence
<220> FEATURE:
<223> OTHER INFORMATION: peptide

<400> SEQUENCE: 19

Arg Gln Arg Arg Asn Glu Leu Lys Arg Ser Phe Ala Ala Leu Arg Asp
1               5                   10                  15

Gln

<210> SEQ ID NO 20
<211> LENGTH: 4
```

```
<212> TYPE: PRT
<213> ORGANISM: Artificial Sequence
<220> FEATURE:
<223> OTHER INFORMATION: peptide

<400> SEQUENCE: 20

Arg Gln Arg Arg
1

<210> SEQ ID NO 21
<211> LENGTH: 13
<212> TYPE: PRT
<213> ORGANISM: Artificial Sequence
<220> FEATURE:
<223> OTHER INFORMATION: peptide

<400> SEQUENCE: 21

Pro Lys Val Val Ile Leu Lys Lys Ala Thr Ala Tyr Ile
1               5                   10

<210> SEQ ID NO 22
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
<220> FEATURE:
<221> NAME/KEY: MISC_FEATURE
<222> LOCATION: (9)..(9)
<223> OTHER INFORMATION: it corresponds to a compound of formula (III)
      wherein R11 is -CH3

<400> SEQUENCE: 22

Ala Xaa Lys Val Val Ile Leu Lys Xaa Ala Thr Ala Tyr Ile Leu Ser
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (5)..(5)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
<220> FEATURE:
<221> NAME/KEY: MISC_FEATURE
<222> LOCATION: (12)..(12)
<223> OTHER INFORMATION: it corresponds to a compound of formula (III)
      wherein R11 is -CH3

<400> SEQUENCE: 23

Ala Pro Lys Val Xaa Ile Leu Lys Lys Ala Thr Xaa Tyr Ile Leu Ser
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: peptide
<220> FEATURE:
```

```
<221> NAME/KEY: MISC_FEATURE
<222> LOCATION: (6)..(6)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
<220> FEATURE:
<221> NAME/KEY: MISC_FEATURE
<222> LOCATION: (13)..(13)
<223> OTHER INFORMATION: it corresponds to a compound of formula (III)
      wherein R11 is -CH3

<400> SEQUENCE: 24

Ala Pro Lys Val Val Xaa Leu Lys Lys Ala Thr Ala Xaa Ile Leu Ser
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (9)..(9)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
<220> FEATURE:
<221> NAME/KEY: MISC_FEATURE
<222> LOCATION: (16)..(16)
<223> OTHER INFORMATION: it corresponds to a compound of formula (III)
      wherein R11 is -CH3

<400> SEQUENCE: 25

Ala Pro Lys Val Val Ile Leu Lys Xaa Ala Thr Ala Tyr Ile Leu Xaa
1               5                   10                  15

Val

<210> SEQ ID NO 26
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (7)..(7)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
<220> FEATURE:
<221> NAME/KEY: MISC_FEATURE
<222> LOCATION: (14)..(14)
<223> OTHER INFORMATION: it corresponds to a compound of formula (III)
      wherein R11 is -CH3

<400> SEQUENCE: 26

Ala Pro Lys Val Val Ile Xaa Lys Lys Ala Thr Ala Tyr Xaa Leu Ser
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (8)..(8)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
```

```
<220> FEATURE:
<221> NAME/KEY: MISC_FEATURE
<222> LOCATION: (15)..(15)
<223> OTHER INFORMATION: it corresponds to a compound of formula (III)
      wherein R11 is -CH3

<400> SEQUENCE: 27

Ala Pro Lys Val Val Ile Leu Xaa Lys Ala Thr Ala Tyr Ile Xaa Ser
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (7)..(7)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
<220> FEATURE:
<221> NAME/KEY: MISC_FEATURE
<222> LOCATION: (14)..(14)
<223> OTHER INFORMATION: it corresponds to a compound of formula (III)
      wherein R11 is -CH3

<400> SEQUENCE: 28

Ala Pro Lys Ile Val Ile Xaa Lys Lys Ala Leu Ala Tyr Xaa Leu Ser
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (6)..(6)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
<220> FEATURE:
<221> NAME/KEY: MISC_FEATURE
<222> LOCATION: (13)..(13)
<223> OTHER INFORMATION: it corresponds to a compound of formula (III)
      wherein R11 is -CH3

<400> SEQUENCE: 29

Arg Gln Arg Arg Asn Xaa Leu Lys Arg Ala Phe Ala Xaa Leu Arg Asp
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (5)..(5)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
<220> FEATURE:
<221> NAME/KEY: MISC_FEATURE
<222> LOCATION: (12)..(12)
<223> OTHER INFORMATION: it corresponds to a compound of formula (III)
      wherein R11 is -CH3

<400> SEQUENCE: 30
```

```
Gln Arg Arg Asn Xaa Leu Lys Arg Ala Phe Ala Xaa Leu Arg Asp
1               5                   10                  15
```

<210> SEQ ID NO 31
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (5)..(5)
<223> OTHER INFORMATION: it corresponds to a compound of formula (III)
      wherein R11 is -CH3; and this X residue binds to the X residue at
      position 9 via a L birradical which is -(CH2)6-CH=CH-(CH2)3-
<220> FEATURE:
<221> NAME/KEY: MISC_FEATURE
<222> LOCATION: (5)..(5)
<223> OTHER INFORMATION: it corresponds to a compound of formula (III)
      wherein R11 is -CH3
<220> FEATURE:
<221> NAME/KEY: misc_feature
<222> LOCATION: (12)..(12)
<223> OTHER INFORMATION: Xaa can be any naturally occurring amino acid

<400> SEQUENCE: 31

```
Gln Arg Arg Asn Xaa Leu Lys Arg Ala Phe Ala Xaa Leu Arg Asp Gln
1               5                   10                  15
```

<210> SEQ ID NO 32
<211> LENGTH: 17
<212> TYPE: PRT
<213> ORGANISM: Artificial Sequence
<220> FEATURE:
<223> OTHER INFORMATION: peptide

<400> SEQUENCE: 32

```
Arg Gln Arg Arg Asn Glu Leu Lys Arg Ala Phe Ala Ala Leu Arg Asp
1               5                   10                  15

Gln
```

<210> SEQ ID NO 33
<211> LENGTH: 17
<212> TYPE: PRT
<213> ORGANISM: Artificial Sequence
<220> FEATURE:
<223> OTHER INFORMATION: peptide

<400> SEQUENCE: 33

```
Arg Gln Arg Arg Asn Glu Leu Lys Arg Ser Phe Phe Ala Leu Arg Asp
1               5                   10                  15

Gln
```

<210> SEQ ID NO 34
<211> LENGTH: 21
<212> TYPE: PRT
<213> ORGANISM: Artificial Sequence
<220> FEATURE:
<223> OTHER INFORMATION: Synthetic peptide

<400> SEQUENCE: 34

```
Arg Arg Arg Arg Arg Arg Arg Ala Pro Lys Val Val Ile Leu Lys Lys
1               5                   10                  15

Ala Thr Ala Tyr Ile
            20
```

```
<210> SEQ ID NO 35
<211> LENGTH: 21
<212> TYPE: PRT
<213> ORGANISM: Artificial Sequence
<220> FEATURE:
<223> OTHER INFORMATION: Synthetic peptide

<400> SEQUENCE: 35

Arg Arg Arg Arg Arg Arg Arg Ala Pro Lys Ile Val Ile Phe Lys Lys
1               5                   10                  15

Ala Leu Ala Tyr Ile
            20

<210> SEQ ID NO 36
<211> LENGTH: 13
<212> TYPE: PRT
<213> ORGANISM: Artificial Sequence
<220> FEATURE:
<223> OTHER INFORMATION: Synthetic peptide

<400> SEQUENCE: 36

Asn Glu Leu Lys Arg Ser Phe Phe Ala Leu Arg Asp Gln
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Synthetic peptide

<400> SEQUENCE: 37

Arg Gln Arg Arg Asn Glu Leu Lys Arg Ser Phe Phe Ala Leu Arg Asp
1               5                   10                  15

Gln

<210> SEQ ID NO 38
<211> LENGTH: 17
<212> TYPE: PRT
<213> ORGANISM: Artificial Sequence
<220> FEATURE:
<223> OTHER INFORMATION: Synthetic peptide

<400> SEQUENCE: 38

Arg Gln Arg Arg Asn Glu Leu Lys Arg Ser Phe Ala Ala Leu Arg Asp
1               5                   10                  15

Gln

<210> SEQ ID NO 39
<211> LENGTH: 17
<212> TYPE: PRT
<213> ORGANISM: Artificial Sequence
<220> FEATURE:
<223> OTHER INFORMATION: Synthetic peptide

<400> SEQUENCE: 39

Arg Gln Arg Arg Asn Glu Leu Lys Arg Ala Phe Ala Ala Leu Arg Asp
1               5                   10                  15

Gln

<210> SEQ ID NO 40
<211> LENGTH: 13
<212> TYPE: PRT
<213> ORGANISM: Artificial Sequence
<220> FEATURE:
```

```
<223> OTHER INFORMATION: Synthetic peptide

<400> SEQUENCE: 40

Pro Lys Ile Val Ile Phe Lys Lys Ala Leu Ala Tyr Ile
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic peptide

<400> SEQUENCE: 41

Ala Pro Lys Ile Val Ile Phe Lys Lys Ala Leu Ala Tyr
1               5                   10

<210> SEQ ID NO 42
<211> LENGTH: 30
<212> TYPE: PRT
<213> ORGANISM: Artificial Sequence
<220> FEATURE:
<223> OTHER INFORMATION: Synthetic peptide

<400> SEQUENCE: 42

Arg Gln Ile Lys Ile Trp Phe Gln Asn Arg Arg Met Lys Trp Lys Lys
1               5                   10                  15

Ala Pro Lys Val Val Ile Leu Lys Lys Ala Thr Ala Tyr Ile
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Synthetic peptide

<400> SEQUENCE: 43

Arg Gln Ile Lys Ile Trp Phe Gln Asn Arg Arg Met Lys Trp Lys Lys
1               5                   10                  15

Ala Pro Lys Ile Val Ile Phe Lys Lys Ala Leu Ala Tyr Ile
            20                  25                  30

<210> SEQ ID NO 44
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(17)
<223> OTHER INFORMATION: Xaa = Any Amino Acid

<400> SEQUENCE: 44

Arg Gln Arg Arg Asn Xaa Leu Lys Arg Xaa Phe Ala Ala Leu Arg Asp
1               5                   10                  15

Gln

<210> SEQ ID NO 45
<211> LENGTH: 17
<212> TYPE: PRT
<213> ORGANISM: Artificial Sequence
<220> FEATURE:
<223> OTHER INFORMATION: Synthetic peptide
<220> FEATURE:
```

<221> NAME/KEY: VARIANT
<222> LOCATION: (1)...(17)
<223> OTHER INFORMATION: Xaa = Any Amino Acid

<400> SEQUENCE: 45

Arg Gln Arg Arg Asn Xaa Leu Lys Arg Ala Phe Ala Xaa Leu Arg Asp
1               5                   10                  15

Gln

<210> SEQ ID NO 46
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(17)
<223> OTHER INFORMATION: Xaa = Any Amino Acid

<400> SEQUENCE: 46

Arg Gln Arg Arg Asn Glu Leu Lys Arg Xaa Phe Ala Ala Leu Arg Asp
1               5                   10                  15

Xaa

<210> SEQ ID NO 47
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(16)
<223> OTHER INFORMATION: Xaa = Any Amino Acid

<400> SEQUENCE: 47

Ala Pro Lys Xaa Val Ile Leu Lys Lys Ala Xaa Ala Tyr Ile Leu Ser
1               5                   10                  15

<210> SEQ ID NO 48
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(17)
<223> OTHER INFORMATION: Xaa = Any Amino Acid

<400> SEQUENCE: 48

Arg Gln Arg Arg Asn Glu Leu Lys Arg Xaa Phe Phe Ala Leu Arg Asp
1               5                   10                  15

Xaa

<210> SEQ ID NO 49
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(13)
<223> OTHER INFORMATION: Xaa = Any Amino Acid

<400> SEQUENCE: 49

```
Asn Glu Leu Lys Arg Xaa Phe Phe Ala Leu Arg Asp Xaa
1               5                   10
```

<210> SEQ ID NO 50
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(16)
<223> OTHER INFORMATION: Xaa = Any Amino Acid

<400> SEQUENCE: 50

```
Ala Pro Lys Xaa Val Ile Phe Lys Lys Ala Xaa Ala Tyr Ile Leu Ser
1               5                   10                  15
```

<210> SEQ ID NO 51
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(16)
<223> OTHER INFORMATION: Xaa = Any Amino Acid

<400> SEQUENCE: 51

```
Arg Gln Arg Arg Asn Xaa Leu Lys Arg Ala Phe Ala Xaa Leu Arg Asp
1               5                   10                  15
```

<210> SEQ ID NO 52
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(15)
<223> OTHER INFORMATION: Xaa = Any Amino Acid

<400> SEQUENCE: 52

```
Gln Arg Arg Asn Xaa Leu Lys Arg Ala Phe Ala Xaa Leu Arg Asp
1               5                   10                  15
```

<210> SEQ ID NO 53
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(17)
<223> OTHER INFORMATION: Xaa = Any Amino Acid

<400> SEQUENCE: 53

```
Arg Gln Arg Arg Asn Xaa Leu Lys Arg Ala Phe Ala Xaa Leu Arg Asp
1               5                   10                  15

Gln
```